(12) United States Patent
Zhi et al.

(10) Patent No.: US 8,519,158 B2
(45) Date of Patent: *Aug. 27, 2013

(54) ANDROGEN RECEPTOR MODULATOR COMPOUNDS AND METHODS

(75) Inventors: Lin Zhi, San Diego, CA (US); Robert I. Higuchi, Solana Beach, CA (US); Cornelis Arjan Van Oeveren, San Diego, CA (US); Thomas Lot Stevens Lau, San Diego, CA (US)

(73) Assignee: Ligand Pharmaceuticals Incorporated, San Diego, CA (US)

( * ) Notice: Subject to any disclaimer, the term of this patent is extended or adjusted under 35 U.S.C. 154(b) by 1624 days.

This patent is subject to a terminal disclaimer.

(21) Appl. No.: 10/590,119

(22) PCT Filed: Mar. 11, 2005

(86) PCT No.: PCT/US2005/007867
§ 371 (c)(1), (2), (4) Date: Jun. 11, 2007

(87) PCT Pub. No.: WO2005/090282
PCT Pub. Date: Sep. 29, 2005

(65) Prior Publication Data
US 2007/0254875 A1    Nov. 1, 2007

Related U.S. Application Data

(60) Provisional application No. 60/552,690, filed on Mar. 12, 2004.

(51) Int. Cl.
*C07D 295/04* (2006.01)
(52) U.S. Cl.
USPC .......................................... 548/577
(58) Field of Classification Search
USPC .......................................... 548/577
See application file for complete search history.

(56) References Cited

U.S. PATENT DOCUMENTS

| 3,710,795 | A | 1/1973 | Higuchi et al. | 424/424 |
| 3,847,988 | A | 11/1974 | Gold | 562/802 |

(Continued)

FOREIGN PATENT DOCUMENTS

| EP | 0711768 | 5/1976 |
| EP | 1122242 | 8/2001 |

(Continued)

OTHER PUBLICATIONS

Selvakumar et al. Synthesis (2002), (16), 2421-2425.*

(Continued)

*Primary Examiner* — Nizal Chandrakumar
(74) *Attorney, Agent, or Firm* — Knobbe Martens Olson & Bear, LLP

(57) ABSTRACT

Provided herein are compounds having a structure selected from among Formula (I), Formula (II), Formula (III), Formula (IV), Formula (V) and Formula (VI) that are androgen receptor modulators and/or androgen receptor binding agents. Also disclosed are methods of making and using such compounds, including, but not limited to, using such compounds for treating various conditions.

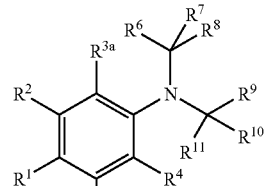

(I)

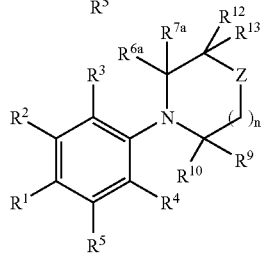

(II)

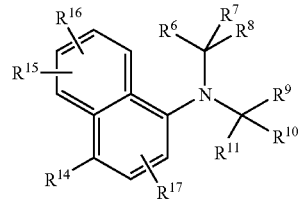

(III)

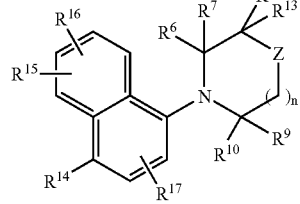

(IV)

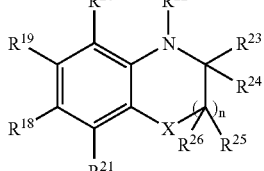

(V)

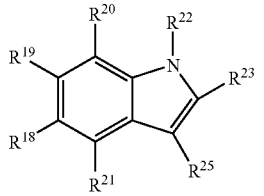

(VI)

44 Claims, No Drawings

(56) References Cited

U.S. PATENT DOCUMENTS

| | | | |
|---|---|---|---|
| RE28,819 E | 5/1976 | Thompson | 514/174 |
| 4,044,126 A | 8/1977 | Cook et al. | 514/180 |
| 4,097,578 A | 6/1978 | Perronnet et al. | 514/389 |
| 4,202,895 A | 5/1980 | Inaba et al. | 514/266.31 |
| 4,328,245 A | 5/1982 | Yu et al. | 514/530 |
| 4,358,603 A | 11/1982 | Yu | 560/2 |
| 4,364,923 A | 12/1982 | Cook et al. | 424/46 |
| 4,409,239 A | 10/1983 | Yu | 514/530 |
| 4,410,545 A | 10/1983 | Yu et al. | 514/530 |
| 4,414,209 A | 11/1983 | Cook et al. | 514/180 |
| 4,522,811 A | 6/1985 | Eppstein et al. | 514/2 |
| 4,636,505 A | 1/1987 | Tucker | 514/256 |
| 4,981,784 A | 1/1991 | Evans et al. | 435/6 |
| 5,033,252 A | 7/1991 | Carter | 53/425 |
| 5,052,558 A | 10/1991 | Carter | 206/439 |
| 5,071,773 A | 12/1991 | Evans et al. | 436/501 |
| 5,278,034 A * | 1/1994 | Ohki et al. | 430/440 |
| 5,323,907 A | 6/1994 | Kalvelage | 206/531 |
| 5,506,102 A | 4/1996 | McDonnell | 435/6 |
| 5,677,336 A | 10/1997 | Jones et al. | 514/546 |
| 5,688,808 A | 11/1997 | Jones et al. | 514/285 |
| 5,688,810 A | 11/1997 | Jones et al. | 514/311 |
| 5,693,646 A | 12/1997 | Jones et al. | 514/285 |
| 5,696,130 A | 12/1997 | Jones et al. | 514/291 |
| 5,696,133 A | 12/1997 | Jones et al. | 514/314 |
| 6,017,924 A | 1/2000 | Edwards et al. | 514/292 |
| 6,358,947 B1 | 3/2002 | Zhi et al. | 514/229.5 |
| 6,380,207 B2 | 4/2002 | Coghlan et al. | 514/285 |
| 6,437,167 B1 * | 8/2002 | Sunjic et al. | 558/419 |
| 6,462,038 B1 | 10/2002 | Higuchi et al. | 514/224.5 |
| 6,506,766 B1 | 1/2003 | Coghlan et al. | 514/285 |
| 6,534,516 B1 | 3/2003 | Edwards et al. | 514/285 |
| 6,566,372 B1 | 5/2003 | Zhi et al. | 514/312 |
| 6,569,896 B2 | 5/2003 | Dalton et al. | 514/493 |
| 6,667,313 B1 | 12/2003 | Hamann et al. | 514/292 |
| 6,673,799 B1 | 1/2004 | Taniguchi et al. | 514/253.01 |
| 6,696,459 B1 | 2/2004 | Jones et al. | 514/285 |
| 6,777,427 B2 | 8/2004 | Miyakawa et al. | 514/311 |
| 6,845,378 B1 | 1/2005 | Pauly et al. | 707/101 |
| 7,169,772 B2 | 1/2007 | Koshio et al. | 514/213.01 |
| 7,214,690 B2 * | 5/2007 | Higuchi et al. | 514/314 |
| 7,696,246 B2 | 4/2010 | Zhi et al. | 514/457 |
| 7,727,980 B2 | 6/2010 | Zhi et al. | 514/215 |
| 7,816,372 B2 | 10/2010 | Zhi et al. | 514/312 |
| 8,354,446 B2 * | 1/2013 | Zhi | 548/577 |
| 2002/0183314 A1 | 12/2002 | Higuchi et al. | 514/224.5 |
| 2002/0183346 A1 | 12/2002 | Zhi et al. | 514/291 |
| 2003/0055094 A1 | 3/2003 | Sun et al. | 514/379 |
| 2003/0212070 A1 * | 11/2003 | Schwink et al. | 514/241 |
| 2009/0227571 A1 | 9/2009 | Loren et al. | 514/228.5 |
| 2010/0069379 A1 | 3/2010 | Zhi et al. | 514/230.5 |
| 2010/0256129 A1 | 10/2010 | Zhi | 514/229.8 |
| 2012/0004220 A9 | 1/2012 | Zhi | 514/229.8 |

FOREIGN PATENT DOCUMENTS

| | | | |
|---|---|---|---|
| EP | 800519 | | 10/2003 |
| GB | 1177545 | * | 1/1970 |
| JP | 2002088073 | * | 3/2002 |
| WO | 95/11215 | | 4/1995 |
| WO | 95/31722 | | 11/1995 |
| WO | WO 96/19458 | | 6/1996 |
| WO | 97/49709 | | 12/1997 |
| WO | 98/22432 | | 5/1998 |
| WO | 00/66590 | | 11/2000 |
| WO | 01/16108 | | 3/2001 |
| WO | 01/16133 | | 3/2001 |
| WO | 01/16139 | | 3/2001 |
| WO | 01/27086 | | 4/2001 |
| WO | WO 0127107 | * | 4/2001 |
| WO | WO 0183460 | * | 11/2001 |
| WO | WO 2001083460 | * | 11/2001 |
| WO | 02/16310 | | 2/2002 |
| WO | 02/22585 | | 3/2002 |
| WO | 02/066475 | | 8/2002 |
| WO | 02/068427 | | 9/2002 |
| WO | 03/011824 | | 2/2003 |
| WO | 03/037905 | | 5/2003 |
| WO | WO 03042181 | * | 5/2003 |
| WO | WO 03/090672 | | 11/2003 |
| WO | 2004/016576 | | 2/2004 |
| WO | 2005/000795 | | 1/2005 |
| WO | WO 2005/090282 | | 9/2005 |
| WO | WO 2006/138347 | | 12/2006 |
| WO | WO 2007/075884 | | 7/2007 |
| WO | WO 2009/082437 | | 7/2009 |

OTHER PUBLICATIONS

Rettig et al. Journal of Physical Chemistry (1985), 89(22), 4676-80.*

Abdallah et al. STN Accession No. 1983:611894 Document No. 99:211894, Abstract of Journal of the Chemical Society, Perkin Transactions 2: Physical Organic Chemistry (1972-1999) (1983),(8), 1243-9.*

Sokolov et al. Zhurnal Obshchei Khimii (1966), 2(6), 1088-92.*

Zyss et al. Journal of Chemical Physics (1984), 81(9), 4160-7.*

Jin et al. STN Document No. 117:151996, Abstract of Chemistry of Materials (1992), 4(5), 963-5.*

Elslager et al. STN Document No. 77:122113, Abstract of Journal of Medicinal Chemistry (1972), 15(8), 827-36.*

Ye et al. Bioorganic & Medicinal Chemistry Letters (2003), 13(19), 3361-3365.*

Yoshino et al. STN Accession No. 1990:523190, Abstract of Yoshino et al. Technology Reports of the Osaka University (1990), 40(1986-2003), 81-5.*

Dorwald F. A. (Side Reactions in Organic Synthesis, 2005, Wiley: VCH, Weinheim p. IX of Preface p. 1-15).*

Anastasiou et al. STN Accession No. 1994:605178, Document No. 121:205178, Abstract of Australian Journal of Chemistry (1994), 47(6), 1043-59.*

Prasmitskene et al., "The synthesis and study of the reactivity of p-[di-(2-chloropropyl)amino]phenylalkanoic acids," Bull.Acad.Sci. USSR. Chem. Sci. 3:576-579 (1969).

Kapil et al., "Phase I clinical trial of LGD-4033, a novel selective androgen receptor modulator (SARM)," 14th International Congress of Endocrinology, Kyoto, Japan, Mar. 26-30, 2010, 1 page [poster presentation].

Vadja et al., "LGD-4033 builds muscle and bone with reduced prostate activity and may be beneficial in age-related frailty," Gerontological Society of America 62nd Annual Scientific Meeting, Atlanta, Georgia, Nov. 18-22, 2009, 1 page [poster presentation].

Abela Medici et al., "Cytotoxic compounds. Part 21. Chloro-, methoxy-, and methoxycarbonylderivatives of (bis-2-chloroethylamino)-phenols and -anilines," Journal of the Chemical Society, Perkin Transactions 1, Organic and Bio-organic Chemistry, 20:2258-2263, (1977).

Anlezark et al., "Bioactivation of dinitrobenzamide mustards by an $E.$ $coli$ B nitroreductase," Biochemical Pharmacology, 50:609-618, (1995).

Ansel, H.C., Introduction to Pharmaceutical Dosage Forms, Fourth Edition, Lea and Febiger, Philadelphia, P.A., p. 126, (1985).

Bains and Tacke, "Silicon chemistry as a novel source of chemical diversity in drug design," Current Opinion in Drug Discovery and Development, 6(4):526-543, (2003).

Berger et al., "Interaction of glucocorticoid analogues with the human glucocorticoid receptor," Journal of Steroid Biochemistry and Molecular Biology, 41:733-748, (1992).

Derwent English abstract for WO 98/22432, published May 28, 1998 entitled: "New N-acyl-aminoacid aniline derivatives-useful as anti-androgens for treating cancer, masculinisation, hirutism etc.," Accession No. 8769118 [351].

Edwards et al., "Nonsteroidal androgen receptor agonists based on 4-(trifluoromethyl)-2H-pyrano[3,2-g]quinolin-2-one," Bioorganic Medicine and Chemistry Letters, 9(7):1003-1008, (1999).

Evans et al., "The steroid and thyroid hormone receptor superfamily," Science, 240:889-895, (1988).

Fingl et al., The Pharmacological Basis of Therapeutics, Ch. 1, Eds. Goodman and Gilman, Macmillan Publishing Co., New York, N.Y., pp. 1-46, (1975).

Gravatt et al., "DNA-directed alkylating agents. 6. Synthesis and antitumor activity of DNA minor groove-targeted aniline mustard analogues of pibenzimol (Hoechst 33258)," Journal of Medicinal Chemistry 37:4338-4345, (1994).

Hamann et al., "Synthesis and biological activity of a novel series of nonsteroidal, peripherally selective androgen receptor antagonists derived from 1,2-dihydropyridono[5,6-g]quinolines," Journal of Medicinal Chemistry, 41(4):623-639, (1998).

Higuchi et al., "4-Alkyl- and 3,4-dialkyl-1,2,3,4-tetrahydro-8-pyridono[5,6-g]quinolines potent, nonsteroidal androgen receptor agonists," Bioorganic Medicine and Chemistry Letters, 9(9):1335-1340, (1999).

Kong et al., "Effects of isosteric pyridone replacements in androgen receptor antagonists based on 1,2-dihydro- and 1,2,3,4-tetrahydro-2,2-dimethyl-6-trifluoromethyl-8-pyridono[5,6-g]quinolines," Bioorganic Medicine and Chemistry Letters, 10(5):411-414, (2000).

Michellys et al., "Design, synthesis, and structure-activity relationship studies of novel 6,7-locked-[7-(2-alkoxy-3,5-dialkylbenzene)-3-methylocta]-2,4,6-trienoic acids," Journal of Medicinal Chemistry, 46(19):4087-4103, (2003).

Niculescu-Duvaz et al., "Self-immolative nitrogen mustard prodrugs for suicide gene therapy," Journal of Medicinal Chemistry, 41:5297-5309, (1998).

Nogrady, T., *Medicinal Chemistry A Biochemical Approach*, Oxford University Press, New York, N.Y., pp. 388-392, (1985).

Palmer et al., "Hypoxia-selective antitumor agents. 3. Relationships between structure and cytotoxicity against cultured tumor cells for substituted N,N-bis(2-chloroethyl)anilines," Journal of Medicinal Chemistry, 33:112-121, (1990).

Palmer et al., "Hypoxia-selective antitumor agents. 5. Synthesis of water-soluble nitroaniline mustards with selective cytotoxicity for hypoxic mammalian cells," Journal of Medicinal Chemistry, 35:3214-3222, (1992).

Palmer et al., "Nitro analogues of chlorambucil as potential hypoxia-selective anti-tumour drugs," Anti-Cancer Drug Design, 5:337-349, (1990).

Panthananickal et al., "Structure-activity relationship of aniline mustards acting against B-16 melanoma in mice," Journal of Medicinal Chemistry, 22:1267-1269, (1979).

Pathirana et al., "Nonsteroidal human progesterone receptor modulators from the marine alga *Cymopolia barbatam*," Molecular Pharmacology, 47:630-635, (1995).

Pooley et al., "Discovery and preliminary SAR studies of a novel, nonsteroidal progesterone receptor antagonist pharmacophore," Journal of Medicinal Chemistry, 41:3461, (1998).

Popp, "Synthesis of potential antineoplastic agents X. Preparation and reactions of aldehydes related to benzaldehyde mustard," Journal of Medicinal Chemistry, 7:210-212, (1964).

Prasmickiene et al., "Synthesis and study of the reactivity of p-[bis(2-chloropropyl)amino]phenylalkanoic acids," Izvestiya Akademii Nauk SSSR, Seriya Khimicheskaya, 3:643-646, (1969).

Steinman et al., "1-Polyfluoroalkylbenzodiazepines; 1.," Journal of Medicinal Chemistry, 16:1354-1360, (1973).

Tacke and Zilch, "Sila-substitution—a useful strategy for drug design?" Endeavour, 10:191-197, (1986).

Turnbull et al., "The Reaction of 4-Substituted Aryl Isocyanates with NaBH4/Trifluoroacetic Acid (TFA)," Synthesis, 3:391-392, (1999).

Yin et al., "Key structural features of nonsteroidal ligands for binding and activation of the androgen receptor," Molecular Pharmacology, 63(1):211-223, (2003).

Zhi and Martinborough, "Selective androgen receptor modulators (SARMs)," Annual Reports in Medicinal Chemistry, 36:169-180, (2001).

Zhi et al., "Switching androgen receptor antagonists to agonists by modifying C-ring substituents on piperidino[3,2-g]quinolinone," Bioorganic and Medicinal Chemistry Letters, 9(7):1009-1012, (1999).

Zhi et al., "Nonsteroidal progesterone receptor antagonists based on 6-thiophenehydroquinolines," Bioorganic and Medicinal Chemistry Letters, 10:415-418, (2000).

Elslager et al., "Folate antagonists. 3. 2,4-Diamino-6-(heterocyclic)quinazolines, a novel class of antimetabolites with potent antimalarial and antibacterial activity," J. Med. Chem. 15(8):827-836 (1972).

Jin et al., "Poled, chromophore-functionalized polymeric nonlinear optical materials. Probing second harmonic generation temporal characteristics via site-selective crosslinking/hydrogen bonding," Chem. Materials 4(5):963-965 (1992).

Harrowven et al., "A new cascade radical reaction for the synthesis of biaryls and triaryls from benzyl iodoaryl ethers," Tet. Lett. 42:961-964 (2001).

Pan, H. And T. Fletcher, "Derivatives of fluorene. IX. 4-hydroxy-2-fluorenamine; new 3,4-benzocoumarin derivatives," J. Org. Chem. 25:1106-1109 (1960).

Prasmitskene et al., "The synthesis and study of the reactivity of p-di-(2-chloropropyl)aminolphenylalkanoic acids," Bull.Acad.Sci. USSR. Chem. Sci. 3:576-579 (1969).

Zhi et al., "5-aryl-1,2-dihydrochromeno[3,4-f]quinolines: a novel class of nonsteroidal human progesterone receptor agonists," J. Med. Chem. 41(3):291-302 (1998).

Zhi, L. and K. Marschke, "Novel class of non-steroidal progesterone receptor antagonists," Expert Opin. Ther. Patents 9(6):695-700 (1999).

\* cited by examiner

ANDROGEN RECEPTOR MODULATOR COMPOUNDS AND METHODS

RELATED APPLICATIONS

This application is the National Stage of International Application No. PCT/US2005/007867, filed 11 Mar. 2005, and priority is claimed herein under 35 U.S.C. 119 (e) to U.S. provisional patent application Ser. No. 60/552,690, filed Mar. 12, 2004, entitled "ANDROGEN RECEPTOR MODULATOR COMPOUNDS AND METHODS." The disclosure of the above-referenced provisional application is incorporated herein by reference in its entirety.

FIELD

Provided herein are compounds that bind to androgen receptors and/or modulate activity of androgen receptors, and methods for making and using such compounds. Also provided are compositions containing such compounds and methods for making and using such compositions.

BACKGROUND

Certain intracellular receptors (IRs) have been shown to regulate transcription of certain genes. See e.g., R. M. Evans, Science, 240, 889 (1988). Certain of such IRs are steroid receptors, such as androgen receptors, glucocorticoid receptors, estrogen receptors, mineralocorticoid receptors, and progesterone receptors. Gene regulation by such receptors typically involves binding of an IR by a ligand.

In certain instances, a ligand binds to an IR, forming a receptor/ligand complex. Such a receptor/ligand complex may then translocate to the nucleus of a cell, where it may bind to the DNA of one or more gene regulatory regions. Once bound to the DNA of a particular gene regulatory region, a receptor/ligand complex may modulate the production of the protein encoded by that particular gene. In certain instances, an androgen receptor/ligand complex regulates expression of certain proteins. In certain instances, an androgen receptor/ligand complex may interact directly with the DNA of a particular gene regulatory region. In certain instances, an androgen receptor/ligand complex may interact with other transcription factors, such as activator protein-1 (AP-1) or nuclear factor κB (NFκB). In certain instances, such interactions result in modulation of transcriptional activation.

SUMMARY

Compounds for use in compositions and methods for modulating the activity of androgen receptor are provided. In one embodiment, the compounds provided herein are agonists of androgen receptor. In another embodiment, the compounds provided herein are antagonists of androgen receptor.

In certain embodiments, provided herein are compounds having a structure selected from among Formula I, Formula II, Formula III, Formula IV, Formula V and Formula VI:

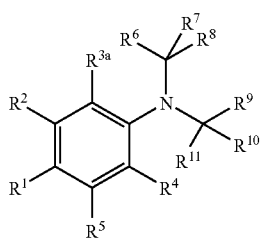
(I)

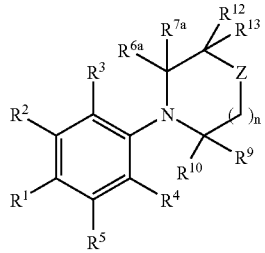
(II)

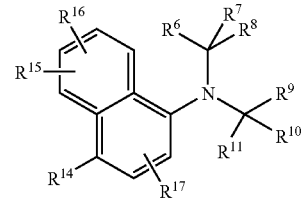
(III)

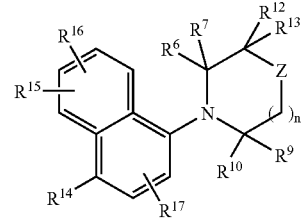
(IV)

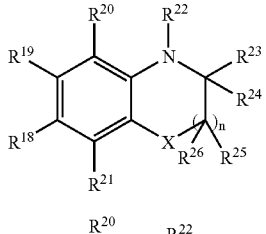
(V)

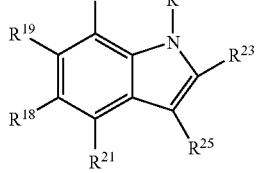
(VI)

wherein:

$R^1$ and $R^2$ are each independently selected from hydrogen, F, Cl, Br, I, $OR^A$, $SR^A$, $NO_2$, CN, an optionally substituted $C_1$-$C_4$ alkyl, an optionally substituted $C_1$-$C_4$ haloalkyl, an optionally substituted $C_1$-$C_4$ heteroalkyl, $COR^A$, $CO_2R^A$, $CONR^AR^B$, $SOR^A$, $SO_2R^A$, and $SO_2NR^AR^B$, $NHCOR^A$, and $NHCONR^AR^B$, provided that at least one of $R^1$ and $R^2$ is not hydrogen;

$R^3$, $R^{3a}$, $R^4$, and $R^5$ are each independently selected from hydrogen, F, Cl, $OR^A$, an optionally substituted $C_1$-$C_4$ alkyl, and an optionally substituted $C_1$-$C_4$ haloalkyl;

wherein if $R^1$ is $NO_2$ and $R^{3a}$ is F, then at least one of $R^2$ and $R^4$ and $R^5$ is not hydrogen; and wherein if $R^1$ is $NO_2$ and $R^3$ is F, then Z is not O;

$R^6$, $R^7$, $R^{10}$, and $R^{11}$ are each independently selected from hydrogen, an optionally substituted $C_1$-$C_6$ alkyl, an optionally substituted $C_1$-$C_6$ haloalkyl, an optionally substituted $C_1$-$C_6$ heteroalkyl, an optionally substituted $C_1$-$C_6$ heterohaloalkyl, an optionally substituted $C_2$-$C_6$ heterohaloalkenyl, an optionally substituted $C_2$-$C_6$ heterohaloalkynyl, an optionally substituted $C_2$-$C_6$ alkynyl, and an optionally substituted $C_2$-$C_6$ alkenyl;

$R^{6a}$ and $R^{7a}$ are each independently selected from hydrogen, an optionally substituted $C_1$-$C_6$ alkyl, an optionally substituted $C_1$-$C_6$ haloalkyl, an optionally substituted $C_1$-$C_6$ heteroalkyl, an optionally substituted $C_1$-$C_6$ heterohaloalkyl, an optionally substituted $C_2$-$C_6$ heterohaloalkenyl, an optionally substituted $C_2$-$C_6$ heterohaloalkynyl, an optionally substituted $C_2$-$C_6$ alkynyl, and an optionally substituted $C_2$-$C_6$ alkenyl; or $R^{6a}$ and $R^{7a}$ together form a carbonyl;

$R^8$ and $R^9$ are each independently selected from hydrogen, an optionally substituted $C_1$-$C_8$ alkyl, an optionally substituted $C_2$-$C_8$ alkenyl, an optionally substituted $C_1$-$C_8$ haloalkyl, an optionally substituted $C_2$-$C_8$ haloalkenyl, $C_1$-$C_8$ heteroalkyl, an optionally substituted $C_2$-$C_8$ heteroalkenyl, an optionally substituted $C_2$-$C_8$ alkynyl, an optionally substituted $C_2$-$C_8$ haloalkynyl, an optionally substituted $C_2$-$C_8$ heteroalkynyl, an optionally substituted $C_1$-$C_6$ heterohaloalkyl, an optionally substituted $C_1$-$C_6$ heterohaloalkenyl, an optionally substituted $C_1$-$C_6$ heterohaloalkynyl, an optionally substituted aryl, an optionally substituted heteroaryl, $CH(R^D)OR^A$, $CH(R^D)NR^AR^B$, $COR^A$, $CO_2R^A$ and $(CH_2)_mR^C$;

$R^{12}$ and $R^{13}$ are each independently selected from hydrogen, F, Cl, $OR^A$, $NR^AR^B$, $SR^A$, an optionally substituted $C_1$-$C_6$ alkyl, an optionally substituted $C_1$-$C_6$ haloalkyl, an optionally substituted $C_1$-$C_6$ heteroalkyl, an optionally substituted $C_2$-$C_6$ alkynyl, an optionally substituted $C_1$-$C_6$ heterohaloalkyl, an optionally substituted $C_1$-$C_6$ heterohaloalkenyl, an optionally substituted $C_1$-$C_6$ heterohaloalkynyl, an optionally substituted $C_2$-$C_6$ alkenyl, and $(CH_2)_mR^C$; $R^{14}$ and $R^{15}$ are each independently selected from hydrogen, F, Cl, Br, I, $OR^A$, $SR^A$, $NO_2$, CN, an optionally substituted $C_1$-$C_4$ alkyl, an optionally substituted $C_1$-$C_4$ haloalkyl, an optionally substituted $C_1$-$C_4$ heteroalkyl, $NHCOR^A$, $NHCONR^AR^B$, $COR^A$, $CO_2R^A$, $CONR^AR^B$, $SOR^A$, $SO_2R^A$, and $SO_2NR^AR^B$;

$R^{16}$ and $R^{17}$ are each independently selected from hydrogen, F, Cl, $OR^A$, an optionally substituted $C_1$-$C_4$ alkyl, and an optionally substituted $C_1$-$C_4$ haloalkyl;

$R^{18}$ and $R^{19}$ are each independently selected from hydrogen, F, Cl, Br, I, $OR^A$, $SR^A$, $NO_2$, CN, an optionally substituted $C_1$-$C_4$ alkyl, an optionally substituted $C_1$-$C_4$ haloalkyl, an optionally substituted $C_1$-$C_4$ heteroalkyl, $NHCOR^A$, $NHCONR^AR^B$, $COR^A$, $CO_2R^A$, $CONR^AR^B$, $SOR^A$, $SO_2R^A$, and $SO_2NR^AR^B$;

$R^{20}$ and $R^{21}$ are each independently selected from hydrogen, F, Cl, $OR^A$, an optionally substituted $C_1$-$C_4$ alkyl, and an optionally substituted $C_1$-$C_4$ haloalkyl; wherein if $R^{18}$ is $NO_2$ and X is O, then at least one of $R^{19}$, $R^{20}$, and $R^{21}$ is not hydrogen, and wherein if $R^{19}$ is $NO_2$ and X is C, then at least one of $R^{18}$, $R^{20}$, and $R^{21}$ is not hydrogen;

$R^{22}$ is selected from hydrogen, an optionally substituted $C_1$-$C_4$ alkyl, an optionally substituted $C_1$-$C_4$ haloalkyl, an optionally substituted $C_1$-$C_4$ heteroalkyl, $COR^6$, $CO_2R^A$, $CONR^AR^B$, $SO_2R^A$, an optionally substituted aryl, an optionally substituted heteroaryl, $CH_2CH(R^D)OR^A$, $CH_2CH(R^D)NR^AR^B$, and $(CH_2)_mR^C$, wherein the optionally substituted aryl or optionally substituted heteroaryl is optionally substituted with a substituent selected from F, Cl, Br, I, CN, $OR^A$, $NO_2$, $NR^AR^B$, $SR^A$, $SOR^A$, $SO_2R^A$, an optionally substituted $C_1$-$C_4$ alkyl, an optionally substituted $C_1$-$C_4$ haloalkyl, and an optionally substituted $C_1$-$C_4$ heteroalkyl;

$R^{23}$ and $R^{24}$ are each independently selected from hydrogen, an optionally substituted $C_1$-$C_8$ alkyl, an optionally substituted $C_2$-$C_8$ alkenyl, an optionally substituted $C_1$-$C_8$ haloalkyl, an optionally substituted $C_2$-$C_8$ haloalkenyl, an optionally substituted $C_1$-$C_8$ heteroalkyl, an optionally substituted $C_2$-$C_8$ heteroalkenyl, an optionally substituted $C_2$-$C_8$ alkynyl, an optionally substituted $C_2$-$C_8$ haloalkynyl, an optionally substituted $C_2$-$C_8$ heteroalkynyl, an optionally substituted aryl, an optionally substituted heteroaryl, $CH(R^D)OR^A$, $CH(R^D)NR^AR^B$, and $(CH_2)_mR^C$; or $R^{23}$ and $R^{24}$ together form a carbonyl group, provided that if $R^{18}$ is $NO_2$ and X is NH, then $R^{23}$ and $R^{24}$ do not together form a carbonyl group; or $R^{22}$ and $R^{23}$ are optionally linked to form a ring; or $R^{23}$ and $R^{25}$ are optionally linked to form a ring;

X is selected from O, S, $CR^AR^B$, $NR^D$, and a bond;

wherein if X is $CR^AR^B$ or a bond, then $R^{25}$ and $R^{26}$ are each independently selected from a halogen, $OR^A$, $NR^AR^B$, hydrogen, an optionally substituted $C_1$-$C_8$ alkyl, an optionally substituted $C_2$-$C_8$ alkenyl, an optionally substituted $C_1$-$C_8$ haloalkyl, an optionally substituted $C_2$-$C_8$ haloalkenyl, an optionally substituted $C_1$-$C_8$ heteroalkyl, an optionally substituted $C_2$-$C_8$ heteroalkenyl, an optionally substituted $C_2$-$C_8$ alkynyl, an optionally substituted $C_2$-$C_8$ haloalkynyl, an optionally substituted $C_2$-$C_8$ heteroalkynyl, an optionally substituted aryl, an optionally substituted heteroaryl, and $(CH_2)_mR^C$; or $R^{25}$ and $R^{26}$ together form a carbonyl group;

and wherein if X is O, S, or $NR^D$, then $R^{25}$ and $R^{26}$ are each independently selected from hydrogen, an optionally substituted $C_1$-$C_8$ alkyl, an optionally substituted $C_2$-$C_8$ alkenyl, an optionally substituted $C_1$-$C_8$ haloalkyl, an optionally substituted $C_2$-$C_8$ haloalkenyl, an optionally substituted $C_1$-$C_8$ heteroalkyl, an optionally substituted $C_2$-$C_8$ heteroalkenyl, an optionally substituted $C_2$-$C_8$ alkynyl, an optionally substituted $C_2$-$C_8$ haloalkynyl, an optionally substituted $C_2$-$C_8$ heteroalkynyl, an optionally substituted aryl, an optionally substituted heteroaryl, and $(CH_2)_mR^C$; or $R^{25}$ and $R^{26}$ together form a carbonyl group;

$R^{25}$ is selected from a halogen, $OR^A$, $NR^AR^B$, hydrogen, an optionally substituted $C_1$-$C_8$ alkyl, an optionally substituted $C_2$-$C_8$ alkenyl, an optionally substituted $C_1$-$C_8$ haloalkyl, an optionally substituted $C_2$-$C_8$ haloalkenyl, an optionally substituted $C_1$-$C_8$ heteroalkyl, an optionally substituted $C_2$-$C_8$ heteroalkenyl, an optionally substituted $C_2$-$C_8$ alkynyl, an optionally substituted $C_2$-$C_8$ haloalkynyl, an optionally substituted $C_2$-$C_8$ heterohaloalkenyl, an optionally substituted $C_2$-$C_8$ heterohaloalkynyl, an optionally substituted $C_2$-$C_8$ heteroalkynyl, an optionally substituted aryl, an optionally substituted heteroaryl, and $(CH_2)_mR^C$;

$R^A$ and $R^B$ are each independently selected from hydrogen, an optionally substituted $C_1$-$C_4$ alkyl, an optionally substituted $C_1$-$C_4$ haloalkyl, and an optionally substituted $C_1$-$C_4$ heteroalkyl;

$R^C$ is selected from an optionally substituted aryl and an optionally substituted heteroaryl that is optionally substituted with a substituent selected from F, Cl, Br, I, CN, $OR^A$, $NO_2$, $NR^AR^B$, $SR^A$, $SOR^A$, $SO_2R^A$, an optionally substituted $C_1$-$C_4$ alkyl, an optionally substituted $C_1$-$C_4$ haloalkyl, and an optionally substituted $C_1$-$C_4$ heteroalkyl;

$R^D$ is selected from hydrogen, an optionally substituted $C_1$-$C_4$ alkyl, an optionally substituted $C_1$-$C_4$ haloalkyl, and an optionally substituted $C_1$-$C_4$ heteroalkyl;

Z is selected from O, S, $CR^AR^B$, and $NR^D$;

n is 0, 1, or 2; and m is 1 or 2.

Also of interest are any pharmaceutically-acceptable derivatives, including salts, esters, enol ethers, enol esters, solvates, hydrates and prodrugs of the compounds described herein. Pharmaceutically-acceptable salts, include, but are not limited to, amine salts, such as but not limited to N,N'-dibenzylethylene-diamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethyl-benzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc, aluminum, and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates.

In certain embodiments, provided herein is a compound selected from: (a) N,N'-bis(2,2,2-trifluoroethyl)-3-methyl-4-nitroaniline; N,N'-bis(2,2,2-trifluoroethyl)-4-nitroaniline; 5-(2,2,2-trifluoroethyl)amino-2-bromobenzotrifluoride; 4-N, N'-bis(2,2,2-trifluoroethyl)amino-2-trifluoromethylbenzonitrile; (R)—N-4-nitrophenyl-5-(dimethyl-tert-butylsilyloxymethyl)-2-pyrrolidone; (R)—N-4-nitrophenyl-5-hydroxymethyl-2-pyrrolidone; (R)—N-(4-nitro-3-trifluoromethylphenyl)-2-dimethyl-tert-butylsilyloxymethylpyrrolidine; (R)—N-(4-nitro-3-trifluoromethylphenyl)-2-hydroxymethylpyrrolidine; (R)—N-(4-nitrophenyl)-2-hydroxymethylpyrrolidine; (R)—N-(3-Trifluoromethyl-4-nitrophenyl)-2-formylpyrrolidine; N-(3-Trifluoromethyl-4-nitrophenyl)-2-(R)-(1-(S)-hydroxy-2,2,2-trifluoroethyl)pyrrolidine; N-(3-Trifluoromethyl-4-nitrophenyl)-2-(R)-(1-(R)—hydroxy-2,2,2-trifluoroethyl) pyrrolidine; (S)—N-(4-nitrophenyl)-2-hydroxymethylpyrrolidine; N-(4-nitrophenyl)-2-(R)-(1-(S)-hydroxy-2,2,2-trifluoroethyl)pyrrolidine; N-(4-nitrophenyl)-2-(R)-(1-(R)-hydroxy-2,2,2-trifluoroethyl); N-(4-nitrophenyl)-2-(S)-(1-(S)-hydroxy-2,2,2-trifluoroethyl) pyrrolidine; and N-(4-nitrophenyl)-2-(S)-(1-(R)-hydroxy-2,2,2-trifluoroethyl)pyrrolidine; and (b) a pharmaceutically acceptable salt, ester, amide, or prodrug thereof.

In certain embodiments, provided herein are methods for identifying a compound that is capable of modulating an activity of an androgen receptor, by contacting a cell expressing an androgen receptor with a compound provided herein; and monitoring an effect of the compound upon the cell.

In certain embodiments, the provided herein are methods for identifying a compound that is capable of modulating an activity of an androgen receptor, by contacting a cell expressing an androgen receptor with a compound provided herein; and monitoring an effect of the compound upon the cell.

In certain embodiments, provided herein are methods for treating a patient by administering to the patient a compound provided herein. In certain embodiments, the methods provided herein are for maintenance of muscle strength and function (e.g., in the elderly); reversal or prevention of frailty or age-related functional decline ("ARFD") in the elderly (e.g., sarcopenia); treatment of catabolic side effects of glucocorticoids; prevention and/or treatment of reduced bone mass, density or growth (e.g., osteoporosis and osteopenia); treatment of chronic fatigue syndrome (CFS); chronic myalgia; treatment of acute fatigue syndrome and muscle loss following elective surgery (e.g., post-surgical rehabilitation); accelerating of wound healing; accelerating bone fracture repair (such as accelerating the recovery of hip fracture patients); accelerating healing of complicated fractures, e.g. distraction osteogenesis; in joint replacement; prevention of post-surgical adhesion formation; acceleration of tooth repair or growth; maintenance of sensory function (e.g., hearing, sight, olfaction and taste); treatment of periodontal disease; treatment of wasting secondary to fractures and wasting in connection with chronic obstructive pulmonary disease (COPD), chronic liver disease, AIDS, weightlessness, cancer cachexia, burn and trauma recovery, chronic catabolic state (e.g., coma), eating disorders (e.g., anorexia) and chemotherapy; treatment of cardiomyopathy; treatment of thrombocytopenia; treatment of growth retardation in connection with Crohn's disease; treatment of short bowel syndrome; treatment of irritable bowel syndrome; treatment of inflammatory bowel disease; treatment of Crohn's disease and ulcerative colitis; treatment of complications associated with transplantation; treatment of physiological short stature including growth hormone deficient children and short stature associated with chronic illness; treatment of obesity and growth retardation associated with obesity; treatment of anorexia (e.g., associated with cachexia or aging); treatment of hypercortisolism and Cushing's syndrome; Paget's disease; treatment of osteoarthritis; induction of pulsatile growth hormone release; treatment of osteochondrodysplasias; treatment of depression, nervousness, irritability and stress; treatment of reduced mental energy and low self-esteem (e.g., motivation/assertiveness); improvement of cognitive function (e.g., the treatment of dementia, including Alzheimer's disease and short term memory loss); treatment of catabolism in connection with pulmonary dysfunction and ventilator dependency; treatment of cardiac dysfunction (e.g., associated with valvular disease, myocardial infarction, cardiac hypertrophy or congestive heart failure); lowering blood pressure; protection against ventricular dysfunction or prevention of reperfusion events; treatment of adults in chronic dialysis; reversal or slowing of the catabolic state of aging; attenuation or reversal of protein catabolic responses following trauma (e.g., reversal of the catabolic state associated with surgery, congestive heart failure, cardiac myopathy, burns, cancer, COPD etc.); reducing cachexia and protein loss due to chronic illness such as cancer or AIDS; treatment of hyperinsulinemia including nesidioblastosis; treatment of immunosuppressed patients; treatment of wasting in connection with multiple sclerosis or other neurodegenerative disorders; promotion of myelin repair; maintenance of skin thickness; treatment of metabolic homeostasis and renal homeostasis (e.g., in the frail elderly); stimulation of osteoblasts, bone remodeling and cartilage growth; regulation of food intake; treatment of insulin resistance, including NIDDM, in mammals (e.g., humans); treatment of insulin resistance in the heart; improvement of sleep quality and correction of the relative hyposomatotropism of senescence due to high increase in REM sleep and a decrease in REM latency; treatment of hypothermia; treatment of congestive heart failure; treatment of lipodystrophy (e.g., in patients taking HIV or AIDS therapies such as protease inhibitors); treatment of muscular atrophy (e.g., due to physical inactivity, bed rest or reduced weight-bearing conditions); treatment of musculoskeletal impairment (e.g., in the elderly); improvement of the overall pulmonary function; treatment of sleep disorders; and the treatment of the catabolic state of prolonged critical illness; treatment of hirsutism, acne, seborrhea, androgenic alopecia, anemia, hyperpilosity, benign prostate hypertrophy, adenomas and neoplasies of the prostate (e.g., advanced metastatic prostate cancer) and malignant tumor cells containing the androgen receptor, such as is the case for breast, brain, skin, ovarian, bladder, lymphatic, liver and kidney cancers; cancers of the skin, pancreas, endometrium, lung and colon; osteosarcoma; hypercalcemia of malignancy; metastatic bone disease; treatment of spermatogenesis, endometriosis and polycystic ovary syndrome; counteracting preeclampsia, eclampsia of pregnancy and preterm labor;

treatment of premenstrual syndrome; treatment of vaginal dryness; age related decreased testosterone levels in men, male menopause, hypogonadism, male hormone replacement, male and female sexual dysfunction (e.g., erectile dysfunction, decreased sex drive, sexual well-being, decreased libido), male and female contraception, hair loss, Reaven's Syndrome and the enhancement of bone and muscle performance/strength.

In certain of such embodiments, the patient has a condition selected from acne, male-pattern baldness, wasting diseases, hirsutism, hypogonadism, osteoporoses, infertility, impotence, and cancer.

In certain embodiments, the methods provided herein are for stimulating hematopoiesis. In certain embodiments, the methods provided herein are for contraception. In certain embodiments, the methods provided herein are for improving athletic performance.

In certain embodiments, the compounds provided herein are selective androgen receptor modulators. In certain embodiments, the compounds provided herein are selective androgen receptor agonists. In certain embodiments, the compounds provided herein are selective androgen receptor antagonists. In certain embodiments, the compounds provided herein are androgen receptor partial agonists. In certain embodiments, the compounds provided herein are selective androgen receptor binding compounds.

In certain embodiments, provided herein are methods for modulating at least one activity of an androgen receptor. Certain of such methods are effected by contacting an androgen receptor with one or more compounds provided herein.

In certain embodiments, methods are provided for treating a patient by administering to the patient a compound provided herein. In certain embodiments, the methods provided herein are for treating a condition including, but not limited to, acne, male-pattern baldness, wasting diseases, hirsutism, hypogonadism, osteoporoses, infertility, impotence, and cancer.

Pharmaceutical compositions formulated for administration by an appropriate route and means containing effective concentrations of one or more of the compounds provided herein, or pharmaceutically acceptable derivatives thereof, that deliver amounts effective for the treatment, prevention, or amelioration of one or more symptoms of diseases or disorders that are modulated or otherwise affected by androgen receptor activity, or in which androgen receptor activity is implicated, are also provided. The effective amounts and concentrations are effective for ameliorating any of the symptoms of any of the diseases or disorders.

In certain embodiments, provided herein is a pharmaceutical composition containing: i) a physiologically acceptable carrier, diluent, and/or excipient; and ii) one or more compounds provided herein.

Articles of manufacture containing packaging material, within the packaging material a compound or composition, or pharmaceutically acceptable derivative thereof, which is effective for modulating the activity of androgen receptor, or for treatment, prevention or amelioration of one or more symptoms of androgen receptor mediated diseases or disorders, or diseases or disorders in which androgen receptor activity is implicated, and a label that indicates that the compound or composition, or pharmaceutically acceptable derivative thereof, is used for modulating the activity of androgen receptor, or for treatment, prevention or amelioration of one or more symptoms of androgen receptor mediated diseases or disorders, or diseases or disorders in which androgen receptor activity is implicated, are provided.

DETAILED DESCRIPTION

A. Definitions

Unless defined otherwise, all technical and scientific terms used herein have the same meaning as is commonly understood by one of skill in the art to which the claimed subject matter belongs. All patents, patent applications, and published materials referred to throughout the entire disclosure herein, unless noted otherwise, are incorporated by reference in their entirety. In the event that there are a plurality of definitions for terms herein, those in this section prevail. Where reference is made to a URL or other such identifier or address, it is understood that such identifiers can change and particular information on the internet can come and go, but equivalent information can be found by searching the internet. Reference thereto evidences the availability and public dissemination of such information.

It is to be understood that both the foregoing general description and the following detailed description are exemplary and explanatory only and are not restrictive of the subject matter claimed. In this application, the use of the singular includes the plural unless specifically stated otherwise. In this application, the use of "or" means "and/or" unless stated otherwise. Furthermore, use of the term "including" as well as other forms, such as "includes," and "included," is not limiting.

The section headings used herein are for organizational purposes only and are not to be construed as limiting the subject matter described. All documents, or portions of documents, cited in the application including, but not limited to, patents, patent applications, articles, books, manuals, and treatises are hereby expressly incorporated by reference in their entirety for any purpose.

Unless specific definitions are provided, the nomenclatures utilized in connection with, and the laboratory procedures and techniques of, analytical chemistry, synthetic organic chemistry, and medicinal and pharmaceutical chemistry described herein are those known in the art. Standard techniques may be used for chemical syntheses, chemical analyses, pharmaceutical preparation, formulation, and delivery, and treatment of patients. Standard techniques may be used for recombinant DNA, oligonucleotide synthesis, and tissue culture and transformation (e.g., electroporation, lipofection). Reactions and purification techniques may be performed e.g., using kits according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)), which is incorporated herein by reference for any purpose.

As used herein, the term "selective binding compound" refers to a compound that selectively binds to any portion of one or more target receptors.

As used herein, the term "selective androgen receptor binding compound" refers to a compound that selectively binds to any portion of an androgen receptor.

As used herein, the following terms are defined with the following meanings, unless explicitly stated otherwise.

As used herein, the term "selective binding compound" refers to a compound that selectively binds to any portion of one or more target receptors.

As used herein, the term "selective androgen receptor binding compound" refers to a compound that selectively binds to any portion of an androgen receptor.

As used herein, the term "selectively binds" refers to the ability of a selective binding compound to bind to a target receptor with greater affinity than it binds to a non-target receptor. In certain embodiments, specific binding refers to binding to a target with an affinity that is at least 10, 50, 100, 250, 500, 1000 or more times greater than the affinity for a non-target.

As used herein, the term "target receptor" refers to a molecule or a portion of a receptor capable of being bound by a selective binding compound. In certain embodiments, a target receptor is an androgen receptor.

As used herein, the terms "treating" or "treatment" encompass either or both responsive and prophylaxis measures, e.g., designed to inhibit or delay the onset of the disease or disorder, achieve a full or partial reduction of the symptoms or disease state, and/or to alleviate, ameliorate, lessen, or cure the disease or disorder and/or its symptoms. Treatment also encompasses any pharmaceutical use of the compositions herein, such as use for treating gluococorticoid mediated diseases or disorders.

As used herein, amelioration of the symptoms of a particular disorder by administration of a particular compound or pharmaceutical composition refers to any lessening, whether permanent or temporary, lasting or transient that can be attributed to or associated with administration of the composition.

As used herein, the term "modulator" refers to a compound that alters an activity of a molecule. For example, a modulator can cause an increase or decrease in the magnitude of a certain activity of a molecule compared to the magnitude of the activity in the absence of the modulator. In certain embodiments, a modulator is an inhibitor, which decreases the magnitude of one or more activities of a molecule. In certain embodiments, an inhibitor completely prevents one or more activities of a molecule. In certain embodiments, a modulator is an activator, which increases the magnitude of at least one activity of a molecule. In certain embodiments the presence of a modulator results in an activity that does not occur in the absence of the modulator.

As used herein, the term "selective modulator" refers to a compound that selectively modulates a target activity.

As used herein, the term "selective androgen receptor modulator" refers to a compound that selectively modulates at least one activity associated with an androgen receptor.

As used herein, the term "selectively modulates" refers to the ability of a selective modulator to modulate a target activity to a greater extent than it modulates a non-target activity. In certain embodiments the target activity is selectively modulated by, for example about 2 fold up to more than about 500 folds, in some embodiments, about 2, 5, 10, 50, 100, 150, 200, 250, 300, 350, 400, 450 or more than 500 folds.

As used herein, the term "target activity" refers to a biological activity capable of being modulated by a selective modulator. Certain exemplary target activities include, but are not limited to, binding affinity, signal transduction, enzymatic activity, tumor growth, and inflammation or inflammation-related processes.

As used herein, the term "receptor mediated activity" refers any biological activity that results, either directly or indirectly, from binding of a ligand to a receptor.

As used herein, the term "agonist" refers to a compound, the presence of which results in a biological activity of a receptor that is the same as the biological activity resulting from the presence of a naturally occurring ligand for the receptor.

As used herein, the term "partial agonist" refers to a compound the presence of which results in a biological activity of a receptor that is of the same type as that resulting from the presence of a naturally occurring ligand for the receptor, but of a lower magnitude.

As used herein, the term "antagonist" refers to a compound, the presence of which results in a decrease in the magnitude of a biological activity of a receptor. In certain embodiments, the presence of an antagonist results in complete inhibition of a biological activity of a receptor.

As used herein, the $IC_{50}$ refers to an amount, concentration or dosage of a particular test compound that achieves a 50% inhibition of a maximal response, such as modulation of androgen receptor activity, in an assay that measures such response.

As used herein, $EC_{50}$ refers to a dosage, concentration or amount of a particular test compound that elicits a dose-dependent response at 50% of maximal expression of a particular response that is induced, provoked or potentiated by the particular test compound.

As used herein, $C_1$-$C_x$ includes $C_1$-$C_2$, $C_1$-$C_3$ ... $C_1$-$C_x$.

As used herein, the term "alkyl" refers to an aliphatic hydrocarbon group. An alkyl group can be a "saturated alkyl," which means that it does not contain any alkene or alkyne groups. An alkyl group can be an "unsaturated alkyl," which means that it contains at least one alkene or alkyne group. An alkyl, whether saturated or unsaturated, can be branched, straight chain, or cyclic.

In certain embodiments, an alkyl contains 1 to 20 carbon atoms (whenever it appears herein, a numerical range such as "1 to 20" refers to each integer in the given range; e.g., "1 to 20 carbon atoms" means that an alkyl group can contain only 1 carbon atom, 2 carbon atoms, 3 carbon atoms, etc., up to and including 20 carbon atoms, although the term "alkyl" also includes instances where no numerical range of carbon atoms is designated).

As used herein, the term "lower alkyl" refers to an alkyl containing 1 to 5 carbon atoms. The term "medium alkyl" refers to an alkyl containing 5 to 10 carbon atoms. An alkyl can be designated as "$C_1$-$C_4$ alkyl" or similar designations. By way of example only, "$C_1$-$C_4$ alkyl" indicates an alkyl having one, two, three, or four carbon atoms, i.e., the alkyl is selected from among methyl, ethyl, propyl, iso-propyl, n-butyl, iso-butyl, sec-butyl, and t-butyl. Thus $C_1$-$C_4$ includes $C_1$-$C_2$ and $C_1$-$C_3$ alkyl. Alkyls can be substituted or unsubstituted. Alkyls include, but are not limited to, methyl, ethyl, propyl, isopropyl, butyl, isobutyl, tertiary butyl, pentyl, hexyl, ethenyl, propenyl, butenyl, cyclopropyl, cyclobutyl, cyclopentyl, cyclohexyl, and the like, each of which can be optionally substituted.

As used herein, the term "alkenyl" refers to an alkyl group containing at least one carbon-carbon double bond.

As used herein, the term "alkynyl" refers to an alkyl group containing at least one carbon-carbon triple bond.

As used herein, the term "haloalkyl" refers to an alkyl in which at least one hydrogen atom is replaced with a halogen atom. In certain of the embodiments in which two or more hydrogen atom are replaced with halogen atoms, the halogen atoms are all the same as one another. In certain of such embodiments, the halogen atoms are not all the same as one another.

As used herein, the term "heteroalkyl" refers to a group containing an alkyl and one or more heteroatoms. Certain heteroalkyls are acylalkyls, in which the one or more heteroatoms are within an alkyl chain. Examples of heteroalkyls include, but are not limited to, $CH_3C(=O)CH_2-$, $CH_3C(=O)CH_2CH_2-$, $CH_3CH_2C(=O)CH_2CH_2-$, $CH_3C(=O)CH_2CH_2CH_2-$, $CH_3OCH_2CH_2-$, $CH_3NHCH_2-$, and the like.

As used herein, the term "heterohaloalkyl" refers to a heteroalkyl in which at least one hydrogen atom is replaced with a halogen atom.

As used herein, the term "carbocycle" refers to a group containing a covalently closed ring, wherein each of the atoms forming the ring is a carbon atom. Carbocylic rings can be formed by three, four, five, six, seven, eight, nine, or more than nine carbon atoms. Carbocycles can be optionally substituted.

As used herein, the term "heterocycle" refers to a group containing a covalently closed ring wherein at least one atom forming the ring is a heteroatom. Heterocyclic rings can be formed by three, four, five, six, seven, eight, nine, or more than nine atoms. Heterocycles can be optionally substituted. Binding to a heterocycle can be at a heteroatom or via a carbon atom. For example, binding for benzo-fused derivatives, can be via a carbon of the benzenoid ring.

As used herein, the term "heteroatom" refers to an atom other than carbon or hydrogen. Heteroatoms are typically independently selected from oxygen, sulfur, nitrogen, and phosphorus, but are not limited to those atoms. In embodiments in which two or more heteroatoms are present, the two or more heteroatoms can all be the same as one another, or some or all of the two or more heteroatoms can each be different from the others.

As used herein, the term "aromatic" refers to a group containing a covalently closed ring having a delocalized π-electron system. Aromatic rings can be formed by three, four, five, six, seven, eight, nine, or more than nine atoms. Aromatics can be optionally substituted. Examples of aromatic groups include, but are not limited to phenyl, naphthalenyl, phenanthrenyl, anthracenyl, tetralinyl, fluorenyl, indenyl, and indanyl. The term aromatic includes, for example, benzenoid groups, connected via one of the ring-forming carbon atoms, and optionally carrying one or more substituents selected from an aryl, a heteroaryl, a cycloalkyl, a non-aromatic heterocycle, a halo, a hydroxy, an amino, a cyano, a nitro, an alkylamido, an acyl, a $C_1$-$C_6$alkoxy, a $C_1$-$C_6$alkyl, a hydroxy $C_1$-$C_6$alkyl, an amino$C_1$-$C_6$alkyl, a $C_1$-$C_6$alkylamino, an alkylsulfenyl, an alkylsulfinyl, an alkylsulfonyl, a sulfamoyl, or a trifluoromethyl. In certain embodiments, an aromatic group is substituted at one or more of the para, meta, and/or ortho positions. Examples of aromatic groups containing substitutions include, but are not limited to, phenyl, 3-halophenyl, 4-halophenyl, 3-hydroxyphenyl, 4-hydroxyphenyl, 3-aminophenyl, 4-aminophenyl, 3-methylphenyl, 4-methylphenyl, 3-methoxyphenyl, 4-methoxyphenyl, 4-trifluoromethoxyphenyl, 3-cyanophenyl, 4-cyanophenyl, dimethylphenyl, naphthyl, hydroxynaphthyl, hydroxymethylphenyl, (trifluoromethyl)phenyl, alkoxyphenyl, 4-morpholin-4-ylphenyl, 4-pyrrolidin-1-ylphenyl, 4-pyrazolylphenyl, 4-triazolylphenyl, and 4-(2-oxopyrrolidin-1-yl)phenyl.

As used herein, the term "aryl" refers to an aromatic group wherein each of the atoms forming the ring is a carbon atom. Aryl rings can be formed by three, four, five, six, seven, eight, nine, or more than nine carbon atoms. Aryl groups can be optionally substituted.

As used herein, the term "heteroaryl" refers to an aromatic group in which at least one atom forming the aromatic ring is a heteroatom. Heteroaryl rings can be formed by three, four, five, six, seven, eight, nine and more than nine atoms. Heteroaryl groups can be optionally substituted. Examples of heteroaryl groups include, but are not limited to, aromatic $C_3$-$C_8$ heterocyclic groups containing one oxygen or sulfur atom or up to four nitrogen atoms, or a combination of one oxygen or sulfur atom and up to two nitrogen atoms, and their substituted as well as benzo- and pyrido-fused derivatives, for example, connected via one of the ring-forming carbon atoms. In certain embodiments, heteroaryl groups are optionally substituted with one or more substituents, independently selected from halo, hydroxy, amino, cyano, nitro, alkylamido, acyl, $C_1$-$C_6$-alkoxy, $C_1$-$C_6$-alkyl, hydroxy$C_1$-$C_6$-alkyl, amino$C_1$-$C_6$-alkyl, $C_1$-$C_6$-alkylamino, alkylsulfenyl, alkylsulfinyl, alkylsulfonyl, sulfamoyl, or trifluoromethyl. As in all examples herein $C_1$-$C_x$ includes $C_1$-$C_2$, $C_1$-$C_3$ . . . $C_1$-$C_x$. Examples of heteroaryl groups include, but are not limited to, unsubstituted and mono- or di-substituted derivatives of furan, benzofuran, thiophene, benzothiophene, pyrrole, pyridine, indole, oxazole, benzoxazole, isoxazole, benzisoxazole, thiazole, benzothiazole, isothiazole, imidazole, benzimidazole, pyrazole, indazole, tetrazole, quinoline, isoquinoline, pyridazine, pyrimidine, purine and pyrazine, furazan, 1,2,3-oxadiazole, 1,2,3-thiadiazole, 1,2,4-thiadiazole, triazole, benzotriazole, pteridine, phenoxazole, oxadiazole, benzopyrazole, quinolizine, cinnoline, phthalazine, quinazoline, and quinoxaline. In some embodiments, the substituents are halo, hydroxy, cyano, O—$C_1$-$C_6$-alkyl, $C_1$-$C_6$-alkyl, hydroxy-$C_1$-$C_6$-alkyl, and amino-$C_1$-$C_6$-alkyl.

As used herein, the term "non-aromatic ring" refers to a group containing a covalently closed ring that does not have a delocalized π-electron system.

As used herein, the term "cycloalkyl" refers to a group containing a non-aromatic ring wherein each of the atoms forming the ring is a carbon atom. Cycloalkyl rings can be formed by three, four, five, six, seven, eight, nine, or more than nine carbon atoms. Cycloalkyls can be optionally substituted. In certain embodiments, a cycloalkyl contains one or more unsaturated bonds. Examples of cycloalkyls include, but are not limited to, cyclopropane, cyclobutane, cyclopentane, cyclopentene, cyclopentadiene, cyclohexane, cyclohexene, 1,3-cyclohexadiene, 1,4-cyclohexadiene, cycloheptane, and cycloheptene.

As used herein, the term "non-aromatic heterocycle" refers to a group containing a non-aromatic ring wherein one or more atoms forming the ring is a heteroatom. Non-aromatic heterocyclic rings can be formed by three, four, five, six, seven, eight, nine, or more than nine atoms. Non-aromatic heterocycles can be optionally substituted. In certain embodiments, non-aromatic heterocycles contain one or more carbonyl or thiocarbonyl groups such as, for example, oxo- and thio-containing groups. Examples of non-aromatic heterocycles include, but are not limited to, lactams, lactones, cyclic imides, cyclic thioimides, cyclic carbamates, tetrahydrothiopyran, 4H-pyran, tetrahydropyran, piperidine, 1,3-dioxin, 1,3-dioxane, 1,4-dioxin, 1,4-dioxane, piperazine, 1,3-oxathiane, 1,4-oxathiin, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, morpholine, trioxane, hexahydro-1,3,5-triazine, tetrahydrothiophene, tetrahydrofuran, pyrroline, pyrrolidine, pyrrolidone, pyrrolidione, pyrazoline, pyrazolidine, imidazoline, imidazolidine, 1,3-dioxole, 1,3-dioxolane, 1,3-dithiole, 1,3-dithiolane, isoxazoline, isoxazolidine, oxazoline, oxazolidine, oxazolidinone, thiazoline, thiazolidine, and 1,3-oxathiolane.

As used herein, the term "arylalkyl" refers to a group containing an aryl group bound to an alkyl group.

As used herein, the term "carbocycloalkyl" refers to a group containing a carbocyclic cycloalkyl ring. Carbocycloalkyl rings can be formed by three, four, five, six, seven, eight, nine, or more than nine carbon atoms. Carbocycloalkyl groups can be optionally substituted.

As used herein, the term "ring" refers to any covalently closed structure. Rings include, for example, carbocycles (e.g., aryls and cycloalkyls), heterocycles (e.g., heteroaryls and non-aromatic heterocycles), aromatics (e.g., aryls and heteroaryls), and non-aromatics (e.g., cycloalkyls and non-aromatic heterocycles). Rings can be optionally substituted. Rings can form part of a ring system.

As used herein, the term "ring system" refers to two or more rings, wherein two or more of the rings are fused. The term "fused" refers to structures in which two or more rings share one or more bonds.

As used herein, the substituent "R" appearing by itself and without a number designation refers to a substituent selected from alkyl, cycloalkyl, aryl, heteroaryl (bonded through a ring carbon) and non-aromatic heterocycle (bonded through a ring carbon).

As used herein, the term "O-carboxy" refers to a group of formula RC(=O)O—.

As used herein, the term "C-carboxy" refers to a group of formula —C(=O)OR.

As used herein, the term "acetyl" refers to a group of formula —C(=O)CH$_3$.

As used herein, the term "trihalomethanesulfonyl" refers to a group of formula X$_3$CS(=O)$_2$— where X is a halogen.

As used herein, the term "cyano" refers to a group of formula —CN.

As used herein, the term "isocyanato" refers to a group of formula —NCO.

As used herein, the term "thiocyanato" refers to a group of formula —CNS.

As used herein, the term "isothiocyanato" refers to a group of formula —NCS.

As used herein, the term "sulfinyl" refers to a group of formula —S(=O)—R.

As used herein, the term "S-sulfonamido" refers to a group of formula —S(=O)$_2$NR$_2$.

As used herein, the term "N-sulfonamido" refers to a group of formula RS(=O)$_2$NH—.

As used herein, the term "trihalomethanesulfonamido" refers to a group of formula X$_3$CS(=O)$_2$NR—.

As used herein, the term "O-carbamyl" refers to a group of formula —OC(=O)—NR$_2$.

As used herein, the term "N-carbamyl" refers to a group of formula ROC(=O)NH—.

As used herein, the term "O-thiocarbamyl" refers to a group of formula —OC(=S)—NR$_2$.

As used herein, the term "N-thiocarbamyl" refers to a group of formula ROC(=S)NH—.

As used herein, the term "C-amido" refers to a group of formula —C(=O)—NR$_2$.

As used herein, the term "N-amido" refers to a group of formula RC(=O)NH—.

As used herein, the term "ester" refers to a chemical moiety with the formula —(R)$_n$—COOR', where R and R' are independently selected from alkyl, cycloalkyl, aryl, heteroaryl (bonded through a ring carbon) and non-aromatic heterocycle (bonded through a ring carbon), where n is 0 or 1.

As used herein, the term "amide" refers to a chemical moiety with formula —(R)$_n$—C(O)NHR' or —(R)$_n$—NHC(O)R', where R and R' are independently selected from alkyl, cycloalkyl, aryl, heteroaryl (bonded through a ring carbon) and heteroalicyclic (bonded through a ring carbon), where n is 0 or 1. In certain embodiments, an amide can be an amino acid or a peptide.

As used herein, the terms "amine," "hydroxy," and "carboxyl" include such groups that have been esterified or amidified. Procedures and specific groups used to achieve esterification and amidification are known to those of skill in the art and can readily be found in reference sources such as Greene and Wuts, Protective Groups in Organic Synthesis, 3$^{rd}$ Ed., John Wiley & Sons, New York, N.Y., 1999, which is incorporated herein in its entirety.

Throughout the specification, groups and substituents thereof can be chosen by one skilled in the field to provide stable moieties and compounds.

Unless otherwise indicated, the term "optionally substituted," refers to a group in which none, one, or more than one of the hydrogen atoms has been replaced with one or more group(s) individually and independently selected from: cycloalkyl, aryl, heteroaryl, non-aromatic heterocycle, hydroxy, alkoxy, aryloxy, mercapto, alkylthio, arylthio, cyano, halo, carbonyl, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, trihalomethanesulfonyl, and amino, including mono and di-substituted amino groups, and the protected derivatives of amino groups. Such protective derivatives (and protecting groups that can form such protective derivatives) are known to those of skill in the art and can be found in references such as Greene and Wuts, above. In embodiments in which two or more hydrogen atoms have been substituted, the substituent groups can together form a ring.

As used herein, the term "carrier" refers to a compound that facilitates the incorporation of another compound into cells or tissues. For example, dimethyl sulfoxide (DMSO) is a commonly used carrier for improving incorporation of certain organic compounds into cells or tissues.

As used herein, the term "pharmaceutical agent" refers to a chemical compound or composition capable of inducing a desired therapeutic effect in a patient. In certain embodiments, a pharmaceutical agent contains an active agent, which is the agent that induces the desired therapeutic effect. In certain embodiments, a pharmaceutical agent is a prodrug. In certain embodiments, a pharmaceutical agent contains inactive ingredients such as carriers, excipients, and the like.

As used herein, the term "therapeutically effective amount" refers to an amount of a pharmaceutical agent sufficient to achieve a desired therapeutic effect.

As used herein, a "prodrug" refers to a pharmaceutical agent that is converted from a less active form into a corresponding more active form in vivo. A prodrug is a compound that, upon in vivo administration, is metabolized by one or more steps or processes or otherwise converted to the biologically, pharmaceutically or therapeutically active form of the compound. To produce a prodrug, the pharmaceutically active compound is modified such that the active compound will be regenerated by metabolic processes. The prodrug can be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) *Medicinal Chemistry A Biochemical Approach*, Oxford University Press, New York, pages 388-392).

As used herein, the term "pharmaceutically acceptable" refers to a formulation of a compound that does not significantly abrogate the biological activity, a pharmacological activity and/or other properties of the compound when the formulated compound is administered to a patient. In certain embodiments, a pharmaceutically acceptable formulation does not cause significant irritation to a patient.

As used herein, pharmaceutically acceptable derivatives of a compound include salts, esters, enol ethers, enol esters, acetals, ketals, orthoesters, hemiacetals, hemiketals, acids, bases, solvates, hydrates or prodrugs thereof. Such derivatives can be readily prepared by those of skill in this art using known methods for such derivatization. The compounds produced can be administered to animals or humans without substantial toxic effects and either are pharmaceutically active or are prodrugs. Pharmaceutically acceptable salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethylbenzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates. Pharmaceutically acceptable esters include, but are not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids. Pharmaceutically acceptable enol ethers include, but are not limited to, derivatives of formula C=C(OR) where R is hydrogen, alkyl, alkenyl, alkynyl, aryl, heteroaryl, aralkyl, heteroaralkyl, cycloalkyl or heterocyclyl. Pharmaceutically acceptable enol esters include, but are not limited to, derivatives of formula C=C(OC(O)R) where R is hydrogen, alkyl, alkenyl, alkynyl, aryl, heteroaryl, aralkyl, heteroaralkyl, cycloalkyl or heterocyclyl. Pharmaceutically acceptable solvates and hydrates are complexes of a compound with one or more solvent or water molecules, or 1 to about 100, or 1 to about 10, or one to about 2, 3 or 4, solvent or water molecules.

It is to be understood that the compounds provided herein can contain chiral centers. Such chiral centers can be of either the (R) or (S) configuration, or can be a mixture thereof. Thus, the compounds provided herein can be enantiomerically pure, or be stereoisomeric or diastereomeric mixtures.

As used herein, substantially pure means sufficiently homogeneous to appear free of readily detectable impurities as determined by standard methods of analysis, such as thin layer chromatography (TLC), gel electrophoresis, high performance liquid chromatography (HPLC) and mass spectrometry (MS), used by those of skill in the art to assess such purity, or sufficiently pure such that further purification would not detectably alter the physical and chemical properties, such as enzymatic and biological activities, of the substance. Thus, substantially pure object species (e.g., compound) is the predominant species present (i.e., on a molar basis it is more abundant than any other individual species in the composition). In certain embodiments, a substantially purified fraction is a composition wherein the object species contains at least about 50 percent (on a molar basis) of all species present. In certain embodiments, a substantially pure composition will contain more than about 50%, 60%, 70%, 80%, 85%, 90%, 95%, or 99% of all species present in the composition. In certain embodiments, a substantially pure composition will contain more than about 80%, 85%, 90%, 95%, or 99% of all species present in the composition. Methods for purification of the compounds to produce substantially chemically pure compounds are known to those of skill in the art. A substantially chemically pure compound can, however, be a mixture of stereoisomers. In such instances, further purification might increase the specific activity of the compound. The instant disclosure is meant to include all such possible isomers, as well as, their racemic and optically pure forms. Optically active (+) and (−), (R)- and (S)-, or (D)- and (L)-isomers can be prepared using chiral synthons or chiral reagents, or resolved using conventional techniques, such as reverse phase HPLC. When the compounds described herein contain olefinic double bonds or other centers of geometric asymmetry, and unless specified otherwise, it is intended that the compounds include both E and Z geometric isomers. Likewise, all tautomeric forms are also intended to be included.

As used herein, the term "co-administer" refers to administering more than one pharmaceutical agent to a patient. In certain embodiments, co-administered pharmaceutical agents are administered together in a single dosage unit. In certain embodiments, co-administered pharmaceutical agents are administered separately. In certain embodiments, co-administered pharmaceutical agents are administered at the same time. In certain embodiments, co-administered pharmaceutical agents are administered at different times.

As used herein "subject" is an animal, typically a mammal, including human.

As used herein, the term "patient" includes human and animal subjects.

As used herein, the term "tissue-selective" refers to the ability of a compound to modulate a biological activity in one tissue to a greater or lesser degree than it modulates a biological activity in another tissue. The biological activities in the different tissues can be the same or they can be different. The biological activities in the different tissues can be mediated by the same type of target receptor. For example, in certain embodiments, a tissue-selective compound can modulate an androgen receptor mediated biological activity in one tissue and fail to modulate, or modulate to a lesser degree, an androgen receptor mediated biological activity in another tissue type.

As used herein, the term "monitoring" refers to observing an effect or absence of any effect. In certain embodiments, one monitors cells after contacting those cells with a compound provided herein. Examples of effects that can be monitored include, but are not limited to, changes in cell phenotype, cell proliferation, androgen receptor activity, or the interaction between an androgen receptor and a natural binding partner.

As used herein, the term "cell phenotype" refers to physical or biological characteristics. Examples of characteristics that constitute phenotype included, but are not limited to, cell size, cell proliferation, cell differentiation, cell survival, apoptosis (cell death), or the utilization of a metabolic nutrient (e.g., glucose uptake). Certain changes or the absence of changes in cell phenotype are readily monitored using techniques known in the art.

As used herein, the term "cell proliferation" refers to the rate at which cells divide. The number of cells growing in a vessel can be quantified by a person skilled in the art (e.g., by counting cells in a defined area using a light microscope, or by using laboratory apparatus that measure the density of cells in an appropriate medium). One skilled in that art can calculate cell proliferation by determining the number of cells at two or more times.

As used herein, the term "contacting" refers to bringing two or more materials into close enough proximity that they can interact. In certain embodiments, contacting can be accomplished in a vessel such as a test tube, a petri dish, or the like. In certain embodiments, contacting can be performed in the presence of additional materials. In certain embodiments, contacting can be performed in the presence of cells. In certain of such embodiments, one or more of the materials that are being contacted can be inside a cell. Cells can be alive or can be dead. Cells can or cannot be intact.

B. Compounds

Certain compounds that bind to androgen receptors and/or modulate an activity of such receptors play a role in health (e.g., normal growth, development, and/or absence of disease). In certain embodiments, selective androgen receptor modulators and/or binding compounds are useful for treating any of a variety of diseases or conditions.

Certain compounds have been previously described as receptor modulators or as possible receptor modulators. See e.g., U.S. Pat. Nos. 6,462,038, 5,693,646; 6,380,207; 6,506,766; 5,688,810; 5,696,133; 6,569,896, 6,673,799; 4,636,505; 4,097,578; 3,847,988; U.S. application Ser. No. 10/209,461 (Pub. No. US 2003/0055094); WO 01/27086; WO 02/22585; Zhi, et. al. *Bioorganic & Medicinal Chemistry Letters* 2000, 10, 415-418; Pooley, et. al., *J. Med. Chem.* 1998, 41, 3461; Hamann, et al. *J. Med. Chem.* 1998, 41(4), 623; and Yin, et al., *Molecular Pharmacology*, 2003, 63 (1), 211-223 the entire disclosures of which are incorporated in their entirety.

In certain embodiments, the compounds provided herein are selective androgen receptor modulators. In certain embodiments, the compounds provided herein are selective androgen receptor binding agents. In certain embodiments, provided herein are methods of making and methods of using androgen receptor modulators and/or androgen binding agents provided herein. In certain embodiments, selective androgen modulators are agonists, partial agonists, and/or antagonists for the androgen receptor.

In certain embodiments, the compounds provided herein have a structure selected from Formula I, Formula II, Formula III, Formula IV, Formula V, and Formula VI:

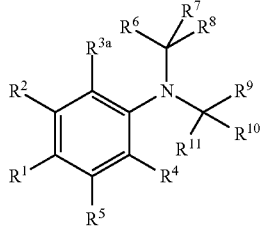

(I)

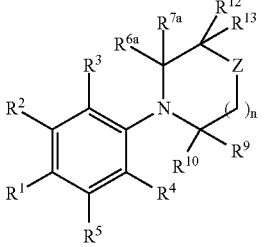

(II)

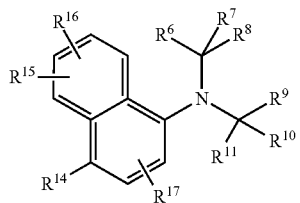

(III)

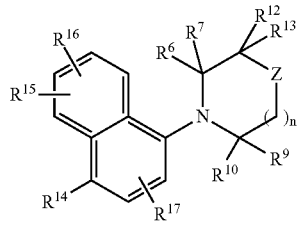

(IV)

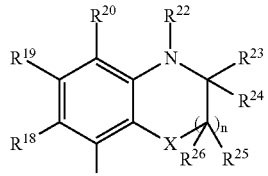

(V)

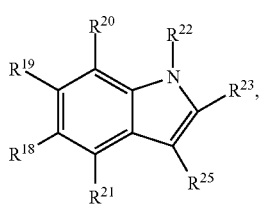

(VI)

wherein:

$R^1$ and $R^2$ are each independently selected from hydrogen, F, Cl, Br, I, $OR^A$, $SR^A$, $NO_2$, CN, an optionally substituted $C_1$-$C_4$ alkyl, an optionally substituted $C_1$-$C_4$ haloalkyl, an optionally substituted $C_1$-$C_4$ heteroalkyl, $COR^A$, $CO_2R^A$, $CONR^AR^B$, $SOR^A$, $SO_2R^A$, and $SO_2NR^AR^B$, $NHCOR^A$, and $NHCONR^AR^B$, provided that at least one of $R^1$ and $R^2$ is not hydrogen;

$R^3$, $R^{3a}$, $R^4$, and $R^5$ are each independently selected from hydrogen, F, Cl, $OR^A$, an optionally substituted $C_1$-$C_4$ alkyl, and an optionally substituted $C_1$-$C_4$ haloalkyl;

wherein if $R^1$ is $NO_2$ and $R^{3a}$ is F, then at least one of $R^2$ and $R^4$ and $R^5$ is not hydrogen; and wherein if $R^1$ is $NO_2$ and $R^3$ is F, then Z is not O;

$R^6$, $R^7$, $R^{10}$, and $R^{11}$ are each independently selected from hydrogen, an optionally substituted $C_1$-$C_6$ alkyl, an optionally substituted $C_1$-$C_6$ haloalkyl, an optionally substituted $C_1$-$C_6$ heteroalkyl, an optionally substituted $C_2$-$C_6$ alkynyl, and an optionally substituted $C_2$-$C_6$ alkenyl;

$R^{6a}$ and $R^{7a}$ are each independently selected from hydrogen, an optionally substituted $C_1$-$C_6$ alkyl, an optionally substituted $C_1$-$C_6$ haloalkyl, an optionally substituted $C_1$-$C_6$ heteroalkyl, an optionally substituted $C_2$-$C_6$ alkynyl, and an optionally substituted $C_2$-$C_6$ alkenyl; or $R^{6a}$ and $R^{7a}$ together form a carbonyl;

$R^8$ and $R^9$ are each independently selected from hydrogen, an optionally substituted $C_1$-$C_8$ alkyl, an optionally substituted $C_2$-$C_8$ alkenyl, an optionally substituted $C_1$-$C_8$ haloalkyl, an optionally substituted $C_2$-$C_8$ haloalkenyl, $C_1$-$C_8$ heteroalkyl, an optionally substituted $C_2$-$C_8$ heteroalkenyl, an optionally substituted $C_2$-$C_8$ alkynyl, an optionally substituted $C_2$-$C_8$ haloalkynyl, an optionally substituted $C_2$-$C_8$ heteroalkynyl, an optionally substituted aryl, an optionally substituted heteroaryl, $CH(R^D)OR^A$, $CH(R^D)NR^AR^B$, and $(CH_2)_m R^C$;

$R^{12}$ and $R^{13}$ are each independently selected from hydrogen, F, Cl, $OR^A$, $NR^AR^B$, $SR^A$, an optionally substituted $C_1$-$C_6$ alkyl, an optionally substituted $C_1$-$C_6$ haloalkyl, an optionally substituted $C_1$-$C_6$ heteroalkyl, an optionally substituted $C_2$-$C_6$ alkynyl, an optionally substituted $C_2$-$C_6$ alkenyl, and $(CH_2)_m R^C$;

$R^{14}$ and $R^{15}$ are each independently selected from hydrogen, F, Cl, Br, I, $OR^A$, $SR^A$, $NO_2$, CN, an optionally substituted $C_1$-$C_4$ alkyl, an optionally substituted $C_1$-$C_4$ haloalkyl, an optionally substituted $C_1$-$C_4$ heteroalkyl, $NHCOR^A$, $NHCONR^A R^B$, $COR^A$, $CO_2 R^A$, $CONR^A R^B$, $SOR^A$, $SO_2 R^A$, and $SO_2 NR^A R^B$;

$R^{16}$ and $R^{17}$ are each independently selected from hydrogen, F, Cl, $OR^A$, an optionally substituted $C_1$-$C_4$ alkyl, and an optionally substituted $C_1$-$C_4$ haloalkyl;

$R^{18}$ and $R^{19}$ are each independently selected from hydrogen, F, Cl, Br, I, $OR^A$, $SR^A$, $NO_2$, CN, an optionally substituted $C_1$-$C_4$ alkyl, an optionally substituted $C_1$-$C_4$ haloalkyl, an optionally substituted $C_1$-$C_4$ heteroalkyl, $NHCOR^A$, $NHCONR^A R^B$, $COR^A$, $CO_2 R^A$, $CONR^A R^B$, $SOR^A$, $SO_2 R^A$, and $SO_2 NR^A R^B$;

$R^{20}$ and $R^{21}$ are each independently selected from hydrogen, F, Cl, $OR^A$, an optionally substituted $C_1$-$C_4$ alkyl, and an optionally substituted $C_1$-$C_4$ haloalkyl; wherein if $R^{18}$ is $NO_2$ and X is O, then at least one of $R^{19}$, $R^{20}$, and $R^{21}$ is not hydrogen, and wherein if $R^{19}$ is $NO_2$ and X is C, then at least one of $R^{18}$, $R^{20}$, and $R^{21}$ is not hydrogen;

$R^{22}$ is selected from hydrogen, an optionally substituted $C_1$-$C_4$ alkyl, an optionally substituted $C_1$-$C_4$ haloalkyl, an optionally substituted $C_1$-$C_4$ heteroalkyl, $COR^6$, $CO_2 R^A$, $CONR^A R^B$, $SO_2 R^A$, an optionally substituted aryl, an optionally substituted heteroaryl, $CH_2 CH(R^D)OR^A$, $CH_2 CH(R^D)NR^A R^B$, and $(CH_2)_m R^C$, wherein the optionally substituted aryl or optionally substituted heteroaryl is optionally substituted with a substituent selected from F, Cl, Br, I, CN, $OR^A$, $NO_2$, $NR^A R^B$, $SR^A$, $SOR^A$, $SO_2 R^A$, an optionally substituted $C_1$-$C_4$ alkyl, an optionally substituted $C_1$-$C_4$ haloalkyl, and an optionally substituted $C_1$-$C_4$ heteroalkyl;

$R^{23}$ and $R^{24}$ are each independently selected from hydrogen, an optionally substituted $C_1$-$C_8$ alkyl, an optionally substituted $C_2$-$C_8$ alkenyl, an optionally substituted $C_1$-$C_8$ haloalkyl, an optionally substituted $C_2$-$C_8$ haloalkenyl, an optionally substituted $C_1$-$C_8$ heteroalkyl, an optionally substituted $C_2$-$C_8$ heteroalkenyl, an optionally substituted $C_2$-$C_8$ alkynyl, an optionally substituted $C_2$-$C_8$ haloalkynyl, an optionally substituted $C_2$-$C_8$ heteroalkynyl, an optionally substituted aryl, an optionally substituted heteroaryl, $CH(R^D)OR^A$, $CH(R^D)NR^A R^B$, and $(CH_2)_m R^C$; or $R^{23}$ and $R^{24}$ together form a carbonyl group, provided that if $R^{18}$ is $NO_2$ and X is NH, then $R^{23}$ and $R^{24}$ do not together form a carbonyl group; or $R^{22}$ and $R^{23}$ are optionally linked to form a ring; or $R^{23}$ and $R^{25}$ are optionally linked to form a ring;

X is selected from O, S, $CR^A R^B$, $NR^D$, and a bond;

wherein if X is $CR^A R^B$ or a bond, then $R^{25}$ and $R^{26}$ are each independently selected from a halogen, $OR^A$, $NR^A R^B$, hydrogen, an optionally substituted $C_1$-$C_8$ alkyl, an optionally substituted $C_2$-$C_8$ alkenyl, an optionally substituted $C_1$-$C_8$ haloalkyl, an optionally substituted $C_2$-$C_8$ haloalkenyl, an optionally substituted $C_1$-$C_8$ heteroalkyl, an optionally substituted $C_2$-$C_8$ heteroalkenyl, an optionally substituted $C_2$-$C_8$ alkynyl, an optionally substituted $C_2$-$C_8$ haloalkynyl, an optionally substituted $C_2$-$C_8$ heteroalkynyl, an optionally substituted aryl, an optionally substituted heteroaryl, and $(CH_2)_m R^C$; or $R^{25}$ and $R^{26}$ together form a carbonyl group;

and wherein if X is O, S, or $NR^D$, then $R^{25}$ and $R^{26}$ are each independently selected from hydrogen, an optionally substituted $C_1$-$C_8$ alkyl, an optionally substituted $C_2$-$C_8$ alkenyl, an optionally substituted $C_1$-$C_8$ haloalkyl, an optionally substituted $C_2$-$C_8$ haloalkenyl, an optionally substituted $C_1$-$C_8$ heteroalkyl, an optionally substituted $C_2$-$C_8$ heteroalkenyl, an optionally substituted $C_2$-$C_8$ alkynyl, an optionally substituted $C_2$-$C_8$ haloalkynyl, an optionally substituted $C_2$-$C_8$ heteroalkynyl, an optionally substituted aryl, an optionally substituted heteroaryl, and $(CH_2)_m R^C$; or $R^{25}$ and $R^{26}$ together form a carbonyl group;

$R^A$ and $R^B$ are each independently selected from hydrogen, an optionally substituted $C_1$-$C_4$ alkyl, an optionally substituted $C_1$-$C_4$ haloalkyl, and an optionally substituted $C_1$-$C_4$ heteroalkyl;

$R^C$ is selected from an optionally substituted aryl and an optionally substituted heteroaryl that is optionally substituted with a substituent selected from F, Cl, Br, I, CN, $OR^A$, $NO_2$, $NR^A R^B$, $SR^A$, $SOR^A$, $SO_2 R^A$, an optionally substituted $C_1$-$C_4$ alkyl, an optionally substituted $C_1$-$C_4$ haloalkyl, and an optionally substituted $C_1$-$C_4$ heteroalkyl;

$R^D$ is selected from hydrogen, an optionally substituted $C_1$-$C_4$ alkyl, an optionally substituted $C_1$-$C_4$ haloalkyl, and an optionally substituted $C_1$-$C_4$ heteroalkyl;

Z is selected from O, S, $CR^A R^B$, and $NR^D$;

n is 0, 1, or 2; and m is 1 or 2.

In certain embodiments, $R^1$ and $R^2$ are each independently selected from hydrogen, F, Cl, Br, I, $OR^A$, $SR^A$, $NO_2$, CN, an optionally substituted $C_1$-$C_4$ alkyl, an optionally substituted $C_1$-$C_4$ haloalkyl, an optionally substituted $C_1$-$C_4$ heteroalkyl, $COR^A$, $CO_2 R^A$, $CONR^A R^B$, $SOR^A$, $SO_2 R^A$, and $SO_2 NR^A R^B$, $NHCOR^A$, $NHCONR^A R^B$. In certain embodiments, $R^1$ and $R^2$ are not both hydrogen.

In certain embodiments, $R^3$, $R^{3a}$, $R^4$, and $R^5$ are each independently selected from hydrogen, F, Cl, $OR^A$, an optionally substituted $C_1$-$C_4$ alkyl, and an optionally substituted $C_1$-$C_4$ haloalkyl. In certain embodiments, if $R^1$ is $NO_2$ and $R^{3a}$ is F, then at least one of $R^2$ and $R^4$ and $R^5$ is not hydrogen. In certain embodiments, if $R^1$ is $NO_2$ and $R^3$ is F, then Z is not O.

In certain embodiments, $R^6$, $R^7$, $R^{10}$, and $R^{11}$ are each independently selected from hydrogen, an optionally substituted $C_1$-$C_6$ alkyl, an optionally substituted $C_1$-$C_6$ haloalkyl, an optionally substituted $C_1$-$C_6$ heteroalkyl, an optionally substituted $C_2$-$C_6$ alkynyl, and an optionally substituted $C_2$-$C_6$ alkenyl. In certain embodiments, $R^{6a}$ and $R^{7a}$ are each independently selected from hydrogen, an optionally substituted $C_1$-$C_6$ alkyl, an optionally substituted $C_1$-$C_6$ haloalkyl, an optionally substituted $C_1$-$C_6$ heteroalkyl, an optionally substituted $C_2$-$C_6$ alkynyl, and an optionally substituted $C_2$-$C_6$ alkenyl. In certain embodiments, $R^{6a}$ and $R^{7a}$ together form a carbonyl.

In certain embodiments, $R^8$ and $R^9$ are each independently selected from hydrogen, an optionally substituted $C_1$-$C_8$ alkyl, an optionally substituted $C_2$-$C_8$ alkenyl, an optionally substituted $C_1$-$C_8$ haloalkyl, an optionally substituted $C_2$-$C_8$ haloalkenyl, $C_1$-$C_8$ heteroalkyl, an optionally substituted $C_2$-$C_8$ heteroalkenyl, an optionally substituted $C_2$-$C_8$ alkynyl, an optionally substituted $C_2$-$C_8$ haloalkynyl, an optionally substituted $C_2$-$C_8$ heteroalkynyl, aryl, an optionally substituted heteroaryl, $CH(R^D)OR^A$, $CH(R^D)NR^A R^B$, and $(CH_2)_m R^C$. In certain embodiments, $R^{12}$ and $R^{13}$ are each independently selected from hydrogen, F, Cl, $OR^A$, $NR^A R^B$, $SR^A$, an optionally substituted $C_1$-$C_6$ alkyl, an optionally substituted $C_1$-$C_6$ haloalkyl, an optionally substituted $C_1$-$C_6$ heteroalkyl, an optionally substituted $C_2$-$C_6$ alkynyl, an optionally substituted $C_2$-$C_6$ alkenyl, and $(CH_2)_m R^C$.

In certain embodiments, $R^{14}$ and $R^{15}$ are each independently selected from hydrogen, F, Cl, Br, I, $OR^A$, $SR^A$, $NO_2$, CN, an optionally substituted $C_1$-$C_4$ alkyl, an optionally substituted $C_1$-$C_4$ haloalkyl, an optionally substituted $C_1$-$C_4$ heteroalkyl, NHCOR$^A$, NHCONR$^A$R$^B$, COR$^A$, CO$_2$R$^A$, CONR$^A$R$^B$, SOR$^A$, SO$_2$R$^A$, and SO$_2$NR$^A$R$^B$.

In certain embodiments, R$^{16}$ and R$^{17}$ are each independently selected from hydrogen, F, Cl, OR$^A$, an optionally substituted C$_1$-C$_4$ alkyl, and an optionally substituted C$_1$-C$_4$ haloalkyl.

In certain embodiments, R$^{18}$ and R$^{19}$ are each independently selected from hydrogen, F, Cl, Br, I, OR$^A$, SR$^A$, NO$_2$, CN, an optionally substituted C$_1$-C$_4$ alkyl, an optionally substituted C$_1$-C$_4$ haloalkyl, an optionally substituted C$_1$-C$_4$ heteroalkyl, NHCOR$^A$, NHCONR$^A$R$^B$, COR$^A$, CO$_2$R$^A$, CONR$^A$R$^B$, SOR$^A$, SO$_2$R$^A$, and SO$_2$NR$^A$R$^B$.

In certain embodiments, R$^{20}$ and R$^{21}$ are each independently selected from hydrogen, F, Cl, OR$^A$, an optionally substituted C$_1$-C$_4$ alkyl, and an optionally substituted C$_1$-C$_4$ haloalkyl.

In certain embodiments, R$^{22}$ is selected from hydrogen, an optionally substituted C$_1$-C$_4$ alkyl, an optionally substituted C$_1$-C$_4$ haloalkyl, an optionally substituted C$_1$-C$_4$ heteroalkyl, COR$^A$, CO$_2$R$^A$, CONR$^A$R$^B$, SO$_2$R$^A$, an optionally substituted aryl, an optionally substituted heteroaryl, CH$_2$CH(R$^D$)OR$^A$, CH$_2$CH(R$^D$)NR$^A$R$^B$, and (CH$_2$)$_m$R$^C$. In certain of such embodiments, the optionally substituted aryl or optionally substituted heteroaryl is optionally substituted with a substituent selected from F, Cl, Br, I, CN, OR$^A$, NO$_2$, NR$^A$R$^B$, SR$^A$, SOR$^A$, SO$_2$R$^A$, an optionally substituted C$_1$-C$_4$ alkyl, an optionally substituted C$_1$-C$_4$ haloalkyl, and an optionally substituted C$_1$-C$_4$ heteroalkyl.

In certain embodiments, R$^{23}$ and R$^{24}$ are each independently selected from hydrogen, an optionally substituted C$_1$-C$_8$ alkyl, an optionally substituted C$_2$-C$_8$ alkenyl, an optionally substituted C$_1$-C$_8$ haloalkyl, an optionally substituted C$_2$-C$_8$ haloalkenyl, an optionally substituted C$_1$-C$_8$ heteroalkyl, an optionally substituted C$_2$-C$_8$ heteroalkenyl, an optionally substituted C$_2$-C$_8$ alkynyl, an optionally substituted C$_2$-C$_8$ haloalkynyl, an optionally substituted C$_2$-C$_8$ heteroalkynyl, an optionally substituted aryl, an optionally substituted heteroaryl, CH(R$^D$)OR$^A$, CH(R$^D$)NR$^A$R$^B$, and (CH$_2$)$_m$R$^C$. In certain embodiments, R$^{23}$ and R$^{24}$ together form a carbonyl group.

In certain embodiments, R$^{22}$ and R$^{23}$ are optionally linked to form a ring.

In certain embodiments, R$^{23}$ and R$^{25}$ are optionally linked to form a ring.

In certain embodiments, X is selected from O, S, CR$^A$R$^A$, NR$^D$, and a bond.

In certain embodiments, if X is CR$^A$R$^B$ or a bond, then R$^{25}$ and R$^{26}$ are each independently selected from a halogen, OR$^A$, NR$^A$R$^B$, hydrogen, an optionally substituted C$_1$-C$_8$ alkyl, an optionally substituted C$_2$-C$_8$ alkenyl, an optionally substituted C$_1$-C$_8$ haloalkyl, an optionally substituted C$_2$-C$_8$ haloalkenyl, an optionally substituted C$_1$-C$_8$ heteroalkyl, an optionally substituted C$_2$-C$_8$ heteroalkenyl, an optionally substituted C$_2$-C$_8$ alkynyl, an optionally substituted C$_2$-C$_8$ haloalkynyl, an optionally substituted C$_2$-C$_8$ heteroalkynyl, an optionally substituted aryl, an optionally substituted heteroaryl, and (CH$_2$)$_m$R$^C$. In certain embodiments, R$^{25}$ and R$^{26}$ together form a carbonyl group.

In certain embodiments, if X is O, S, or NR$^D$, then R$^{25}$ and R$^{26}$ are each independently selected from hydrogen, an optionally substituted C$_1$-C$_8$ alkyl, an optionally substituted C$_2$-C$_8$ alkenyl, an optionally substituted C$_1$-C$_8$ haloalkyl, an optionally substituted C$_2$-C$_8$ haloalkenyl, an optionally substituted C$_1$-C$_8$ heteroalkyl, an optionally substituted C$_2$-C$_8$ heteroalkenyl, an optionally substituted C$_2$-C$_8$ alkynyl, an optionally substituted C$_2$-C$_8$ haloalkynyl, an optionally substituted C$_2$-C$_8$ heteroalkynyl, an optionally substituted aryl, an optionally substituted heteroaryl, and (CH$_2$)$_m$R$^C$. In certain embodiments R$^{25}$ and R$^{26}$ together form a carbonyl group.

In certain embodiments, R$^A$ and R$^B$ are each independently selected from hydrogen, an optionally substituted C$_1$-C$_4$ alkyl, an optionally substituted C$_1$-C$_4$ haloalkyl, and an optionally substituted C$_1$-C$_4$ heteroalkyl.

In certain embodiments, R$^C$ is selected from an optionally substituted aryl and an optionally substituted heteroaryl that is optionally with a substituent selected from F, Cl, Br, I, CN, OR$^A$, NO$_2$, NR$^A$R$^B$, SR$^A$, SOR$^A$, SO$_2$R$^A$, an optionally substituted C$_1$-C$_4$ alkyl, an optionally substituted C$_1$-C$_4$ haloalkyl, and an optionally substituted C$_1$-C$_4$ heteroalkyl.

In certain embodiments, R$^D$ is selected from hydrogen, an optionally substituted C$_1$-C$_4$ alkyl, an optionally substituted C$_1$-C$_4$ haloalkyl, and an optionally substituted C$_1$-C$_4$ heteroalkyl.

In certain embodiments, Z is selected from O, S, CR$^A$R$^B$, and NR$^D$. In certain embodiments, n is 0, 1, or 2. In certain embodiments, m is 1 or 2. In certain embodiments, if R$^{18}$ is NO$_2$ and X is O, then R$^{19}$, R$^{20}$, and R$^{21}$ are not each hydrogen. In certain embodiments, if R$^{19}$ is NO$_2$ and X is C, then at least one of R$^{18}$, R$^{20}$, and R$^{21}$ is not hydrogen. In certain embodiments, if R$^{18}$ is NO$_2$ and X is NH, then R$^{23}$ and R$^{24}$ do not together form a carbonyl.

Compounds of Formula II and Formula IV

In certain embodiments, the compounds provided herein have Formula II or Formula IV:

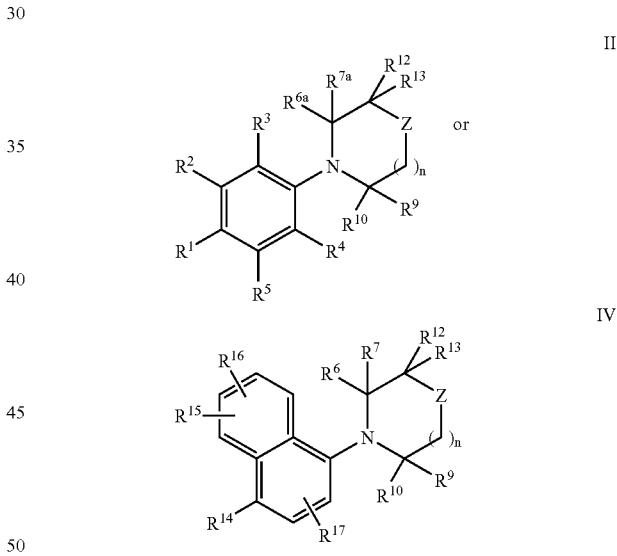

wherein the variables are as described elsewhere herein.

In another embodiment, the compounds have Formula II or Formula IV, wherein R$^1$ and R$^2$ are each independently selected from hydrogen, F, Cl, Br, I, OR$^A$, SR$^A$, NO$_2$, CN, an optionally substituted C$_1$-C$_4$ alkyl, an optionally substituted C$_1$-C$_4$ haloalkyl, an optionally substituted C$_1$-C$_4$ heteroalkyl, COR$^A$, CO$_2$R$^A$, CONR$^A$R$^B$, SOR$^A$, SO$_2$R$^A$, and SO$_2$NR$^A$R$^B$, NHCOR$^A$, and NHCONR$^A$R$^B$, provided that at least one of R$^1$ and R$^2$ is not hydrogen;

R$^3$, R$^4$, and R$^5$ are each independently selected from hydrogen, F, Cl, OR$^A$, an optionally substituted C$_1$-C$_4$ alkyl, and an optionally substituted C$_1$-C$_4$ haloalkyl;

wherein if R$^1$ is NO$_2$ and R$^3$ is F, then Z is not O;

R$^6$, R$^7$, and R$^{10}$ are each independently selected from hydrogen, an optionally substituted C$_1$-C$_6$ alkyl, an optionally substituted C$_1$-C$_6$ haloalkyl, an optionally substituted $C_1$-$C_6$ heteroalkyl, an optionally substituted $C_1$-$C_6$ heterohaloalkyl, an optionally substituted $C_1$-$C_6$ heterohaloalkenyl, an optionally substituted $C_1$-$C_6$ heterohaloalkynyl, an optionally substituted $C_2$-$C_6$ alkynyl, and an optionally substituted $C_2$-$C_6$ alkenyl;

$R^{6a}$ and $R^{7a}$ are each independently selected from hydrogen, an optionally substituted $C_1$-$C_6$ alkyl, an optionally substituted $C_1$-$C_6$ haloalkyl, an optionally substituted $C_1$-$C_6$ heteroalkyl, an optionally substituted $C_1$-$C_6$ heterohaloalkyl, an optionally substituted $C_2$-$C_6$ heterohaloalkenyl, an optionally substituted $C_2$-$C_6$ heterohaloalkynyl, an optionally substituted $C_2$-$C_6$ alkynyl, and an optionally substituted $C_2$-$C_6$ alkenyl; or $R^{6a}$ and $R^{7a}$ together form a carbonyl;

$R^9$ is selected from hydrogen, an optionally substituted $C_1$-$C_8$ alkyl, an optionally substituted $C_2$-$C_8$ alkenyl, an optionally substituted $C_1$-$C_8$ haloalkyl, an optionally substituted $C_1$-$C_6$ heterohaloalkyl, an optionally substituted $C_2$-$C_6$ heterohaloalkenyl, an optionally substituted $C_2$-$C_6$ heterohaloalkynyl, an optionally substituted $C_2$-$C_8$ haloalkenyl, $C_1$-$C_8$ heteroalkyl, an optionally substituted $C_2$-$C_8$ heteroalkenyl, an optionally substituted $C_2$-$C_8$ alkynyl, an optionally substituted $C_2$-$C_8$ haloalkynyl, an optionally substituted $C_2$-$C_8$ heteroalkynyl, an optionally substituted aryl, an optionally substituted heteroaryl, CH($R^D$)OR$^A$, CH($R^D$)NR$^A$R$^B$, COR$^A$, CO$_2$R$^A$ and (CH$_2$)$_m$R$^C$;

$R^{12}$ and $R^{13}$ are each independently selected from hydrogen, F, Cl, OR$^A$, NR$^A$R$^B$, SR$^A$, an optionally substituted $C_1$-$C_6$ alkyl, an optionally substituted $C_1$-$C_6$ haloalkyl, an optionally substituted $C_1$-$C_6$ heteroalkyl, an optionally substituted $C_1$-$C_6$ heterohaloalkyl, an optionally substituted $C_2$-$C_6$ heterohaloalkenyl, an optionally substituted $C_2$-$C_6$ heterohaloalkynyl, an optionally substituted $C_2$-$C_6$ alkynyl, an optionally substituted $C_2$-$C_6$ alkenyl, and (CH$_2$)$_m$R$^C$;

$R^{14}$ and $R^{15}$ are each independently selected from hydrogen, F, Cl, Br, I, OR$^A$, SR$^A$, NO$_2$, CN, an optionally substituted $C_1$-$C_4$ alkyl, an optionally substituted $C_1$-$C_4$ haloalkyl, an optionally substituted $C_1$-$C_4$ heteroalkyl, NHCOR$^A$, NHCONR$^A$R$^B$, COR$^A$, CO$_2$R$^A$, CONR$^A$R$^B$, SOR$^A$, SO$_2$R$^A$, and SO$_2$NR$^A$R$^B$;

$R^{16}$ and $R^{17}$ are each independently selected from hydrogen, F, Cl, OR$^A$, an optionally substituted $C_1$-$C_4$ alkyl, and an optionally substituted $C_1$-$C_4$ haloalkyl;

$R^A$ and $R^B$ are each independently selected from hydrogen, an optionally substituted $C_1$-$C_4$ alkyl, an optionally substituted $C_1$-$C_4$ haloalkyl, and an optionally substituted $C_1$-$C_4$ heteroalkyl;

$R^C$ is selected from an optionally substituted aryl and an optionally substituted heteroaryl that is optionally substituted with a substituent selected from F, Cl, Br, I, CN, OR$^A$, NO$_2$, NR$^A$R$^B$, SR$^A$, SOR$^A$, SO$_2$R$^A$, an optionally substituted $C_1$-$C_4$ alkyl, an optionally substituted $C_1$-$C_4$ haloalkyl, and an optionally substituted $C_1$-$C_4$ heteroalkyl;

$R^D$ is selected from hydrogen, an optionally substituted $C_1$-$C_4$ alkyl, an optionally substituted $C_1$-$C_4$ haloalkyl, and an optionally substituted $C_1$-$C_4$ heteroalkyl;

Z is selected from O, S, CR$^A$R$^B$, and NR$^D$;

n is 0, 1, or 2; and m is 1 or 2.

In certain embodiments, $R^1$ is selected from NO$_2$ and CN. In certain embodiments, $R^2$ is hydrogen, optionally substituted $C_1$-$C_4$ alkyl or an optionally substituted $C_1$-$C_4$ haloalkyl. In certain embodiments, $R^2$ is an optionally substituted $C_1$-$C_4$ alkyl or an optionally substituted $C_1$-$C_4$ haloalkyl. In certain embodiments, $R^2$ is hydrogen or trifluoromethyl. In certain embodiments, $R^2$ is trifluoromethyl.

In certain embodiments, $R^3$, $R^4$, and $R^5$ are each independently selected from hydrogen, F, Cl, and an optionally substituted $C_1$-$C_4$ alkyl. In certain embodiments, $R^3$, $R^4$, and $R^5$ are each independently selected from F, Cl, and an optionally substituted $C_1$-$C_4$ alkyl. In certain embodiments, $R^3$ is hydrogen. In certain embodiments, $R^4$ is hydrogen. In certain embodiments, $R^5$ is hydrogen.

In certain embodiments, $R^{6a}$ and $R^{7a}$ are each independently selected from hydrogen, an optionally substituted $C_1$-$C_6$ alkyl; an optionally substituted $C_1$-$C_6$ heterohaloalkyl; an optionally substituted $C_2$-$C_6$ heterohaloalkenyl and an optionally substituted $C_2$-$C_6$ heterohaloalkynyl, or $R^{6a}$ and $R^{7a}$ together form a carbonyl. In certain embodiments, $R^{6a}$ and $R^{7a}$ are each independently selected from an optionally substituted $C_1$-$C_6$ alkyl; an optionally substituted $C_1$-$C_6$ heterohaloalkyl; an optionally substituted $C_2$-$C_6$ heterohaloalkenyl and an optionally substituted $C_2$-$C_6$ heterohaloalkynyl, or $R^{6a}$ and $R^{7a}$ together form a carbonyl. In certain embodiments, $R^{6a}$ is hydrogen. In certain embodiments, $R^{7a}$ is hydrogen or an optionally substituted $C_1$-$C_6$ alkyl. In certain embodiments, $R^{7a}$ is an optionally substituted $C_1$-$C_6$ alkyl. In certain embodiments, $R^{7a}$ is hydrogen or methyl. In certain embodiments, $R^{7a}$ is hydrogen. In certain embodiments, $R^{7a}$ is methyl. In certain embodiments, $R^{6a}$ and $R^{7a}$ together form a carbonyl.

In certain embodiments, $R^{10}$ is selected from hydrogen, an optionally substituted $C_1$-$C_6$ alkyl, an optionally substituted $C_1$-$C_6$ haloalkyl, an optionally substituted $C_1$-$C_6$ heteroalkyl, an optionally substituted $C_2$-$C_6$ heterohaloalkenyl, an optionally substituted $C_2$-$C_6$ heterohaloalkynyl, an optionally substituted $C_1$-$C_6$ heterohaloalkyl, an optionally substituted $C_2$-$C_6$ alkynyl, and an optionally substituted $C_2$-$C_6$ alkenyl. In certain embodiments, $R^{10}$ is selected from an optionally substituted $C_1$-$C_6$ alkyl, an optionally substituted $C_1$-$C_6$ haloalkyl, an optionally substituted $C_1$-$C_6$ heteroalkyl, an optionally substituted $C_2$-$C_6$ heterohaloalkenyl, an optionally substituted $C_2$-$C_6$ heterohaloalkynyl, an optionally substituted $C_1$-$C_6$ heterohaloalkyl, an optionally substituted $C_2$-$C_6$ alkynyl, and an optionally substituted $C_2$-$C_6$ alkenyl. In certain embodiments, $R^{10}$ is hydrogen.

In certain embodiments, $R^9$ is selected from hydrogen, F, Cl, Br, I, an optionally substituted $C_1$-$C_4$ alkyl, an optionally substituted $C_1$-$C_6$ heterohaloalkyl, an optionally substituted $C_2$-$C_6$ heterohaloalkenyl, an optionally substituted $C_2$-$C_6$ heterohaloalkynyl, COR$^A$, CO$_2$R$^A$, CH($R^D$)OR$^A$ and CH($R^D$)NR$^A$R$^B$. In certain embodiments, $R^9$ is selected from F, Cl, Br, I, an optionally substituted $C_1$-$C_4$ alkyl, an optionally substituted $C_1$-$C_6$ heterohaloalkyl, an optionally substituted $C_2$-$C_6$ heterohaloalkenyl, an optionally substituted $C_2$-$C_6$ heterohaloalkynyl, COR$^A$, CO$_2$R$^A$, CH($R^D$)OR$^A$ and CH($R^D$)NR$^A$R$^B$.

In certain embodiments, $R^9$ is hydrogen, formyl, hydroxy $C_1$-$C_6$alkyl, hydroxyhalo$C_1$-$C_6$alkyl, $C_1$-$C_6$alkylsilyloxy $C_1$-$C_6$alkyl, $C_1$-$C_6$alkoxycarbonyl, amino$C_1$-$C_6$alkyl, carboxy, or $C_1$-$C_6$alkylcarbonyloxy$C_1$-$C_6$alkyl. In certain embodiments, $R^9$ is formyl, hydroxy $C_1$-$C_6$alkyl, hydroxyhalo$C_1$-$C_6$alkyl, $C_1$-$C_6$alkylsilyloxy $C_1$-$C_6$alkyl, $C_1$-$C_6$alkoxycarbonyl, amino$C_1$-$C_6$alkyl, carboxy, or $C_1$-$C_6$alkylcarbonyloxy$C_1$-$C_6$alkyl.

In other embodiments, $R^9$ is hydrogen, formyl, hydroxymethyl, 1-hydroxy-2,2,2-trifluoroethyl, tributylsilyloxymethyl, ethoxycarbonyl, aminomethyl, carboxy, or acetoxymethyl. In other embodiments, $R^9$ is formyl, hydroxymethyl, 1-hydroxy-2,2,2-trifluoroethyl, tributylsilyloxymethyl, ethoxycarbonyl, aminomethyl, carboxy, or acetoxymethyl.

In certain embodiments, $R^{12}$ and $R^{13}$ are each independently selected from hydrogen, F, Cl, OR$^A$, an optionally substituted $C_1$-$C_6$ alkyl, an optionally substituted $C_1$-$C_6$ heterohaloalkyl, an optionally substituted $C_2$-$C_6$ heterohaloalkenyl, an optionally substituted $C_2$-$C_6$ heterohaloalkynyl, and $(CH_2)_m R^C$. In certain embodiments, $R^{12}$ and $R^{13}$ are each independently selected from F, Cl, $OR^A$, an optionally substituted $C_1$-$C_6$ alkyl, an optionally substituted $C_1$-$C_6$ heterohaloalkyl, an optionally substituted $C_2$-$C_6$ heterohaloalkenyl, an optionally substituted $C_2$-$C_6$ heterohaloalkynyl, and $(CH_2)_m R^C$. In certain embodiments, $R^{12}$ is hydrogen. In certain embodiments, $R^{13}$ is hydrogen, F, OH or benzyl. In certain embodiments, $R^{13}$ is F, OH or benzyl.

In another embodiment, the compounds provided herein have Formula II or Formula IV, wherein at least one of $R^{6a}$, $R^{7a}$, $R^6$, $R^7$, $R^9$, $R^{10}$, $R^{12}$ and $R^{13}$ is an optionally substituted $C_1$-$C_6$ heterohaloalkyl; and the other variables are as described elsewhere herein. In another embodiment, the compounds provided herein have Formula II, wherein at least one of $R^{6a}$, $R^{7a}$, $R^9$, $R^{10}$, $R^{12}$ and $R^{13}$ is an optionally substituted $C_1$-$C_6$ heterohaloalkyl; and the other variables are as described elsewhere herein. In another embodiment, the compounds provided herein have Formula IV, wherein at least one of $R^6$, $R^7$, $R^9$, $R^{10}$, $R^{12}$ and $R^{13}$ is an optionally substituted $C_1$-$C_6$ heterohaloalkyl; and the other variables are as described elsewhere herein.

In certain embodiments, the compounds are of Formula II, wherein $R^1$ is selected from $NO_2$ and CN;

$R^2$ is hydrogen, optionally substituted $C_1$-$C_4$ alkyl or an optionally substituted $C_1$-$C_4$ haloalkyl;

$R^3$, $R^4$, and $R^5$ are each independently selected from hydrogen, F, Cl, and an optionally substituted $C_1$-$C_4$ alkyl;

$R^{6a}$ and $R^{7a}$ are each independently selected from hydrogen and an optionally substituted $C_1$-$C_6$ alkyl; an optionally substituted $C_1$-$C_6$ heterohaloalkyl or $R^{6a}$ and $R^{7a}$ together form a carbonyl;

$R^9$ is selected from hydrogen, F, Cl, Br, I, an optionally substituted $C_1$-$C_4$ alkyl, an optionally substituted $C_1$-$C_6$ heterohaloalkyl, $COR^A$, $CO_2R^A$, $CH(R^D)OR^A$, and $CH(R^D)NR^AR^B$;

$R^{10}$ is hydrogen;

$R^{12}$ and $R^{13}$ are each independently selected from hydrogen, F, Cl, $OR^A$, an optionally substituted $C_1$-$C_6$ alkyl, an optionally substituted $C_1$-$C_6$ heterohaloalkyl and $(CH_2)_m R^C$; and other variables are as described elsewhere herein.

In certain embodiments, the compounds are of Formula II, wherein $R^1$ is selected from $NO_2$ and CN;

$R^2$ is an optionally substituted $C_1$-$C_4$ alkyl or an optionally substituted $C_1$-$C_4$ haloalkyl;

$R^3$, $R^4$, and $R^5$ are each independently selected from F, Cl, and an optionally substituted $C_1$-$C_4$ alkyl;

$R^{6a}$ and $R^{7a}$ are each independently selected from an optionally substituted $C_1$-$C_6$ alkyl; an optionally substituted $C_1$-$C_6$ heterohaloalkyl or $R^{6a}$ and $R^{7a}$ together form a carbonyl;

$R^9$ is selected from F, Cl, Br, I, an optionally substituted $C_1$-$C_4$ alkyl, an optionally substituted $C_1$-$C_6$ heterohaloalkyl, $COR^A$, $CO_2R^A$, $CH(R^D)OR^A$, and $CH(R^D)NR^AR^B$;

$R^{10}$ is hydrogen;

$R^{12}$ and $R^{13}$ are each independently selected from F, Cl, $OR^A$, an optionally substituted $C_1$-$C_6$ alkyl, an optionally substituted $C_1$-$C_6$ heterohaloalkyl and $(CH_2)_m R^C$; and other variables are as described elsewhere herein.

In certain embodiments, the compounds have formula IIA,

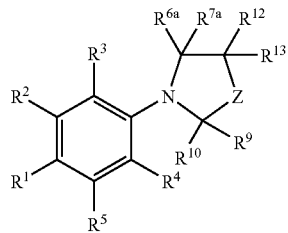

wherein the variables are as described elsewhere herein.
In certain embodiments, the compounds have formula IIB,

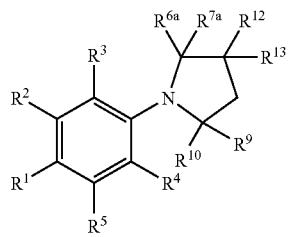

wherein the variables are as described elsewhere herein. In certain embodiments, the compounds have formula IIB, wherein $R^1$ is selected from $NO_2$ and CN;

$R^2$ is hydrogen, optionally substituted $C_1$-$C_4$ alkyl or an optionally substituted $C_1$-$C_4$ haloalkyl;

$R^3$, $R^4$, and $R^5$ are each independently selected from hydrogen, F, Cl, and an optionally substituted $C_1$-$C_4$ alkyl;

$R^{6a}$ and $R^{7a}$ are each independently selected from hydrogen and an optionally substituted $C_1$-$C_6$ alkyl; an optionally substituted $C_1$-$C_6$ heterohaloalkyl, or $R^{6a}$ and $R^{7a}$ together form a carbonyl;

$R^9$ is selected from hydrogen, F, Cl, Br, I, an optionally substituted $C_1$-$C_4$ alkyl, an optionally substituted $C_1$-$C_6$ heterohaloalkyl, $COR^A$, $CO_2R^A$, $CH(R^D)OR^A$, and $CH(R^D)NR^AR^B$;

$R^{10}$ is hydrogen; and $R^{12}$ and $R^{13}$ are each independently selected from hydrogen, F, Cl, $OR^A$, an optionally substituted $C_1$-$C_6$ alkyl, an optionally substituted $C_1$-$C_6$ heterohaloalkyl and $(CH_2)_m R^C$.

In certain embodiments, the compounds of formula IIB, wherein $R^1$ is selected from $NO_2$ and CN;

$R^2$ is hydrogen or an optionally substituted $C_1$-$C_4$ haloalkyl;

$R^3$, $R^4$, and $R^5$ are each independently selected from hydrogen and an optionally substituted $C_1$-$C_4$ alkyl;

$R^{6a}$ and $R^{7a}$ are each independently selected from hydrogen and an optionally substituted $C_1$-$C_6$ alkyl, an optionally substituted $C_1$-$C_6$ heterohaloalkyl; or $R^{6a}$ and $R^{7a}$ together form a carbonyl;

$R^9$ is selected from hydrogen, an optionally substituted $C_1$-$C_6$ heterohaloalkyl, F, Cl, $COR^A$, $CO_2R^A$, $CH(R^D)OR^A$, and $CH(R^D)NR^AR^B$;

$R^{10}$ is hydrogen; and $R^{12}$ and $R^{13}$ are each independently selected from hydrogen, optionally substituted $C_1$-$C_4$ alkyl, an optionally substituted $C_1$-$C_6$ heterohaloalkyl, $OR^A$, and $(CH_2)_m R^C$.

In certain embodiments, in the compounds of formula IIB, $R^1$ is selected from $NO_2$ and CN;

$R^2$ is hydrogen or trifluoromethyl;

$R^3$, $R^4$, are $R^5$ each hydrogen;

$R^{7a}$ is hydrogen or methyl and $R^{6a}$ is hydrogen; or $R^{6a}$ and $R^{7a}$ together form a carbonyl;

$R^9$ is selected from hydrogen, formyl, hydroxymethyl, 1-hydroxy-2,2,2-trifluoroethyl, tributylsilyloxymethyl, ethoxycarbonyl, aminomethyl, carboxy, and acetyoxymethyl $R^{10}$ is hydrogen;

$R^{12}$ is hydrogen; and $R^{13}$ is selected from hydrogen, F, OH and benzyl.

In certain embodiments, the compounds have formula:

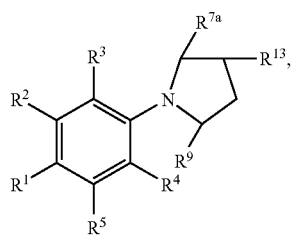

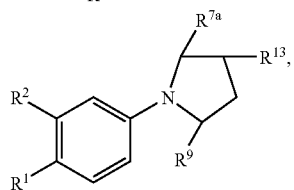

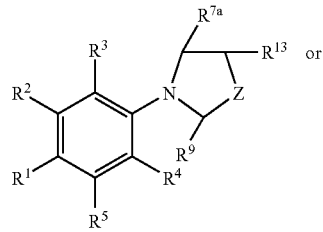

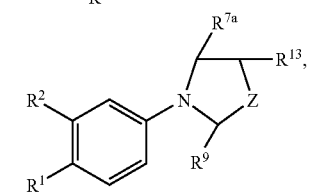

wherein the variables are as described elsewhere herein. In certain embodiments, at least one of $R^{7a}$, $R^9$ and $R^{13}$ is an optionally substituted $C_1$-$C_6$ heterohaloalkyl. In certain embodiments, $R^{7a}$ is an optionally substituted $C_1$-$C_6$ heterohaloalkyl. In certain embodiments, $R^9$ is an optionally substituted $C_1$-$C_6$ heterohaloalkyl. In certain embodiments, $R^{13}$ is an optionally substituted $C_1$-$C_6$ heterohaloalkyl.

In another embodiment, the compounds have formula:

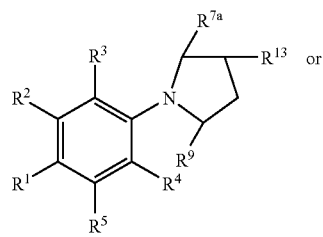

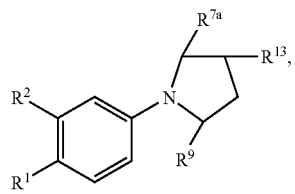

wherein the variables are as described elsewhere herein.

In certain embodiments, the compounds have formula:

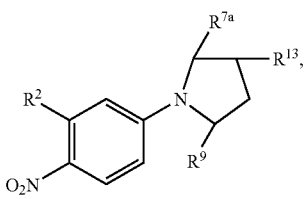

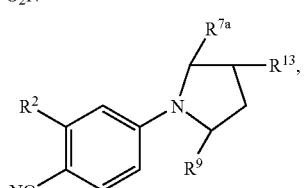

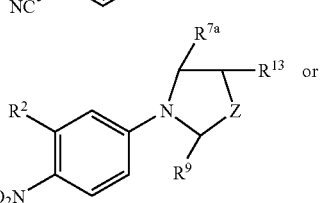

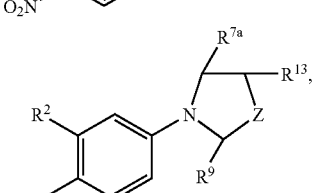

wherein the variables are as described elsewhere herein.

In certain embodiments, the compounds have formula:

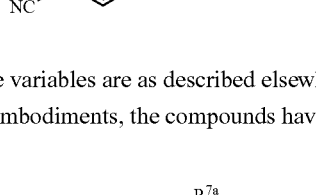

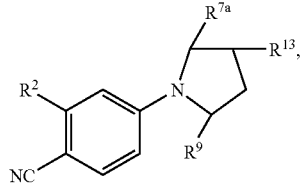

wherein the variables are as described elsewhere herein.

In certain embodiments, the compounds have Formula IIC or IID:

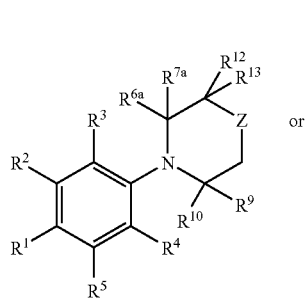

(IIC)

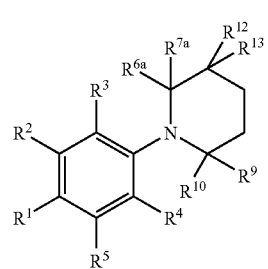

(IID)

wherein the variables are as described elsewhere herein.
In certain embodiments, the compounds have formula IID:

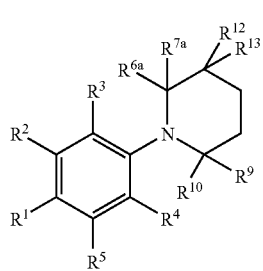

wherein the variables are as described elsewhere herein. In certain embodiments the compounds have formula IID, wherein $R^1$ is $NO_2$; $R_2$ is hydrogen or haloalkyl; $R^3$, $R^4$, $R^5$, $R^{6a}$, $R^{7a}$, $R^9$, $R^{12}$, and $R^{13}$ are each hydrogen; and $R^9$ is selected from $CO_2R^A$ $CH(R^D)OR^A$, and $CH(R^D)NR^AR^B$. In certain embodiments the compounds have formula IID, wherein $R^1$ is $NO_2$; $R_2$ is hydrogen or trifluoromethyl; $R^3$, $R^4$, $R^5$, $R^{6a}$, $R^{7a}$, $R^9$, $R^{12}$, and $R^{13}$ are each hydrogen; and $R^9$ is selected from hydroxymethyl, ethoxycarbonyl and acetyoxymethyl.

In certain embodiments, the compounds have formula:

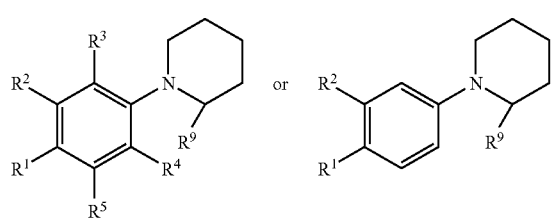

wherein the variables are as described elsewhere herein.

In certain embodiments, the compounds have formula:

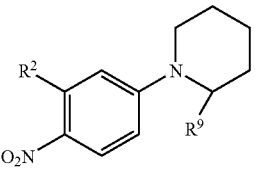

wherein the variables are as described elsewhere herein.
In certain embodiments, the compounds have Formula:

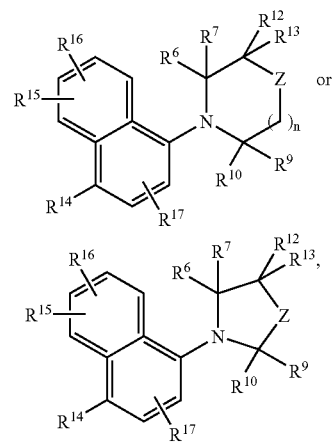

wherein the variables are as described elsewhere herein.
In other embodiments, the compounds have formula:

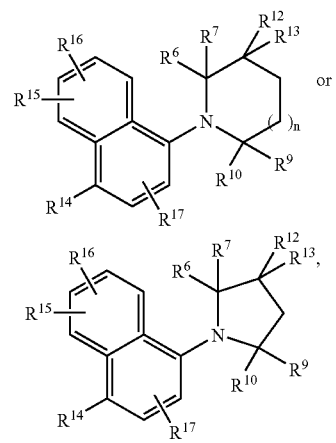

wherein the variables are as described elsewhere herein.
Compounds of Formula V or VI
In other embodiments, the compounds have formula:

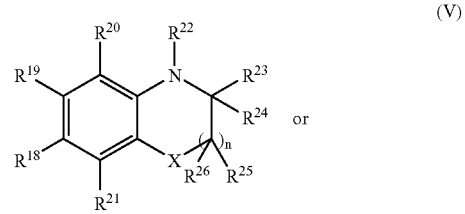

(V)

-continued

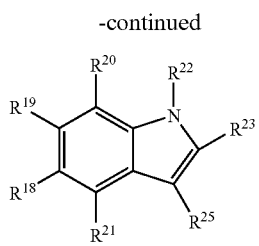
(VI)

wherein the variables are as described elsewhere herein.

In certain embodiments, the compounds have Formula (V) or VI, wherein $R^{18}$ and $R^{19}$ are each independently selected from hydrogen, F, Cl, Br, I, $OR^A$, $SR^A$, $NO_2$, CN, an optionally substituted $C_1$-$C_4$ alkyl, an optionally substituted $C_1$-$C_4$ haloalkyl, an optionally substituted $C_1$-$C_4$ heteroalkyl, $NHCOR^A$, $NHCONR^AR^B$, $COR^A$, $CO_2R^A$, $CONR^AR^B$, $SOR^A$, $SO_2R^A$, and $SO_2NR^AR^B$;

$R^{20}$ and $R^{21}$ are each independently selected from hydrogen, F, Cl, $OR^A$, an optionally substituted $C_1$-$C_4$ alkyl, and an optionally substituted $C_1$-$C_4$ haloalkyl; wherein if $R^{18}$ is $NO_2$ and X is O, then at least one of $R^{19}$, $R^{20}$, and $R^{21}$ is not hydrogen, and wherein if $R^{19}$ is $NO_2$ and X is C, then at least one of $R^{18}$, $R^{20}$, and $R^{21}$ is not hydrogen;

$R^{22}$ is selected from hydrogen, an optionally substituted $C_1$-$C_4$ alkyl, an optionally substituted $C_1$-$C_4$ haloalkyl, an optionally substituted $C_1$-$C_4$ heteroalkyl, an optionally substituted $C_1$-$C_6$ heterohaloalkyl, an optionally substituted $C_2$-$C_6$ heterohaloalkenyl, an optionally substituted $C_2$-$C_6$ heterohaloalkynyl, $COR^6$, $CO_2R^A$, $CONR^AR^B$, $SO_2R^A$, an optionally substituted aryl, an optionally substituted heteroaryl, $CH_2CH(R^D)OR^A$, $CH_2CH(R^D)NR^AR^B$, and $(CH_2)_m R^C$, wherein the optionally substituted aryl or optionally substituted heteroaryl is optionally substituted with a substituent selected from F, Cl, Br, I, CN, $OR^A$, $NO_2$, $NR^AR^B$, $SR^A$, $SOR^A$, $SO_2R^A$, an optionally substituted $C_1$-$C_4$ alkyl, an optionally substituted $C_1$-$C_4$ haloalkyl, and an optionally substituted $C_1$-$C_4$ heteroalkyl;

$R^{23}$ and $R^{24}$ are each independently selected from hydrogen, an optionally substituted $C_1$-$C_8$ alkyl, an optionally substituted $C_2$-$C_8$ alkenyl, an optionally substituted $C_1$-$C_8$ haloalkyl, an optionally substituted $C_2$-$C_8$ haloalkenyl, an optionally substituted $C_1$-$C_8$ heteroalkyl, an optionally substituted $C_1$-$C_6$ heterohaloalkyl, an optionally substituted $C_2$-$C_8$ heteroalkenyl, an optionally substituted $C_2$-$C_8$ alkynyl, an optionally substituted $C_2$-$C_8$ haloalkynyl, an optionally substituted $C_2$-$C_8$ heteroalkynyl, an optionally substituted $C_2$-$C_8$ heterohaloalkenyl, an optionally substituted $C_2$-$C_8$ heterohaloalkynyl, an optionally substituted aryl, an optionally substituted heteroaryl, $CH(R^D)OR^A$, $CH(R^D)NR^AR^B$, and $(CH_2)_m R^C$; or $R^{23}$ and $R^{24}$ together form a carbonyl group, provided that if $R^{18}$ is $NO_2$ and X is NH, then $R^{23}$ and $R^{24}$ do not together form a carbonyl group; or $R^{22}$ and $R^{23}$ are optionally linked to form a ring; or $R^{23}$ and $R^{25}$ are optionally linked to form a ring;

$R^{25}$ is selected from a halogen, $OR^A$, $NR^AR^B$, hydrogen, an optionally substituted $C_1$-$C_8$ alkyl, an optionally substituted $C_2$-$C_8$ alkenyl, an optionally substituted $C_1$-$C_8$ haloalkyl, an optionally substituted $C_2$-$C_8$ haloalkenyl, an optionally substituted $C_1$-$C_8$ heteroalkyl, an optionally substituted $C_2$-$C_6$ heterohaloalkynyl, an optionally substituted $C_2$-$C_8$ heteroalkenyl, an optionally substituted $C_2$-$C_8$ alkynyl, an optionally substituted $C_2$-$C_8$ haloalkynyl, an optionally substituted $C_2$-$C_8$ heterohaloalkenyl, an optionally substituted $C_2$-$C_8$ heterohaloalkynyl, an optionally substituted $C_2$-$C_8$ heteroalkynyl, an optionally substituted aryl, an optionally substituted heteroaryl, and $(CH_2)_m R^C$;

X is selected from O, S, $CR^AR^B$, $NR^D$, and a bond;

wherein if X is $CR^AR^B$ or a bond, then $R^{25}$ and $R^{26}$ are each independently selected from a halogen, $OR^A$, $NR^AR^B$, hydrogen, an optionally substituted $C_1$-$C_8$ alkyl, an optionally substituted $C_2$-$C_8$ alkenyl, an optionally substituted $C_1$-$C_8$ haloalkyl, an optionally substituted $C_2$-$C_8$ haloalkenyl, an optionally substituted $C_1$-$C_8$ heteroalkyl, an optionally substituted $C_1$-$C_6$ heterohaloalkyl, an optionally substituted $C_2$-$C_6$ heterohaloalkenyl, an optionally substituted $C_2$-$C_6$ heterohaloalkynyl, an optionally substituted $C_2$-$C_8$ heteroalkenyl, an optionally substituted $C_2$-$C_8$ alkynyl, an optionally substituted $C_2$-$C_8$ haloalkynyl, an optionally substituted $C_2$-$C_8$ heteroalkynyl, an optionally substituted aryl, an optionally substituted heteroaryl, and $(CH_2)_m R^C$; or $R^{25}$ and $R^{26}$ together form a carbonyl group;

and wherein if X is O, S, or $NR^D$, then $R^{25}$ and $R^{16}$ are each independently selected from hydrogen, an optionally substituted $C_1$-$C_8$ alkyl, an optionally substituted $C_2$-$C_8$ alkenyl, an optionally substituted $C_1$-$C_8$ haloalkyl, an optionally substituted $C_2$-$C_8$ haloalkenyl, an optionally substituted $C_1$-$C_8$ heteroalkyl, an optionally substituted $C_1$-$C_6$ heterohaloalkyl, an optionally substituted $C_2$-$C_6$ heterohaloalkenyl, an optionally substituted $C_2$-$C_6$ heterohaloalkynyl, an optionally substituted $C_2$-$C_8$ heteroalkenyl, an optionally substituted $C_2$-$C_8$ alkynyl, an optionally substituted $C_2$-$C_8$ haloalkynyl, an optionally substituted $C_2$-$C_8$ heteroalkynyl, an optionally substituted aryl, an optionally substituted heteroaryl, and $(CH_2)_m R^C$; or $R^{25}$ and $R^{26}$ together form a carbonyl group;

$R^A$ and $R^B$ are each independently selected from hydrogen, an optionally substituted $C_1$-$C_4$ alkyl, an optionally substituted $C_1$-$C_4$ haloalkyl, and an optionally substituted $C_1$-$C_4$ heteroalkyl;

$R^C$ is selected from an optionally substituted aryl and an optionally substituted heteroaryl that is optionally substituted with a substituent selected from F, Cl, Br, I, CN, $OR^A$, $NO_2$, $NR^AR^B$, $SR^A$, $SOR^A$, $SO_2R^A$, an optionally substituted $C_1$-$C_4$ alkyl, an optionally substituted $C_1$-$C_4$ haloalkyl, and an optionally substituted $C_1$-$C_4$ heteroalkyl;

$R^D$ is selected from hydrogen, an optionally substituted $C_1$-$C_4$ alkyl, an optionally substituted $C_1$-$C_4$ haloalkyl, and an optionally substituted $C_1$-$C_4$ heteroalkyl;

Z is selected from O, S, $CR^AR^B$, and $NR^D$;

n is 0, 1, or 2; and m is 1 or 2.

In other embodiments, the compounds have formula:

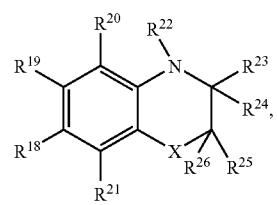

wherein the variables are as described elsewhere herein.

In other embodiments, the compounds have formula:

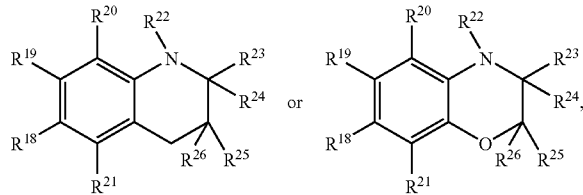

wherein the variables are as described elsewhere herein.

In other embodiments, $R^{18}$ and $R^{19}$ are each independently selected from hydrogen, F, Cl, Br, I, $OR^A$, $SR^A$, $NO_2$, CN, an optionally substituted $C_1$-$C_4$ alkyl, an optionally substituted $C_1$-$C_4$ haloalkyl, an optionally substituted $C_1$-$C_4$ heteroalkyl, $NHCOR^A$, $NHCONR^AR^B$, $COR^A$, $CO_2R^A$, $CONR^AR^B$, $SOR^A$, $SO_2R^A$, and $SO_2NR^AR^B$;

$R^{23}$ and $R^{24}$ are each independently selected from hydrogen, an optionally substituted $C_1$-$C_8$ alkyl, an optionally substituted $C_2$-$C_8$ alkenyl, an optionally substituted $C_1$-$C_8$ haloalkyl, an optionally substituted $C_2$-$C_8$ haloalkenyl, an optionally substituted $C_1$-$C_8$ heteroalkyl, an optionally substituted $C_2$-$C_8$ heteroalkenyl, an optionally substituted $C_2$-$C_8$ alkynyl, an optionally substituted $C_2$-$C_8$ haloalkynyl, an optionally substituted $C_2$-$C_8$ heteroalkynyl, an optionally substituted aryl, an optionally substituted heteroaryl, $CH(R^D)OR^A$, $CH(R^D)NR^AR^B$, and $(CH_2)_mR^C$; or $R^{23}$ and $R^{24}$ together form a carbonyl group, provided that if $R^{18}$ is $NO_2$ and X is NH, then $R^{23}$ and $R^{24}$ do not together form a carbonyl group; or $R^{22}$ and $R^{23}$ are optionally linked to form a ring; or $R^{23}$ and $R^{25}$ are optionally linked to form a ring;

$R^{25}$ is selected from a halogen, $OR^A$, $NR^AR^B$, hydrogen, an optionally substituted $C_1$-$C_8$ alkyl, an optionally substituted $C_2$-$C_8$ alkenyl, an optionally substituted $C_1$-$C_8$ haloalkyl, an optionally substituted $C_2$-$C_8$ haloalkenyl, an optionally substituted $C_1$-$C_8$ heteroalkyl, an optionally substituted $C_2$-$C_8$ heteroalkenyl, an optionally substituted-$C_2$-$C_8$ alkynyl, an optionally substituted $C_2$-$C_8$ haloalkynyl, an optionally substituted $C_2$-$C_8$ heteroalkynyl, an optionally substituted aryl, an optionally substituted heteroaryl, and $(CH_2)_mR^C$;

X is selected from O, S, $CR^AR^B$, $NR^D$, and a bond;

wherein if X is $CR^AR^B$ or a bond, then $R^{25}$ and $R^{26}$ are each independently selected from a halogen, $OR^A$, $NR^AR^B$, hydrogen, an optionally substituted $C_1$-$C_8$ alkyl, an optionally substituted $C_2$-$C_8$ alkenyl, an optionally substituted $C_1$-$C_8$ haloalkyl, an optionally substituted $C_2$-$C_8$ haloalkenyl, an optionally substituted $C_1$-$C_8$ heteroalkyl, an optionally substituted $C_2$-$C_8$ heteroalkenyl, an optionally substituted $C_2$-$C_8$ alkynyl, an optionally substituted $C_2$-$C_8$ haloalkynyl, an optionally substituted $C_2$-$C_8$ heteroalkynyl, an optionally substituted aryl, an optionally substituted heteroaryl, and $(CH_2)_mR^C$; or $R^{25}$ and $R^{26}$ together form a carbonyl group;

and wherein if X is O, S, or $NR^D$, then $R^{25}$ and $R^{26}$ are each independently selected from hydrogen, an optionally substituted $C_1$-$C_8$ alkyl, an optionally substituted $C_2$-$C_8$ alkenyl, an optionally substituted $C_1$-$C_8$ haloalkyl, an optionally substituted $C_2$-$C_8$ haloalkenyl, an optionally substituted $C_1$-$C_8$ heteroalkyl, an optionally substituted $C_2$-$C_8$ heteroalkenyl, an optionally substituted $C_2$-$C_8$ alkynyl, an optionally substituted $C_2$-$C_8$ haloalkynyl, an optionally substituted $C_2$-$C_8$ heteroalkynyl, an optionally substituted aryl, an optionally substituted heteroaryl, and $(CH_2)_mR^C$; or $R^{25}$ and $R^{26}$ together form a carbonyl group;

$R^A$ and $R^B$ are each independently selected from hydrogen, an optionally substituted $C_1$-$C_4$ alkyl, an optionally substituted $C_1$-$C_4$ haloalkyl, and an optionally substituted $C_1$-$C_4$ heteroalkyl;

$R^C$ is selected from an optionally substituted aryl and an optionally substituted heteroaryl that is optionally substituted with a substituent selected from F, Cl, Br, I, CN, $OR^A$, $NO_2$, $NR^AR^B$, $SR^A$, $SOR^A$, $SO_2R^A$, an optionally substituted $C_1$-$C_4$ alkyl, an optionally substituted $C_1$-$C_4$ haloalkyl, and an optionally substituted $C_1$-$C_4$ heteroalkyl;

$R^D$ is selected from hydrogen, an optionally substituted $C_1$-$C_4$ alkyl, an optionally substituted $C_1$-$C_4$ haloalkyl, and an optionally substituted $C_1$-$C_4$ heteroalkyl;

Z is selected from O, S, $CR^AR^B$, and $NR^D$;

n is 0, 1, or 2; and m is 1 or 2.

In other embodiments, $R^{18}$ and $R^{19}$ are each independently selected from hydrogen, $NO_2$, and an optionally substituted $C_1$-$C_4$ alkyl; $R^{22}$ is hydrogen, an optionally substituted $C_1$-$C_4$ alkyl and an optionally substituted $C_1$-$C_4$ haloalkyl; $R^{23}$ and $R^{24}$ are each independently hydrogen or an optionally substituted $C_1$-$C_4$ alkyl; and $R^{25}$ and $R^{26}$ are each hydrogen.

In other embodiments, $R^{18}$ is $NO_2$. In other embodiments, $R^{19}$ is $NO_2$. In other embodiments, $R^{22}$ is hydrogen or haloalkyl. In other embodiments, $R^{22}$ is haloalkyl. In other embodiments, $R^{22}$ is hydrogen or 2,2,2-trifluoroethyl. In other embodiments, $R^{23}$ and $R^{24}$ are each independently hydrogen or methyl.

In other embodiments, the compounds have formula:

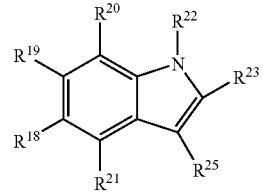

wherein the variables are as described elsewhere herein. In other embodiments, $R^{18}$ and $R^{19}$ are each independently selected from hydrogen, $NO_2$, and an optionally substituted $C_1$-$C_4$ alkyl; $R^{22}$ is hydrogen, an optionally substituted $C_1$-$C_4$ alkyl and an optionally substituted $C_1$-$C_4$ haloalkyl; $R^{23}$ and $R^{24}$ are each independently hydrogen or an optionally substituted $C_1$-$C_4$ alkyl; and $R^{25}$ is hydrogen, an optionally substituted $C_1$-$C_4$ alkyl or alkoxyaryl.

In other embodiments, $R^{18}$ is $NO_2$. In other embodiments, $R^{19}$ is $NO_2$. In other embodiments, $R^{22}$ is hydrogen or haloalkyl. In other embodiments, $R^{22}$ is hydrogen or 2,2,2-trifluoroethyl. In other embodiments, $R^{23}$ is hydrogen or methyl. In other embodiments, $R^{25}$ is hydrogen, methyl or methoxyphenyl.

Compounds of Formula I

In other embodiments, the compounds have Formula I:

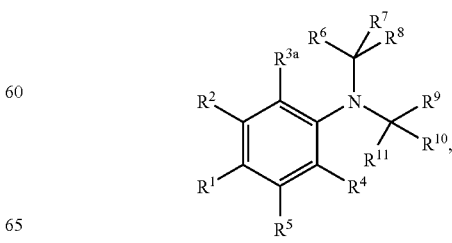

wherein the variables are as described elsewhere herein.

In certain embodiments, $R^1$ and $R^2$ are each independently selected from hydrogen, F, Cl, Br, I, $OR^A$, $SR^A$, $NO_2$, CN, an optionally substituted $C_1$-$C_4$ alkyl, an optionally substituted $C_1$-$C_4$ haloalkyl, an optionally substituted $C_1$-$C_4$ heteroalkyl, $COR^A$, $CO_2R^A$, $CONR^AR^B$, $SOR^A$, $SO_2R^A$, and $SO_2NR^AR^B$, $NHCOR^A$, and $NHCONR^AR^B$, provided that at least one of $R^1$ and $R^2$ is not hydrogen;

$R^{3a}$, $R^4$, and $R^5$ are each independently selected from hydrogen, F, Cl, $OR^A$, an optionally substituted $C_1$-$C_4$ alkyl, and an optionally substituted $C_1$-$C_4$ haloalkyl;

wherein if $R^1$ is $NO_2$ and $R^{3a}$ is F, then at least one of $R^2$ and $R^4$ and $R^5$ is not hydrogen;

$R^6$, $R^7$, $R^{10}$, and $R^{11}$ are each independently selected from hydrogen, an optionally substituted $C_1$-$C_6$ alkyl, an optionally substituted $C_1$-$C_6$ haloalkyl, an optionally substituted $C_1$-$C_6$ heteroalkyl, an optionally substituted $C_1$-$C_6$ heterohaloalkyl, an optionally substituted $C_2$-$C_6$ heterohaloalkenyl, an optionally substituted $C_2$-$C_6$ heterohaloalkynyl, an optionally substituted $C_2$-$C_6$ alkynyl, and an optionally substituted $C_2$-$C_6$ alkenyl;

$R^8$ and $R^9$ are each independently selected from hydrogen, an optionally substituted $C_1$-$C_8$ alkyl, an optionally substituted $C_2$-$C_8$ alkenyl, an optionally substituted $C_1$-$C_8$ haloalkyl, an optionally substituted $C_2$-$C_8$ haloalkenyl, $C_1$-$C_8$ heteroalkyl, an optionally substituted $C_2$-$C_8$ heteroalkenyl, an optionally substituted $C_2$-$C_8$ alkynyl, an optionally substituted $C_2$-$C_8$ haloalkynyl, an optionally substituted $C_2$-$C_8$ heteroalkynyl, an optionally substituted $C_1$-$C_6$ heterohaloalkyl, an optionally substituted $C_2$-$C_6$ heterohaloalkenyl, an optionally substituted $C_2$-$C_6$ heterohaloalkynyl, an optionally substituted aryl, an optionally substituted heteroaryl, $CH(R^D)OR^A$, $CH(R^D)NR^AR^B$, and $(CH_2)_mR^C$;

$R^{14}$ and $R^{15}$ are each independently selected from hydrogen, F, Cl, Br, I, $OR^A$, $SR^A$, $NO_2$, CN, an optionally substituted $C_1$-$C_4$ alkyl, an optionally substituted $C_1$-$C_4$ haloalkyl, an optionally substituted $C_1$-$C_4$ heteroalkyl, $NHCOR^A$, $NHCONR^AR^B$, $COR^A$, $CO_2R^A$, $CONR^AR^B$, $SOR^A$, $SO_2R^A$, and $SO_2NR^AR^B$;

$R^{16}$ and $R^{17}$ are each independently selected from hydrogen, F, Cl, $OR^A$, an optionally substituted $C_1$-$C_4$ alkyl, and an optionally substituted $C_1$-$C_4$ haloalkyl;

$R^A$ and $R^B$ are each independently selected from hydrogen, an optionally substituted $C_1$-$C_4$ alkyl, an optionally substituted $C_1$-$C_4$ haloalkyl, and an optionally substituted $C_1$-$C_4$ heteroalkyl;

$R^C$ is selected from an optionally substituted aryl and an optionally substituted heteroaryl that is optionally substituted with a substituent selected from F, Cl, Br, I, CN, $OR^A$, $NO_2$, $NR^AR^B$, $SR^A$, $SOR^A$, $SO_2R^A$, an optionally substituted $C_1$-$C_4$ alkyl, an optionally substituted $C_1$-$C_4$ haloalkyl, and an optionally substituted $C_1$-$C_4$ heteroalkyl;

$R^D$ is selected from hydrogen, an optionally substituted $C_1$-$C_4$ alkyl, an optionally substituted $C_1$-$C_4$ haloalkyl, and an optionally substituted $C_1$-$C_4$ heteroalkyl; and m is 1 or 2.

In certain embodiments, the compounds are selected with a proviso that at least one of $R^6$, $R^7$, $R^{10}$, and $R^{11}$ is other than hydrogen and at least one of $R^8$ and $R^9$ is other than hydrogen, alkyl, haloalkyl, alkenyl, and alkynyl. In certain embodiments, the compounds are selected with a proviso that at least one of $R^6$, $R^7$, $R^{10}$, and $R^{11}$ is other than hydrogen and at least one of $R^8$ and $R^9$ is heterohaloalkyl.

In other embodiments, the compounds provided herein have Formula I, where $R^1$ is $NO_2$ or CN; $R^2$ is hydrogen, an optionally substituted $C_1$-$C_4$ alkyl, or an optionally substituted $C_1$-$C_4$ haloalkyl; $R^{3a}$ is hydrogen or an optionally substituted $C_1$-$C_4$ alkyl; $R^4$, $R^6$, $R^7$, $R^{10}$ and $R^{11}$ are each hydrogen, an optionally substituted $C_1$-$C_6$ heterohaloalkyl, an optionally substituted $C_2$-$C_6$ heterohaloalkenyl or an optionally substituted $C_2$-$C_6$ heterohaloalkynyl, $R^5$ is hydrogen or an optionally substituted $C_1$-$C_4$ haloalkyl, $R^8$ is an optionally substituted $C_1$-$C_4$ haloalkyl; and $R^9$ is an optionally substituted $C_1$-$C_4$ haloalkyl.

In other embodiments, the compounds provided herein have Formula I, where $R^1$ IS $NO_2$ or CN. In other embodiments, $R^2$ is hydrogen, halo, an optionally substituted $C_1$-$C_4$ alkyl, or an optionally substituted $C_1$-$C_4$ haloalkyl. In other embodiments, $R^{3a}$ is hydrogen or an optionally substituted $C_1$-$C_4$ alkyl. In other embodiments, $R^4$, $R^6$, $R^7$, $R^{10}$ and $R^{11}$ are each hydrogen. In other embodiments, $R^5$ is hydrogen or an optionally substituted $C_1$-$C_4$ haloalkyl. In other embodiments, $R^8$ is an optionally substituted $C_1$-$C_4$ haloalkyl. In other embodiments, $R^9$ is an optionally substituted $C_1$-$C_4$ haloalkyl.

In other embodiments, $R^2$ is hydrogen, chloro, methyl or trifluoromethyl. In other embodiments, $R^{3a}$ is hydrogen or methyl. In other embodiments, $R^5$ is hydrogen or trifluoromethyl. In other embodiments, $R^8$ is 2,2,2-trifluoroethyl. In other embodiments, $R^9$ is 2,2,2-trifluoroethyl.

Compounds of Formula III

In other embodiments, the compounds have Formula III:

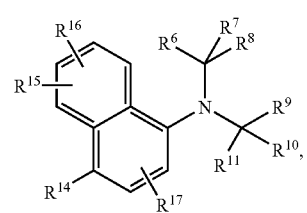

III wherein the variables are as described elsewhere herein.

In other embodiments, the compounds provided herein have Formula I, where $R^1$ and $R^2$ are each independently selected from hydrogen, F, Cl, Br, I, $OR^A$, $SR^A$, $NO_2$, CN, an optionally substituted $C_1$-$C_4$ alkyl, an optionally substituted $C_1$-$C_4$ haloalkyl, an optionally substituted $C_1$-$C_4$ heteroalkyl, $COR^A$, $CO_2R^A$, $CONR^AR^B$, $SOR^A$, $SO_2R^A$, and $SO_2NR^AR^B$, $NHCOR^A$, and $NHCONR^AR^B$, provided that at least one of $R^1$ and $R^2$ is not hydrogen;

$R^{3a}$, $R^4$, and $R^5$ are each independently selected from hydrogen, F, Cl, $OR^A$, an optionally substituted $C_1$-$C_4$ alkyl, and an optionally substituted $C_1$-$C_4$ haloalkyl;

wherein if $R^1$ is $NO_2$ and $R^{3a}$ is F, then at least one of $R^2$ and $R^4$ and $R^5$ is not hydrogen;

$R^6$, $R^7$, $R^{10}$, and $R^{11}$ are each independently selected from hydrogen, an optionally substituted $C_1$-$C_6$ alkyl, an optionally substituted $C_1$-$C_6$ haloalkyl, an optionally substituted $C_1$-$C_6$ heteroalkyl, an optionally substituted $C_1$-$C_6$ heterohaloalkyl, an optionally substituted $C_2$-$C_6$ heterohaloalkenyl, an optionally substituted $C_2$-$C_6$ heterohaloalkynyl, an optionally substituted $C_2$-$C_6$ alkynyl, and an optionally substituted $C_2$-$C_6$ alkenyl;

$R^8$ and $R^9$ are each independently selected from hydrogen, an optionally substituted $C_1$-$C_8$ alkyl, an optionally substituted $C_2$-$C_8$ alkenyl, an optionally substituted $C_1$-$C_8$ haloalkyl, an optionally substituted $C_2$-$C_8$ haloalkenyl, $C_1$-$C_8$ heteroalkyl, an optionally substituted $C_2$-$C_8$ heteroalkenyl, an optionally substituted $C_2$-$C_8$ alkynyl, an optionally substituted $C_2$-$C_8$ haloalkynyl, an optionally substituted $C_2$-$C_8$ heteroalkynyl, an optionally substituted $C_1$-$C_6$ heterohaloalkyl, an optionally substituted $C_2$-$C_6$ heterohaloalkenyl, an optionally substituted $C_2$-$C_6$ heterohaloalkynyl, an optionally substituted aryl, an optionally substituted heteroaryl, CH($R^D$)O$R^A$, CH($R^D$)N$R^A R^B$, and (CH$_2$)$_m R^C$;

$R^{14}$ and $R^{15}$ are each independently selected from hydrogen, F, Cl, Br, I, O$R^A$, S$R^A$, NO$_2$, CN, an optionally substituted $C_1$-$C_4$ alkyl, an optionally substituted $C_1$-$C_4$ haloalkyl, an optionally substituted $C_1$-$C_4$ heteroalkyl, NHCO$R^A$, NHCON$R^A R^B$, CO$R^A$, CO$_2 R^A$, CON$R^A R^B$, SO$R^A$, SO$_2 R^A$, and SO$_2$N$R^A R^B$;

$R^{16}$ and $R^{17}$ are each independently selected from hydrogen, F, Cl, O$R^4$, an optionally substituted $C_1$-$C_4$ alkyl, and an optionally substituted $C_1$-$C_4$ haloalkyl;

$R^A$ and $R^B$ are each independently selected from hydrogen, an optionally substituted $C_1$-$C_4$ alkyl, an optionally substituted $C_1$-$C_4$ haloalkyl, and an optionally substituted $C_1$-$C_4$ heteroalkyl;

$R^C$ is selected from an optionally substituted aryl and an optionally substituted heteroaryl that is optionally substituted with a substituent selected from F, Cl, Br, I, CN, O$R^A$, NO$_2$, N$R^A R^B$, S$R^A$, SO$R^A$, SO$_2 R^A$, an optionally substituted $C_1$-$C_4$ alkyl, an optionally substituted $C_1$-$C_4$ haloalkyl, and an optionally substituted $C_1$-$C_4$ heteroalkyl;

$R^D$ is selected from hydrogen, an optionally substituted $C_1$-$C_4$ alkyl, an optionally substituted $C_1$-$C_4$ haloalkyl, and an optionally substituted $C_1$-$C_4$ heteroalkyl; and m is 1 or 2.

In certain embodiments, the compounds of Formula III are selected with a proviso that at least one of $R^6$, $R^7$, $R^8$, $R^9$, $R^{10}$, and $R^{11}$ is selected from an optionally substituted $C_1$-$C_6$ heteroalkyl. In certain embodiments, the compounds of Formula III are selected with a proviso that at least one of $R^6$, $R^7$, $R^{10}$, and $R^{11}$ is other than hydrogen. In certain embodiments, the compounds of Formula III are selected with a proviso that at least one of $R^6$, $R^7$, $R^{10}$, and $R^{11}$ is other than hydrogen and at least one of $R^8$ and $R^9$ is other than hydrogen, alkyl, haloalkyl, alkenyl, and alkynyl. In certain embodiments, the compounds are selected with a proviso that at least one of $R^6$, $R^7$, $R^{10}$, and $R^{11}$ is other than hydrogen and at least one of $R^8$ and $R^9$ is heterohaloalkyl.

In embodiments in which two or more of a particular variable are present, the identities of those two or more particular variables are selected independently and, thus, may be the same or different from one another. For example, certain compounds provided herein contain two or more $R^A$ groups. The identities of those two or more $R^A$ groups are each selected independently. Thus, in certain embodiments, those $R^A$ groups are all the same as one another; in certain embodiments, those $R^A$ groups are all different from one another; and in certain embodiments, some of those $R^A$ groups are the same as one another and some are different from one another.

In certain embodiments, a compound of Formula I, Formula II, Formula III, Formula IV, Formula V, or Formula VI is a selective androgen receptor modulator. In certain embodiments, a compound of Formula I is a selective androgen receptor agonist. In certain embodiments, a compound of Formula I, Formula II, Formula III, Formula IV, Formula V, or Formula VI is a selective androgen receptor antagonist. In certain embodiments, a compound of Formula I, Formula II, Formula III, Formula IV, Formula V, or Formula VI is a selective androgen receptor partial agonist. In certain embodiments, a compound of Formula I, Formula II, Formula III, Formula IV, Formula V, or Formula VI is a tissue-specific selective androgen modulator. In certain embodiments, a compound of Formula I, Formula II, Formula III, Formula IV, Formula V, or Formula VI is a gene-specific selective androgen modulator. In certain embodiments, a compound of Formula I, Formula II, Formula III, Formula IV, Formula V, or Formula VI is a selective androgen receptor binding compound.

In certain embodiments, provided herein is a compound selected from:

N,N-bis(2,2,2-trifluoroethyl)-3-methyl-4-nitroaniline (compound 101);

N,N-bis(2,2,2-trifluoroethyl)-4-nitroaniline (compound 102);

4-Bromo-N,N-bis(2,2,2-trifluoroethyl)-3-(trifluoromethyl) aniline (compound 103$^a$);

4-(Bis(2,2,2-trifluoroethyl)amino)-2-(trifluoromethyl)benzonitrile (compound 103);

(5R)—N-(4-nitrophenyl)-5-(dimethyl-tort-butylsilyloxymethyl)-2-pyrrolidone (compound 104);

(5R)—N-(4-nitrophenyl)-5-(hydroxymethyl)-2-pyrrolidone (compound 105);

(2R)—N-(4-nitro-3-trifluoromethylphenyl)-2-(dimethyl-tert-butylsilyloxymethyl)pyrrolidine (compound 106);

(2R)—N-(4-nitro-3-trifluoromethylphenyl)-2-(hydroxymethyl)pyrrolidine (compound 108);

(2R)—N-(4-nitrophenyl)-2-(hydroxymethyl)pyrrolidine (compound 109);

(2R)—N-(3-Trifluoromethyl-4-nitrophenyl)-2-formylpyrrolidine (compound 110);

(2R)—N-(3-Trifluoromethyl-4-nitrophenyl)-2-(1-(S)-hydroxy-2,2,2-trifluoroethyl)pyrrolidine (compound 111);

(2R)—N-(3-Trifluoromethyl-4-nitrophenyl)-2-(1-(R)-hydroxy-2,2,2-trifluoroethyl)pyrrolidine (compound 112);

(2S)—N-(4-nitrophenyl)-2-(hydroxymethyl)pyrrolidine (compound 113);

(2R)—N-(4-nitrophenyl)-2-(1-(S)-hydroxy-2,2,2-trifluoroethyl)pyrrolidine (compound 114);

(2R)—N-(4-nitrophenyl)-2-(R)-(1-(R)-hydroxy-2,2,2-trifluoroethyl)pyrrolidine (compound 115);

(2S)—N-(4-nitrophenyl)-2-(1-(S)-hydroxy-2,2,2-trifluoroethyl)pyrrolidine (compound 116);

(2S)—N-(4-nitrophenyl)-2-(1-(R)-hydroxy-2,2,2-trifluoroethyl)pyrrolidine (compound 117);

3-(3-Methoxyphenyl)-6-nitro-2,7-dimethyl-1H-indole (compound 118);

4-[Bis-(2,2,2-trifluoroethyl)amino]-2-chloro-3-methyl-benzonitrile (compound 119);

cis-2,5-Dimethyl-1-(4-nitro-3-trifluoromethylphenyl)-pyrrolidine (compound 120);

trans-2,5-dimethyl-1-(4-nitro-3-trifluoromethylphenyl)-pyrrolidine (compound 121);

1-(4-Nitro-3-trifluoromethylphenyl)-piperidine-2-carboxylic acid ethyl ester (compound 122);

1-(4-Nitro-3-trifluoromethylphenyl)-4-(hydroxymethyl)-piperidine (compound 123);

(1-(3-trifluoromethyl-4-nitrophenyl)piperidin-2-yl)methyl acetate (compound 124);

4-(2-Hydroxymethyl-pyrrolidin-1-yl)-benzonitrile (compound 125);

4-Benzyl-2-hydroxymethyl-1-(4-nitro-3-trifluoromethylphenyl)-pyrrolidine (compound 126);

2-Fluoro-4-(2-hydroxymethyl-pyrrolidin-1-yl)-benzonitrile (compound 127);

4-Hydroxy-1-(4-nitrophenyl)-pyrrolidine-2-carboxylic acid ethyl ester (compound 128);

4-Hydroxy-1-(4-nitro-3-trifluoromethylphenyl)-pyrrolidine-2-carboxylic acid ethyl ester (compound 129);

5-Hydroxymethyl-1-(4-nitro-3-trifluoromethylphenyl)-pyrrolidin-3-ol (compound 130);

2-(Aminomethyl)-1-(4-Nitro-3-trifluoromethylphenyl)-pyrrolidine (compound 131);

4-Hydroxy-1-(4-nitrophenyl)-pyrrolidine-2-carboxylic acid (compound 132); and

4-Hydroxy-1-(4-nitro-3-trifluoromethylphenyl)-pyrrolidine-2-carboxylic acid (compound 133); or pharmaceutically acceptable salts, esters, amides, and prodrugs thereof.

In other embodiments, provided herein is a compound selected from: N,N'-bis(2,2,2-trifluoroethyl)-3-methyl-4-nitroaniline; N,N'-bis(2,2,2-trifluoroethyl)-4-nitroaniline; 5-(2,2,2-trifluoroethyl)amino-2-bromobenzotrifluoride; 4-N,N'-bis(2,2,2-trifluoroethyl)amino-2-trifluoromethylbenzonitrile; (R)—N-4-nitrophenyl-5-(dimethyl-tert-butylsilyloxymethyl)-2-pyrrolidone; (R)—N-4-nitrophenyl-5-hydroxymethyl-2-pyrrolidone; (R)—N-(4-nitro-3-trifluoromethylphenyl)-2-dimethyl-tert-butylsilyloxymethylpyrrolidine; (R)—N-(4-nitro-3-trifluoromethylphenyl)-2-hydroxymethylpyrrolidine; (R)—N-(4-nitrophenyl)-2-hydroxymethylpyrrolidine; (R)—N-(3-Trifluoromethyl-4-nitrophenyl)-2-formylpyrrolidine; N-(3-Trifluoromethyl-4-nitrophenyl)-2-(R)-(1-(S)-hydroxy-2,2,2-trifluoroethyl)pyrrolidine; N-(3-Trifluoromethyl-4-nitrophenyl)-2-(R)-(1-(R)—hydroxy-2,2,2-trifluoroethyl)pyrrolidine; (S)—N-(4-nitrophenyl)-2-hydroxymethylpyrrolidine; N-(4-nitrophenyl)-2-(R)-(1-(S)-hydroxy-2,2,2-trifluoroethyl)pyrrolidine; N-(4-nitrophenyl)-2-(R)-(1-(R)-hydroxy-2,2,2-trifluoroethyl); N-(4-nitrophenyl)-2-(S)-(1-(S)-hydroxy-2,2,2-trifluoroethyl)pyrrolidine; and N-(4-nitrophenyl)-2-(S)-(1-(R)-hydroxy-2,2,2-trifluoroethyl)pyrrolidine; and a pharmaceutically acceptable salt, ester, amide, or prodrug of any of those compounds.

Certain compounds provided herein can exist as stereoisomers including optical isomers. The present disclosure is intended to include all stereoisomers and both the racemic mixtures of such stereoisomers as well as the individual enantiomers that can be separated according to methods that are known in the art.

C. Preparation of the Compounds

In certain embodiments, of the compounds provided herein can be synthesized using the following synthesis schemes. In each of the Schemes the R groups correspond to the definitions described above.

anilines (e.g., Structure 1) with an aldehyde or ketone or acid in the presence of a reducing agent, such as sodium cyanoborohydride or sodium borohydride affords compounds of Structure 2. Alternatively, treatment of the substituted anilines of Structure 1 with an organohalide in the presence of a base provides the compounds of Structure 2.

Scheme II

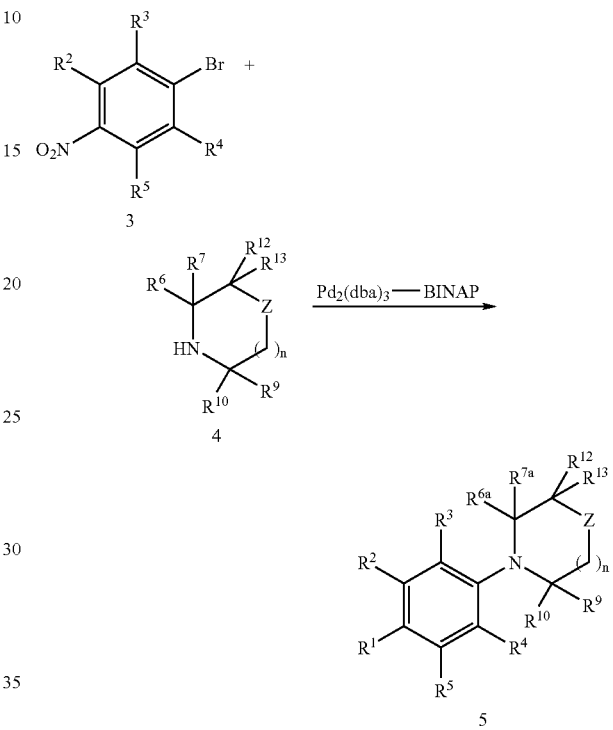

Scheme II describes the preparation of compounds of Structure 5 from the substituted aryl halides such as Structure 3. Palladium catalyzed coupling reaction of Structure 3 and compounds of Structure 4 provide the products of Structure 5.

Scheme I

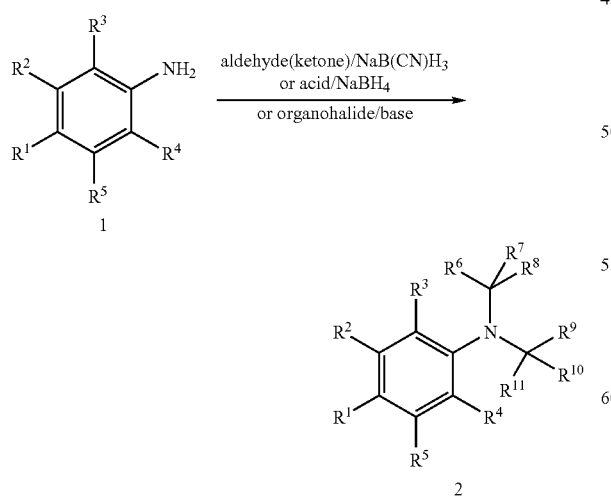

Scheme I describes the alkylation of the substituted anilines such as Structure 1. Reductive alkylation of the substituted Scheme III

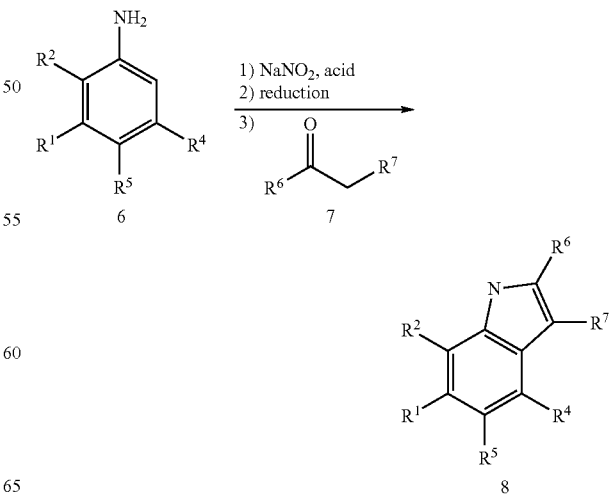

Scheme III describes the indole synthesis from substituted anilines such as Structure 6. Diazotization of the substituted anilines (e.g., Structure 6) followed by treatment with a reducing agent, such tin dichloride affords the corresponding hydrazine. Treatment of the hydrazines with a ketone, such as Structure 7, under acidic conditions affords the indoles of Structure 8.

Scheme IV

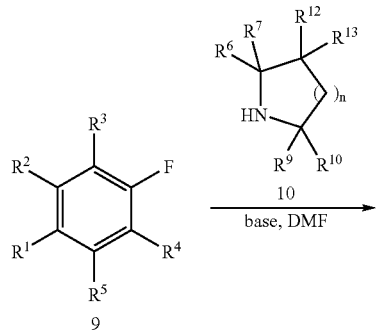

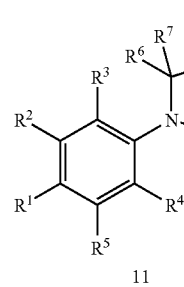

Scheme IV describes the substitution reaction of aromatic fluorides of Structure 9 with amines such as Structure 10 to give compounds of Structure 11.

Scheme V

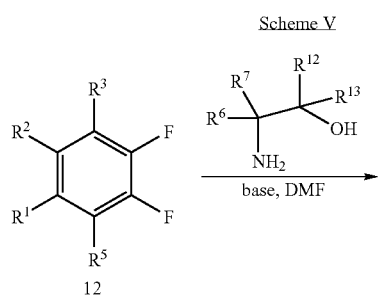

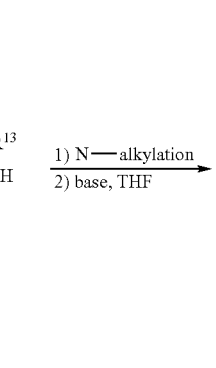

-continued

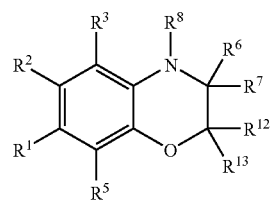

Scheme V describes the substitution reaction of aromatic fluorides of Structure 12 with amino alcohols to give compounds of Structure 13. Alkylation of the nitrogen atom, followed by cyclization gives the substituted benzoxazines of Structure 14.

Scheme VI

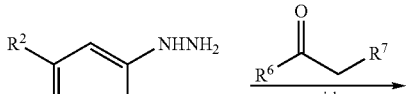

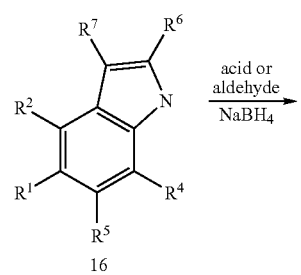

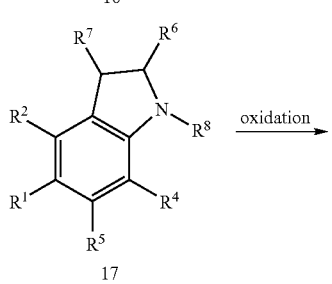

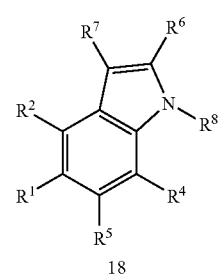

Scheme V describes the synthesis of indoles of structure 16, from hydrazines such as 15. Alkylation of the nitrogen atom under reductive conditions gives the indolines of Structure 17. These can be oxidized to the N-alkylated indoles of Structure 18.

Scheme VII

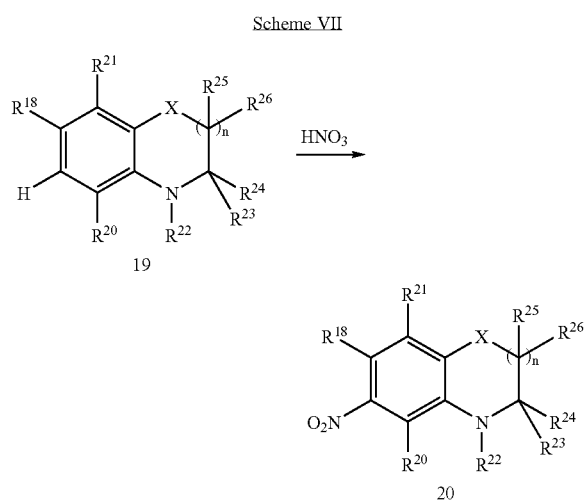

Scheme VII describes the nitration reaction of fused heterocyclic aromatics of Structure 19 with nitric acid to give compounds of Structure 20.

In certain embodiments, provided herein is a salt corresponding to any of the compounds provided herein. In certain embodiments, the salt corresponding to a selective androgen receptor modulator or selective androgen binding agent is provided herein. In certain embodiments, a salt is obtained by reacting a compound with an inorganic acid, such as hydrochloric acid, hydrobromic acid, sulfuric acid, nitric acid, phosphoric acid, methanesulfonic acid, ethanesulfonic acid, p-toluenesulfonic acid, salicylic acid, and the like. In certain embodiments, a salt is obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)-methylamine, and salts with amino acids such as arginine, lysine, and the like.

In certain embodiments, one or more carbon atoms of a compound provided herein is replaced with silicon. See e.g., WO 03/037905A1; Tacke and Zilch, Endeavour, New Series, 10, 191-197 (1986); Bains and Tacke, Curr. Opin. Drug Discov Devel. July: 6(4):526-43 (2003). In certain embodiments, compounds provided herein containing one or more silicon atoms possess certain desired properties, including, but not limited to, greater stability and/or longer half-life in a patient, when compared to the same compound in which none of the carbon atoms have been replaced with a silicon atom.

D. Formulation of Pharmaceutical Compositions

The pharmaceutical compositions provided herein contain therapeutically effective amounts of one or more of the androgen receptor activity modulators provided herein that are useful in the prevention, treatment, or amelioration of one or more of the symptoms of diseases or disorders associated with androgen receptor activity. Such prevention, treatment, or amelioration of diseases or disorders include, but are not limited to, maintenance of muscle strength and function (e.g., in the elderly); reversal or prevention of frailty or age-related functional decline ("ARFD") in the elderly (e.g., sarcopenia); treatment of catabolic side effects of glucocorticoids; prevention and/or treatment of reduced bone mass, density or growth (e.g., osteoporosis and osteopenia); treatment of chronic fatigue syndrome (CFS); chronic myalgia; treatment of acute fatigue syndrome and muscle loss following elective surgery (e.g., post-surgical rehabilitation); accelerating of wound healing; accelerating bone fracture repair (such as accelerating the recovery of hip fracture patients); accelerating healing of complicated fractures, e.g. distraction osteogenesis; in joint replacement; prevention of post-surgical adhesion formation; acceleration of tooth repair or growth; maintenance of sensory function (e.g., hearing, sight, olefaction and taste); treatment of periodontal disease; treatment of wasting secondary to fractures and wasting in connection with chronic obstructive pulmonary disease (COPD), chronic liver disease, AIDS, weightlessness, cancer cachexia, burn and trauma recovery, chronic catabolic state (e.g., coma), eating disorders (e.g., anorexia) and chemotherapy; treatment of cardiomyopathy; treatment of thrombocytopenia; treatment of growth retardation in connection with Crohn's disease; treatment of short bowel syndrome; treatment of irritable bowel syndrome; treatment of inflammatory bowel disease; treatment of Crohn's disease and ulcerative colitis; treatment of complications associated with transplantation; treatment of physiological short stature including growth hormone deficient children and short stature associated with chronic illness; treatment of obesity and growth retardation associated with obesity; treatment of anorexia (e.g., associated with cachexia or aging); treatment of hypercortisolism and Cushing's syndrome; Paget's disease; treatment of osteoarthritis; induction of pulsatile growth hormone release; treatment of osteochondrodysplasias; treatment of depression, nervousness, irritability and stress; treatment of reduced mental energy and low self-esteem (e.g., motivation/assertiveness); improvement of cognitive function (e.g., the treatment of dementia, including Alzheimer's disease and short term memory loss); treatment of catabolism in connection with pulmonary dysfunction and ventilator dependency; treatment of cardiac dysfunction (e.g., associated with valvular disease, myocardial infarction, cardiac hypertrophy or congestive heart failure); lowering blood pressure; protection against ventricular dysfunction or prevention of reperfusion events; treatment of adults in chronic dialysis; reversal or slowing of the catabolic state of aging; attenuation or reversal of protein catabolic responses following trauma (e.g., reversal of the catabolic state associated with surgery, congestive heart failure, cardiac myopathy, burns, cancer, COPD etc.); reducing cachexia and protein loss due to chronic illness such as cancer or AIDS; treatment of hyperinsulinemia including nesidioblastosis; treatment of immunosuppressed patients; treatment of wasting in connection with multiple sclerosis or other neurodegenerative disorders; promotion of myelin repair; maintenance of skin thickness; treatment of metabolic homeostasis and renal homeostasis (e.g., in the frail elderly); stimulation of osteoblasts, bone remodeling and cartilage growth; regulation of food intake; treatment of insulin resistance, including NIDDM, in mammals (e.g., humans); treatment of insulin resistance in the heart; improvement of sleep quality and correction of the relative hyposomatotropism of senescence due to high increase in REM sleep and a decrease in REM latency; treatment of hypothermia; treatment of congestive heart failure; treatment of lipodystrophy (e.g., in patients taking HIV or AIDS therapies such as protease inhibitors); treatment of muscular atrophy (e.g., due to physical inactivity, bed rest or reduced weight-bearing conditions); treatment of musculoskeletal impairment (e.g., in the elderly); improvement of the overall pulmonary function; treatment of sleep disorders; and the treatment of the catabolic state of prolonged critical illness; treatment of hirsutism, acne, seborrhea, androgenic alopecia, anemia, hyperpilosity, benign prostate hypertrophy, adenomas and neoplasies of the prostate (e.g., advanced metastatic prostate cancer) and malignant tumor cells containing the androgen receptor, such as is the case for breast, brain, skin, ovarian, bladder, lymphatic, liver and kidney cancers; cancers of the skin, pancreas, endometrium, lung and colon; osteosarcoma; hypercalcemia of malignancy; metastatic bone disease; treatment of spermatogenesis, endometriosis and polycystic ovary syndrome; counteracting preeclampsia, eclampsia of pregnancy and preterm labor; treatment of premenstrual syndrome; treatment of vaginal dryness; age related decreased testosterone levels in men, male menopause, hypogonadism, male hormone replacement, male and female sexual dysfunction (e.g., erectile dysfunction, decreased sex drive, sexual well-being, decreased libido), male and female contraception, hair loss, Reaven's Syndrome and the enhancement of bone and muscle performance/strength.

The compositions contain one or more compounds provided herein. The compounds are formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers. Typically the compounds described above are formulated into pharmaceutical compositions using techniques and procedures well known in the art (see, e.g., Ansel *Introduction to Pharmaceutical Dosage Forms, Fourth Edition* 1985, 126).

In certain embodiments, a pharmaceutical composition containing one or more compounds provided herein is prepared using known techniques, including, but not limited to mixing, dissolving, granulating, dragee-making, levigating, emulsifying, encapsulating, entrapping or tabletting processes.

In the compositions, effective concentrations of one or more compounds or pharmaceutically acceptable derivatives is (are) mixed with a suitable pharmaceutical carrier or vehicle. The compounds can be derivatized as the corresponding salts, esters, enol ethers or esters, acids, bases, solvates, hydrates or prodrugs prior to formulation, as described above. The concentrations of the compounds in the compositions are effective for delivery of an amount, upon administration, that treats, prevents, or ameliorates one or more of the symptoms of diseases or disorders associated with androgen activity or in which androgen activity is implicated. Such prevention, treatment, or amelioration diseases or disorders include, but are not limited to, maintenance of muscle strength and function (e.g., in the elderly); reversal or prevention of frailty or age-related functional decline ("ARFD") in the elderly (e.g., sarcopenia); treatment of catabolic side effects of glucocorticoids; prevention and/or treatment of reduced bone mass, density or growth (e.g., osteoporosis and osteopenia); treatment of chronic fatigue syndrome (CFS); chronic myalgia; treatment of acute fatigue syndrome and muscle loss following elective surgery (e.g., post-surgical rehabilitation); accelerating of wound healing; accelerating bone fracture repair (such as accelerating the recovery of hip fracture patients); accelerating healing of complicated fractures, e.g. distraction osteogenesis; in joint replacement; prevention of post-surgical adhesion formation; acceleration of tooth repair or growth; maintenance of sensory function (e.g., hearing, sight, olefaction and taste); treatment of periodontal disease; treatment of wasting secondary to fractures and wasting in connection with chronic obstructive pulmonary disease (COPD), chronic liver disease, AIDS, weightlessness, cancer cachexia, burn and trauma recovery, chronic catabolic state (e.g., coma), eating disorders (e.g., anorexia) and chemotherapy; treatment of cardiomyopathy; treatment of thrombocytopenia; treatment of growth retardation in connection with Crohn's disease; treatment of short bowel syndrome; treatment of irritable bowel syndrome; treatment of inflammatory bowel disease; treatment of Crohn's disease and ulcerative colitis; treatment of complications associated with transplantation; treatment of physiological short stature including growth hormone deficient children and short stature associated with chronic illness; treatment of obesity and growth retardation associated with obesity; treatment of anorexia (e.g., associated with cachexia or aging); treatment of hypercortisolism and Cushing's syndrome; Paget's disease; treatment of osteoarthritis; induction of pulsatile growth hormone release; treatment of osteochondrodysplasias; treatment of depression, nervousness, irritability and stress; treatment of reduced mental energy and low self-esteem (e.g., motivation/assertiveness); improvement of cognitive function (e.g., the treatment of dementia, including Alzheimer's disease and short term memory loss); treatment of catabolism in connection with pulmonary dysfunction and ventilator dependency; treatment of cardiac dysfunction (e.g., associated with valvular disease, myocardial infarction, cardiac hypertrophy or congestive heart failure); lowering blood pressure; protection against ventricular dysfunction or prevention of reperfusion events; treatment of adults in chronic dialysis; reversal or slowing of the catabolic state of aging; attenuation or reversal of protein catabolic responses following trauma (e.g., reversal of the catabolic state associated with surgery, congestive heart failure, cardiac myopathy, burns, cancer, COPD etc.); reducing cachexia and protein loss due to chronic illness such as cancer or AIDS; treatment of hyperinsulinemia including nesidioblastosis; treatment of immunosuppressed patients; treatment of wasting in connection with multiple sclerosis or other neurodegenerative disorders; promotion of myelin repair; maintenance of skin thickness; treatment of metabolic homeostasis and renal homeostasis (e.g., in the frail elderly); stimulation of osteoblasts, bone remodeling and cartilage growth; regulation of food intake; treatment of insulin resistance, including NIDDM, in mammals (e.g., humans); treatment of insulin resistance in the heart; improvement of sleep quality and correction of the relative hyposomatotropism of senescence due to high increase in REM sleep and a decrease in REM latency; treatment of hypothermia; treatment of congestive heart failure; treatment of lipodystrophy (e.g., in patients taking HIV or AIDS therapies such as protease inhibitors); treatment of muscular atrophy (e.g., due to physical inactivity, bed rest or reduced weight-bearing conditions); treatment of musculoskeletal impairment (e.g., in the elderly); improvement of the overall pulmonary function; treatment of sleep disorders; and the treatment of the catabolic state of prolonged critical illness; treatment of hirsutism, acne, seborrhea, androgenic alopecia, anemia, hyperpilosity, benign prostate hypertrophy, adenomas and neoplasies of the prostate (e.g., advanced metastatic prostate cancer) and malignant tumor cells containing the androgen receptor, such as is the case for breast, brain, skin, ovarian, bladder, lymphatic, liver and kidney cancers; cancers of the skin, pancreas, endometrium, lung and colon; osteosarcoma; hypercalcemia of malignancy; metastatic bone disease; treatment of spermatogenesis, endometriosis and polycystic ovary syndrome; counteracting preeclampsia, eclampsia of pregnancy and preterm labor; treatment of premenstrual syndrome; treatment of vaginal dryness; age related decreased testosterone levels in men, male menopause, hypogonadism, male hormone replacement, male and female sexual dysfunction (e.g., erectile dysfunction, decreased sex drive, sexual well-being, decreased libido), male and female contraception, hair loss, Reaven's Syndrome and the enhancement of bone and muscle performance/strength.

Typically, the compositions are formulated for single dosage administration. To formulate a composition, the weight fraction of compound is dissolved, suspended, dispersed or otherwise mixed in a selected vehicle at an effective concentration such that the treated condition is relieved or ameliorated. Pharmaceutical carriers or vehicles suitable for administration of the compounds provided herein include any such carriers known to those skilled in the art to be suitable for the particular mode of administration.

In addition, the compounds can be formulated as the sole pharmaceutically active ingredient in the composition or can be combined with other active ingredients. Liposomal suspensions, including tissue-targeted liposomes, such as tumor-targeted liposomes, can also be suitable as pharmaceutically acceptable carriers. These can be prepared according to methods known to those skilled in the art. For example, liposome formulations can be prepared as described in U.S. Pat. No. 4,522,811. Briefly, liposomes such as multilamellar vesicles (MLV's) can be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

The active compound is included in the pharmaceutically acceptable carrier in an amount sufficient to exert a therapeutically useful effect in the absence of undesirable side effects on the patient treated.

The concentration of active compound in the pharmaceutical composition will depend on absorption, inactivation and excretion rates of the active compound, the physicochemical characteristics of the compound, the dosage schedule, and amount administered as well as other factors known to those of skill in the art. For example, the amount that is delivered is sufficient to ameliorate one or more of the symptoms of diseases or disorders associated with androgen activity or in which androgen activity is implicated, as described herein.

The effective amount of a compound provided herein can be determined by one of ordinary skill in the art, and includes exemplary dosage amounts for a mammal of from about 0.05 to 100 mg/kg of body weight of active compound per day, which can be administered in a single dose or in the form of individual divided doses, such as from 1 to 4 times per day. It will be understood that the specific dose level and frequency of dosage for any particular subject can be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition.

The active ingredient can be administered at once, or can be divided into a number of smaller doses to be administered at intervals of time. It is understood that the precise dosage and duration of treatment is a function of the disease being treated and can be determined empirically using known testing protocols or by extrapolation from in vivo or in vitro test data. It is to be noted that concentrations and dosage values can also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the compounds, compositions, methods and other subject matter provided herein.

Pharmaceutically acceptable derivatives include acids, bases, enol ethers and esters, salts, esters, hydrates, solvates and prodrug forms. The derivative is selected such that its pharmacokinetic properties are superior to the corresponding neutral compound.

Thus, effective concentrations or amounts of one or more of the compounds described herein or pharmaceutically acceptable derivatives thereof are mixed with a suitable pharmaceutical carrier or vehicle for systemic, topical or local administration to form pharmaceutical compositions. Compounds are included in an amount effective for ameliorating one or more symptoms of, or for treating or preventing diseases or disorders associated with androgen receptor activity or in which androgen receptor activity is implicated, as described herein. The concentration of active compound in the composition will depend on absorption, inactivation, excretion rates of the active compound, the dosage schedule, amount administered, particular formulation as well as other factors known to those of skill in the art.

The compositions are intended to be administered by a suitable route, including orally in the form of capsules, tablets, granules, powders or liquid formulations including syrups; parenterally, such as subcutaneously, intravenously, intramuscularly, with intersternal injection or infusion techniques (as sterile injectable aq. or non-aq. solutions or suspensions); nasally such as by inhalation spray; topically, such as in the form of a cream or ointment; rectally such as in the form of suppositories; liposomally; and locally. The compositions can be in liquid, semi-liquid or solid form and are formulated in a manner suitable for each route of administration. In certain embodiments, administration of the formulation include parenteral and oral modes of administration. In one embodiment, the compositions are administered orally.

In certain embodiments, the pharmaceutical compositions provided herein containing one or more compounds provided herein is a solid (e.g., a powder, tablet, and/or capsule). In certain of such embodiments, a solid the pharmaceutical composition containing one or more compounds provided herein is prepared using ingredients known in the art, including, but not limited to, starches, sugars, diluents, granulating agents, lubricants, binders, and disintegrating agents.

In certain embodiments, a pharmaceutical composition containing one or more compounds provided herein is formulated as a depot preparation. Certain of such depot preparations are typically longer acting than non-depot preparations. In certain embodiments, such preparations are administered by implantation (for example subcutaneously or intramuscularly) or by intramuscular injection. In certain embodiments, depot preparations are prepared using suitable polymeric or hydrophobic materials (for example an emulsion in an acceptable oil) or ion exchange resins, or as sparingly soluble derivatives, for example, as a sparingly soluble salt.

In certain embodiments, a pharmaceutical composition containing one or more compounds provided herein contains a delivery system. Examples of delivery systems include, but are not limited to, liposomes and emulsions. Certain delivery systems are useful for preparing certain pharmaceutical compositions including those containing hydrophobic compounds. In certain embodiments, certain organic solvents such as dimethylsulfoxide are used.

In certain embodiments, a pharmaceutical composition containing one or more compounds provided herein contains one or more tissue-specific delivery molecules designed to deliver the pharmaceutical composition to specific tissues or cell types. For example, in certain embodiments, pharmaceutical compositions include liposomes coated with a tissue-specific antibody.

In certain embodiments, a pharmaceutical composition containing one or more compounds provided herein contains a co-solvent system. Certain of such co-solvent systems contain, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol containing 3% w/v benzyl alcohol, 8% w/v of the nonpolar surfactant Polysorbate 80™, and 65% w/v polyethylene glycol 300. The proportions of such co-solvent systems may be varied considerably without significantly altering their solubility and toxicity characteristics. Furthermore, the identity of co solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, solutions or suspensions used for parenteral, intradermal, subcutaneous, or topical application can include any of the following components: a sterile diluent, such as water for injection, saline solution, fixed oil, polyethylene glycol, glycerine, propylene glycol or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of tonicity such as sodium chloride or dextrose. Parenteral preparations can be enclosed in ampules, disposable syringes or single or multiple dose vials made of glass, plastic or other suitable material.

In instances in which the compounds exhibit insufficient solubility, methods for solubilizing compounds can be used. Such methods are known to those of skill in this art, and include, but are not limited to, using cosolvents, such as dimethylsulfoxide (DMSO), using surfactants, such as TWEEN®, or dissolution in aqueous sodium bicarbonate. Derivatives of the compounds, such as prodrugs of the compounds can also be used in formulating effective pharmaceutical compositions.

In certain embodiments, a pharmaceutical composition containing one or more compounds provided herein contains a sustained-release system. A non-limiting example of such a sustained-release system is a semipermeable matrix of solid hydrophobic polymers. In certain embodiments, sustained release systems may, depending on their chemical nature, release compounds over a period of hours, days, weeks or months.

In certain embodiments, upon mixing or addition of the compound(s), the resulting mixture can be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and can be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil-water emulsions containing suitable quantities of the compounds or pharmaceutically acceptable derivatives thereof. The pharmaceutically active compounds and derivatives thereof are typically formulated and administered in unit-dosage forms or multiple-dosage forms. Unit-dose forms as used herein refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampoules and syringes and individually packaged tablets or capsules. Unit-dose forms can be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

The composition can contain along with the active ingredient: a diluent such as lactose, sucrose, dicalcium phosphate, or carboxymethylcellulose; a lubricant, such as magnesium stearate, calcium stearate and talc; and a binder such as starch, natural gums, such as gum acaciagelatin, glucose, molasses, polyinylpyrrolidine, celluloses and derivatives thereof, povidone, crospovidones and other such binders known to those of skill in the art. Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered can also contain minor amounts of nontoxic auxiliary substances such as wetting agents, emulsifying agents, or solubilizing agents, pH buffering agents and the like, for example, acetate, sodium citrate, cyclodextrin derivatives, sorbitan monolaurate, triethanolamine sodium acetate, triethanolamine oleate, and other such agents. Actual methods of preparing such dosage forms are known, or will be apparent, to those skilled in this art; for example, see Remington's Pharmaceutical Sciences, Mack Publishing Company, Easton, Pa., 15th Edition, 1975. The composition or formulation to be administered will, in any event, contain a quantity of the active compound in an amount sufficient to alleviate the symptoms of the treated subject.

Dosage forms or compositions containing active ingredient in the range of 0.005% to 100% with the balance made up from non-toxic carrier can be prepared. For oral administration, a pharmaceutically acceptable non-toxic composition is formed by the incorporation of any of the normally employed excipients, such as, for example pharmaceutical grades of mannitol, lactose, starch, magnesium stearate, talcum, cellulose derivatives, sodium crosscarmellose, glucose, sucrose, magnesium carbonate or sodium saccharin. Such compositions include solutions, suspensions, tablets, capsules, powders and sustained release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparation of these compositions are known to those skilled in the art. The contemplated compositions can contain 0.001%-100% active ingredient, in one embodiment 0.1-85%, in another embodiment 75-95%.

In certain embodiments, the compounds can be administered in a form suitable for immediate release or extended release. Immediate release or extended release can be achieved with suitable pharmaceutical compositions or, particularly in the case of extended release, with devices such as subcutaneous implants or osmotic pumps. Exemplary compositions for topical administration include a topical carrier such as PLASTIBASE® (mineral oil gelled with polyethylene).

In certain embodiments, compounds used in the pharmaceutical compositions may be provided as pharmaceutically acceptable salts with pharmaceutically compatible counterions. Pharmaceutically compatible salts may be formed with many acids, including but not limited to hydrochloric acid, sulfuric acid, acetic acid, lactic acid, tartaric acid, malic acid, succinic acid, etc.

In certain embodiments, the pharmaceutical compositions contain a compound provided herein in a therapeutically effective amount. In certain embodiments, the therapeutically effective amount is sufficient to prevent, alleviate or ameliorate symptoms of a disease or to prolong the survival of the subject being treated. Determination of a therapeutically effective amount is well within the capability of those skilled in the art.

The compositions can include other active compounds to obtain desired combinations of properties. The compounds provided herein, or pharmaceutically acceptable derivatives thereof as described herein, can also be advantageously administered for therapeutic or prophylactic purposes together with another pharmacological agent known in the general art to be of value in treating one or more of the diseases or medical conditions referred to hereinabove, such as diseases or disorders associated with androgen receptor activity or in which androgen receptor activity is implicated. It is to be understood that such combination therapy constitutes a further aspect of the compositions and methods of treatment provided herein.

In certain embodiments, a pharmaceutical composition containing one or more compounds provided herein is formulated as a prodrug. In certain embodiments, prodrugs are useful because they are easier to administer than the corresponding active form. For example, in certain instances, a prodrug may be more bioavailable (e.g., through oral administration) than is the corresponding active form. In certain instances, a prodrug may have improved solubility compared to the corresponding active form. In certain embodiments, a prodrug is an ester. In certain embodiments, such prodrugs are less water soluble than the corresponding active form. In certain instances, such prodrugs possess superior transmittal across cell membranes, where water solubility is detrimental to mobility. In certain embodiments, the ester in such prodrugs is metabolically hydrolyzed to carboxylic acid. In certain instances the carboxylic acid containing compound is the corresponding active form. In certain embodiments, a prodrug contains a short peptide (polyaminoacid) bound to an acid group. In certain of such embodiments, the peptide is metabolized to form the corresponding active form.

In certain embodiments, a pharmaceutical composition containing one or more compounds provided herein is useful for treating a conditions or disorder in a mammalian, and particularly in a human patient. Suitable administration routes include, but are not limited to, oral, rectal, transmucosal, intestinal, enteral, topical, suppository, through inhalation, intrathecal, intraventricular, intraperitoneal, intranasal, intraocular and parenteral (e.g., intravenous, intramuscular, intramedullary, and subcutaneous). In certain embodiments, pharmaceutical compositions are administered to achieve local rather than systemic exposures. For example, pharmaceutical compositions may be injected directly in the area of desired effect (e.g., in the renal or cardiac area). In certain embodiments in which the pharmaceutical composition is administered locally, the dosage regimen is adjusted to achieve a desired local concentration of a compound provided herein.

In certain embodiments, a pharmaceutical composition containing one or more compounds provided herein is administered in the form of a dosage unit (e.g., tablet, capsule, bolus, etc.). In certain embodiments, such dosage units contain a selective androgen receptor modulator in a dose from about 1 µg/kg of body weight to about 50 mg/kg of body weight. In certain embodiments, such dosage units contain a selective androgen receptor modulator in a dose from about 2 µg/kg of body weight to about 25 mg/kg of body weight. In certain embodiments, such dosage units contain a selective androgen receptor modulator in a dose from about 10 µg/kg of body weight to about 5 mg/kg of body weight. In certain embodiments, pharmaceutical compositions are administered as needed, once per day, twice per day, three times per day, or four or more times per day. It is recognized by those skilled in the art that the particular dose, frequency, and duration of administration depends on a number of factors, including, without limitation, the biological activity desired, the condition of the patient, and tolerance for the pharmaceutical composition.

In certain embodiments, a pharmaceutical composition provided herein is administered for a period of continuous therapy. For example, a pharmaceutical composition provided herein may be administered over a period of days, weeks, months, or years.

Dosage amount, interval between doses, and duration of treatment may be adjusted to achieve a desired effect. In certain embodiments, dosage amount and interval between doses are adjusted to maintain a desired concentration of compound in a patient. For example, in certain embodiments, dosage amount and interval between doses are adjusted to provide plasma concentration of a compound provided herein at an amount sufficient to achieve a desired effect. In certain of such embodiments the plasma concentration is maintained above the minimal effective concentration (MEC). In certain embodiments, pharmaceutical compositions provided herein are administered with a dosage regimen designed to maintain a concentration above the MEC for 10-90% of the time, between 30-90% of the time, or between 50-90% of the time.

1. Compositions for Oral Administration

In certain embodiments, oral pharmaceutical dosage forms are either solid, gel or liquid. The solid dosage forms are tablets, capsules, granules, and bulk powders. Types of oral tablets include compressed, chewable lozenges and tablets which can be enteric-coated, sugar-coated or film-coated. Capsules can be hard or soft gelatin capsules, while granules and powders can be provided in non-effervescent or effervescent form with the combination of other ingredients known to those skilled in the art.

In certain embodiments, the formulations are solid dosage forms, preferably capsules or tablets. The tablets, pills, capsules, troches and the like can contain any of the following ingredients, or compounds of a similar nature: a binder; a diluent; a disintegrating agent; a lubricant; a glidant; a sweetening agent; and a flavoring agent.

In certain embodiments, pharmaceutical compositions for oral administration are push fit capsules made of gelatin. Certain of such push fit capsules contain one or more compounds provided herein in admixture with one or more filler such as lactose, binders such as starches, and/or lubricants such as talc or magnesium stearate and, optionally, stabilizers. In certain embodiments, pharmaceutical compositions for oral administration are soft, sealed capsules made of gelatin and a plasticizer, such as glycerol or sorbitol. In certain soft capsules, one or more compounds provided are to be dissolved or suspended in suitable liquids, such as fatty oils, liquid paraffin, or liquid polyethylene glycols. In addition, stabilizers may be added.

In certain embodiments, pharmaceutical compositions are prepared for buccal administration. Certain of such pharmaceutical compositions are tablets or lozenges formulated in conventional manner.

Examples of binders for use in the compositions provided herein include microcrystalline cellulose, gum tragacanth, glucose solution, acacia mucilage, gelatin solution, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, sodium alginate, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic-coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

If oral administration is desired, the compound could be provided in a composition that protects it from the acidic environment of the stomach. For example, the composition can be formulated in an enteric coating that maintains its integrity in the stomach and releases the active compound in the intestine. The composition can also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup can contain, in addition to the active compounds, sucrose as a sweetening agent and certain preservatives, dyes and colorings and flavors.

The active materials can also be mixed with other active materials which do not impair the desired action, or with materials that supplement the desired action, such as antacids, H2 blockers, and diuretics. The active ingredient is a compound or pharmaceutically acceptable derivative thereof as described herein. Higher concentrations, up to about 98% by weight of the active ingredient can be included.

Pharmaceutically acceptable carriers included in tablets are binders, lubricants, diluents, disintegrating agents, coloring agents, flavoring agents, and wetting agents. Enteric-coated tablets, because of the enteric-coating, resist the action of stomach acid and dissolve or disintegrate in the neutral or alkaline intestines. Sugar-coated tablets are compressed tablets to which different layers of pharmaceutically acceptable substances are applied. Film-coated tablets are compressed tablets which have been coated with a polymer or other suitable coating. Multiple compressed tablets are compressed tablets made by more than one compression cycle utilizing the pharmaceutically acceptable substances previously mentioned. Coloring agents can also be used in the above dosage forms. Flavoring and sweetening agents are used in compressed tablets, sugar-coated, multiple compressed and chewable tablets. Flavoring and sweetening agents are especially useful in the formation of chewable tablets and lozenges.

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Pharmaceutically acceptable carriers used in elixirs include solvents. Syrups are concentrated aqueous solutions of a sugar, for example, sucrose, and can contain a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic acid, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Diluents include lactose and sucrose. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic acids include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation.

For a solid dosage form, the solution or suspension, in for example propylene carbonate, vegetable oils or triglycerides, is preferably encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, can be diluted with a sufficient quantity of a pharmaceutically acceptable liquid carrier, e.g., water, to be easily measured for administration.

Alternatively, liquid or semi-solid oral formulations can be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. Nos. Re 28,819 and 4,358,603. Briefly, such formulations include, but are not limited to, those containing a compound provided herein, a dialkylated mono- or poly-alkylene glycol, including, but not limited to, 1,2-dimethoxymethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl)acetals of lower alkyl aldehydes such as acetaldehyde diethyl acetal.

In all embodiments, tablets and capsules formulations can be coated as known by those of skill in the art in order to modify or sustain dissolution of the active ingredient. Thus, for example, they can be coated with a conventional enterically digestible coating, such as phenylsalicylate, waxes and cellulose acetate phthalate.

Exemplary compositions can include fast-dissolving diluents such as mannitol, lactose, sucrose, and/or cyclodextrins. Also included in such formulations can be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., GANTREZ®); and agents to control release such as polyacrylic copolymer (e.g., CARBOPOL 934®). Lubricants, glidants, flavors, coloring agents and stabilizers can also be added for ease of fabrication and use.

In certain of such embodiments, a pharmaceutical composition for oral administration is formulated by combining one or more compounds provided herein with one or more pharmaceutically acceptable carriers. Certain of such carriers enable compounds provided herein to be formulated as tablets, pills, dragees, capsules, liquids, gels, syrups, slurries, suspensions and the like, for oral ingestion by a patient. In certain embodiments, pharmaceutical compositions for oral use are obtained by mixing one or more compounds provided herein and one or more solid excipient. Suitable excipients include, but are not limited to, fillers, such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl cellulose, sodium carboxymethylcellulose, and/or polyvinylpyrrolidone (PVP). In certain embodiments, such a mixture is optionally ground and auxiliaries are optionally added. In certain embodiments, pharmaceutical compositions are formed to obtain tablets or dragee cores. In certain embodiments, disintegrating agents (e.g., cross linked polyvinyl pyrrolidone, agar, or alginic acid or a salt thereof, such as sodium alginate) are added.

In certain embodiments, dragee cores are provided with coatings. In certain of such embodiments, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to tablets or dragee coatings.

In certain embodiments, a daily dosage regimen for a patient contains an oral dose of between 0.1 mg and 2000 mg of a compound provided herein. In certain embodiments, a daily dosage regimen is administered as a single daily dose. In certain embodiments, a daily dosage regimen is administered as two, three, four, or more than four doses.

2. Injectables, Solutions and Emulsions

In certain embodiments, the pharmaceutical composition is prepared for transmucosal administration. In certain of such embodiments penetrants appropriate to the barrier to be permeated are used in the formulation. Such penetrants are generally known in the art.

Parenteral administration, generally characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. Suitable excipients are, for example, water, saline, dextrose, glycerol, mannitol, 1,3-butanediol, Ringer's solution, an isotonic sodium chloride solution or ethanol. In addition, if desired, the pharmaceutical compositions to be administered can also contain minor amounts of non-toxic auxiliary substances such as wetting or emulsifying agents, pH buffering agents, stabilizers, solubility enhancers, and other such agents, such as for example, mono- or diglycerides, fatty acids, such as oleic acid, sodium acetate, sorbitan monolaurate, triethanolamine oleate and cyclodextrins. Implantation of a slow-release or sustained-release system, such that a constant level of dosage is maintained (see, e.g., U.S. Pat. No. 3,710,795) is also contemplated herein. Briefly, a compound provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The compound diffuses through the outer polymeric membrane in a release rate controlling step. The percentage of active compound contained in such parenteral compositions is highly dependent on the specific nature thereof, as well as the activity of the compound and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions can be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcellulose, hydroxypropyl methylcellulose and polyvinylpyrrolidone. Emulsifying agents include Polysorbate 80 (TWEEN® 80). A sequestering or chelating agent of metal ions include EDTA. Pharmaceutical carriers also include ethyl alcohol, polyethylene glycol and propylene glycol for water miscible vehicles and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the patient or animal as is known in the art.

The unit-dose parenteral preparations are packaged in an ampoule, a vial or a syringe with a needle. All preparations for parenteral administration must be sterile, as is known and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Injectables are designed for local and systemic administration. Typically a therapeutically effective dosage is formulated to contain a concentration of at least about 0.1% w/w up to about 90% w/w or more, preferably more than 1% w/w of the active compound to the treated tissue(s). The active ingredient can be administered at once, or can be divided into a number of smaller doses to be administered at intervals of time. It is understood that the precise dosage and duration of treatment is a function of the tissue being treated and can be determined empirically using known testing protocols or by extrapolation from in vivo or in vitro test data. It is to be noted that concentrations and dosage values can also vary with the age of the individual treated. It is to be further understood that for any particular subject, specific dosage regimens should be adjusted over time according to the individual need and the professional judgment of the person administering or supervising the administration of the formulations, and that the concentration ranges set forth herein are exemplary only and are not intended to limit the scope or practice of formulations provided herein.

The compounds can be formulated in any suitable vehicle or form. For example, they can be in micronized or other suitable form and/or can be derivatized to produce a more soluble active product or to produce a prodrug or for other purposes. The form of the resulting mixture depends upon a number of factors, including, for example, an intended mode of administration and the solubility of the compound in the selected carrier or vehicle. The effective concentration is sufficient for ameliorating the symptoms of the condition and can be empirically determined.

In certain embodiments, a pharmaceutical composition is prepared for administration by injection wherein the pharmaceutical composition contains a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampules or in multi dose containers.

Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the compounds to allow for the preparation of highly concentrated solutions.

In certain embodiments, the pharmaceutical composition is prepared for administration by inhalation. Certain of such pharmaceutical compositions for inhalation are prepared in the form of an aerosol spray in a pressurized pack or a nebulizer. Certain of such pharmaceutical compositions contain a propellant, e.g., dichlorodifluoromethane, trichlorofluoromethane, dichlorotetrafluoroethane, carbon dioxide or other suitable gas. In certain embodiments using a pressurized aerosol, the dosage unit may be determined with a valve that delivers a metered amount. In certain embodiments, capsules and cartridges for use in an inhaler or insufflator may be formulated. Certain of such formulations contain a powder mixture of a compound provided herein and a suitable powder base such as lactose or starch.

In certain embodiments, the pharmaceutical compositions provided are administered by continuous intravenous infusion. In certain of such embodiments, from 0.1 mg to 500 mg of the composition is administered per day.

3. Lyophilized Powders

Of interest herein are also lyophilized powders, which can be reconstituted for administration as solutions, emulsions and other mixtures. They can also be reconstituted and formulated as solids or gels.

The sterile, lyophilized powder is prepared by dissolving a compound provided herein, or a pharmaceutically acceptable derivative thereof, in a suitable solvent. The solvent can contain an excipient which improves the stability or other pharmacological component of the powder or reconstituted solution, prepared from the powder. Excipients that can be used include, but are not limited to, dextrose, sorbital, fructose, corn syrup, xylitol, glycerin, glucose, sucrose or other suitable agent. The solvent can also contain a buffer, such as citrate, sodium or potassium phosphate or other such buffer known to those of skill in the art at, typically, about neutral pH. Subsequent sterile filtration of the solution followed by lyophilization under standard conditions known to those of skill in the art provides the desired formulation. Generally, the resulting solution will be apportioned into vials for lyophilization. Each vial will contain a single dosage 10-1000 mg, in one embodiment, 100-500 mg or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, about 1-50 mg, preferably 5-35 mg, more preferably about 9-30 mg of lyophilized powder, is added per mL of sterile water or other suitable carrier. The precise amount depends upon the selected compound. Such amount can be empirically determined.

4. Topical Administration

Topical mixtures are prepared as described for the local and systemic administration. The resulting mixture can be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The compounds or pharmaceutically acceptable derivatives thereof can be formulated as aerosols for topical application, such as by inhalation (see, e.g., U.S. Pat. Nos. 4,044,126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will typically have diameters of less than 50 microns, preferably less than 10 microns.

In certain embodiments, the pharmaceutical compositions for inhalation are prepared in the form of an aerosol spray in a pressurized pack or a nebulizer. Certain of such pharmaceutical compositions contain a propellant, e.g., dichlorodifluoromethane, trichlorofluoromethane, dichlorotetrafluoroethane, carbon dioxide or other suitable gas. In certain embodiments using a pressurized aerosol, the dosage unit can be determined with a valve that delivers a metered amount. In certain embodiments, capsules and cartridges for use in an inhaler or insufflator can be formulated. Certain of such formulations contain a powder mixture of a compound provided herein and a suitable powder base such as lactose or starch.

Exemplary compositions for nasal aerosol or inhalation administration include solutions which can contain, for example, benzyl alcohol or other suitable preservatives, absorption promoters to enhance absorption and/or bioavailability, and/or other solubilizing or dispersing agents such as those known in the art.

The compounds can be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered. These solutions, particularly those intended for ophthalmic use, can be formulated as 0.01%-10% isotonic solutions, pH about 5-7, with appropriate salts. In certain embodiments in which the compositions is administered locally, the dosage regimen is adjusted to achieve a desired local concentration of a compound provided herein.

In certain embodiments, the pharmaceutical composition is prepared for topical administration. Certain of such pharmaceutical compositions contain bland moisturizing bases, such as ointments or creams. Exemplary suitable ointment bases include, but are not limited to, petrolatum, petrolatum plus volatile silicones, lanolin and water in oil emulsions such as Eucerin™, available from Beiersdorf (Cincinnati, Ohio). Exemplary suitable cream bases include, but are not limited to, Nivea™ Cream, available from Beiersdorf (Cincinnati, Ohio), cold cream (USP), Purpose Cream™, available from Johnson & Johnson (New Brunswick, N.J.), hydrophilic ointment (USP) and Lubriderm™, available from Pfizer (Morris Plains, N.J.).

In certain embodiments, the formulation, route of administration and dosage for the pharmaceutical composition provided herein can be chosen in view of a particular patient's condition. (See e.g., Fingl et al. 1975, in "The Pharmacological Basis of Therapeutics", Ch. 1 p. 1). In certain embodiments, the pharmaceutical composition is administered as a single dose. In certain embodiments, a pharmaceutical composition is administered as a series of two or more doses administered over one or more days.

5. Compositions for Other Routes of Administration

Other routes of administration, such as topical application, transdermal patches, and rectal administration are also contemplated herein.

In certain embodiments, the pharmaceutical composition is prepared for topical administration such as rectal administration. The pharmaceutical dosage forms for rectal administration include, but are not limited to rectal suppositories, capsules and tablets for systemic effect. In certain embodiments, a pharmaceutical agent is prepared for rectal administration, such as a suppositories or retention enema. Certain of such pharmaceutical agents contain known ingredients, such as cocoa butter and/or other glycerides. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax (polyoxyethylene glycol) and appropriate mixtures of mono-, di- and triglycerides of fatty acids. Combinations of the various bases can be used. In certain embodiments, the pharmaceutical compositions contain bland moisturizing bases, such as ointments or creams. Exemplary suitable ointment bases include, but are not limited to, petrolatum, petrolatum plus volatile silicones, lanolin and water in oil emulsions such as Eucerin™, available from Beiersdorf (Cincinnati, Ohio). Exemplary suitable cream bases include, but are not limited to, Nivea™ Cream, available from Beiersdorf (Cincinnati, Ohio), cold cream (USP), Purpose Cream™, available from Johnson & Johnson (New Brunswick, N.J.), hydrophilic ointment (USP) and Lubriderm™, available from Pfizer (Morris Plains, N.J.). Agents to raise the melting point of suppositories include spermaceti and wax. Rectal suppositories can be prepared either by the compressed method or by molding. The typical weight of a rectal suppository is about 2 to 3 gm.

Tablets and capsules for rectal administration are manufactured using the same pharmaceutically acceptable substance and by the same methods as for formulations for oral administration.

6. Articles of Manufacture

The compounds or pharmaceutically acceptable derivatives can be packaged as articles of manufacture containing packaging material, within the packaging material a compound or pharmaceutically acceptable derivative thereof provided herein, which is effective for modulating the activity of androgen receptor, or for treatment, prevention or amelioration of one or more symptoms of androgen receptor mediated diseases or disorders, or diseases or disorders in which androgen receptor activity is implicated, and a label that indicates that the compound or composition, or pharmaceutically acceptable derivative thereof, is used for modulating the activity of androgen receptor or for treatment, prevention or amelioration of one or more symptoms of androgen receptor mediated diseases or disorders, or diseases or disorders in which androgen receptor activity is implicated.

The articles of manufacture provided herein contain packaging materials. Packaging materials for use in packaging pharmaceutical products are well known to those of skill in the art. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated as are a variety of treatments for any disease or disorder in which androgen receptor activity is implicated as a mediator or contributor to the symptoms or cause.

In certain embodiments, the pharmaceutical compositions can be presented in a pack or dispenser device which can contain one or more unit dosage forms containing a compound provided herein. The pack can for example contain metal or plastic foil, such as a blister pack. The pack or dispenser device can be accompanied by instructions for administration. The pack or dispenser can also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, can be the labeling approved by the U.S. Food and Drug Administration for prescription drugs, or the approved product insert. Compositions containing a compound provided herein formulated in a compatible pharmaceutical carrier can also be prepared, placed in an appropriate container, and labeled for treatment of an indicated condition.

E. Evaluation of the Activity of the Compounds

Standard physiological, pharmacological and biochemical procedures are available for testing the compounds provided herein to identify those that possess activity as androgen receptor modulators. In vitro and in vivo assays known in the art can be used to evaluate the activity of the compounds provided herein as androgen receptor modulators. Exemplary assays include, but are not limited to fluorescence polarization assay, luciferase assay, and co-transfection assay. In certain embodiments, the compounds provided herein are capable of modulating activity of androgen receptor in a "co-transfection" assay (also called a "cis-trans" assay), which is known in the art. See e.g., Evans et al., *Science*, 240:889-95 (1988); U.S. Pat. Nos. 4,981,784 and 5,071,773; Pathirana et al., "Nonsteroidal Human Progesterone Receptor Modulators from the Marie Alga Cymopolia Barbata," *Mol. Pharm.* 47:630-35 (1995)). Modulating activity in a co-transfection assay has been shown to correlate with in vivo modulating activity. Thus, in certain embodiments, such assays are predictive of in vivo activity. See, e.g, Berger et al., *J. Steroid Biochem. Molec. Biol.* 41:773 (1992).

In certain co-transfection assays, two different co-transfection plasmids are prepared. In the first co-transfection plasmid, cloned cDNA encoding an intracellular receptor (e.g., androgen receptor) is operatively linked to a constitutive promoter (e.g., the SV 40 promoter). In the second co-transfection plasmid, cDNA encoding a reporter protein, such as firefly luciferase (LUC), is operatively linked to a promoter that is activated by a receptor-dependant activation factor. Both co-transfection plasmids are co-transfected into the same cells. Expression of the first co-transfection plasmid results in production of the intracellular receptor protein. Activation of that intracellular receptor protein (e.g., by binding of an agonist) results in production of a receptor-dependant activation factor for the promoter of the second co-transfection plasmid. That receptor-dependant activation factor in turn results in expression of the reporter protein encoded on the second co-transfection plasmid. Thus, reporter protein expression is linked to activation of the receptor. Typically, that reporter activity can be conveniently measured (e.g., as increased luciferase production).

Certain co-transfection assays can be used to identify agonists, partial agonists, and/or antagonists of intracellular receptors. In certain embodiments, to identify agonists, co-transfected cells are exposed to a test compound. If the test compound is an agonist or partial agonist, reporter activity is expected to increase compared to co-transfected cells in the absence of the test compound. In certain embodiments, to identify antagonists, the cells are exposed to a known agonist (e.g., androgen for the androgen receptor) in the presence and absence of a test compound. If the test compound is an antagonist, reporter activity is expected to decrease relative to that of cells exposed only to the known agonist.

In certain embodiments, compounds provided herein are used to detect the presence, quantity and/or state of receptors in a sample. In certain of such embodiments, samples are obtained from a patient. In certain embodiments, compounds are radio- or isotopically-labeled. For example, compounds provided herein that selectively bind androgen receptors may be used to determine the presence of such receptors in a sample, such as cell homogenates and lysates.

F. Methods of Use of the Compounds and Compositions

Methods of use of the compounds and compositions provided herein also are provided. The methods include in vitro and in vivo uses of the compounds and compositions for altering androgen receptor activity and for treatment, prevention, or amelioration of one or more symptoms of diseases or disorder that are modulated by androgen receptor activity, or in which androgen receptor activity, is implicated. In certain embodiments, provided herein are methods of treating a patient by administering a compound provided herein. In certain embodiments, such patient exhibits symptoms or signs of a androgen receptor mediated condition. In certain embodiments, a patient is treated prophylactically to reduce or prevent the occurrence of a condition.

The compounds provided herein can be used in the treatment of a variety of conditions including, but not limited to, maintenance of muscle strength and function (e.g., in the elderly); reversal or prevention of frailty or age-related functional decline ("ARFD") in the elderly (e.g., sarcopenia); treatment of catabolic side effects of glucocorticoids; prevention and/or treatment of reduced bone mass, density or growth (e.g., osteoporosis and osteopenia); treatment of chronic fatigue syndrome (CFS); chronic myalgia; treatment of acute fatigue syndrome and muscle loss following elective surgery (e.g., post-surgical rehabilitation); accelerating of wound healing; accelerating bone fracture repair (such as accelerating the recovery of hip fracture patients); accelerating healing of complicated fractures, e.g. distraction osteogenesis; in joint replacement; prevention of post-surgical adhesion formation; acceleration of tooth repair or growth; maintenance of sensory function (e.g., hearing, sight, olefaction and taste); treatment of periodontal disease; treatment of wasting secondary to fractures and wasting in connection with chronic obstructive pulmonary disease (COPD), chronic liver disease, AIDS, weightlessness, cancer cachexia, burn and trauma recovery, chronic catabolic state (e.g., coma), eating disorders (e.g., anorexia) and chemotherapy; treatment of cardiomyopathy; treatment of thrombocytopenia; treatment of growth retardation in connection with Crohn's disease; treatment of short bowel syndrome; treatment of irritable bowel syndrome; treatment of inflammatory bowel disease; treatment of Crohn's disease and ulcerative colitis; treatment of complications associated with transplantation; treatment of physiological short stature including growth hormone deficient children and short stature associated with chronic illness; treatment of obesity and growth retardation associated with obesity; treatment of anorexia (e.g., associated with cachexia or aging); treatment of hypercortisolism and Cushing's syndrome; Paget's disease; treatment of osteoarthritis; induction of pulsatile growth hormone release; treatment of osteochondrodysplasias; treatment of depression, nervousness, irritability and stress; treatment of reduced mental energy and low self-esteem (e.g, motivation/assertiveness); improvement of cognitive function (e.g., the treatment of dementia, including Alzheimer's disease and short term memory loss); treatment of catabolism in connection with pulmonary dysfunction and ventilator dependency; treatment of cardiac dysfunction (e.g., associated with valvular disease, myocardial infarction, cardiac hypertrophy or congestive heart failure); lowering blood pressure; protection against ventricular dysfunction or prevention of reperfusion events; treatment of adults in chronic dialysis; reversal or slowing of the catabolic state of aging; attenuation or reversal of protein catabolic responses following trauma (e.g., reversal of the catabolic state associated with surgery, congestive heart failure, cardiac myopathy, burns, cancer, COPD etc.); reducing cachexia and protein loss due to chronic illness such as cancer or AIDS; treatment of hyperinsulinemia including nesidioblastosis; treatment of immunosuppressed patients; treatment of wasting in connection with multiple sclerosis or other neurodegenerative disorders; promotion of myelin repair; maintenance of skin thickness; treatment of metabolic homeostasis and renal homeostasis (e.g., in the frail elderly); stimulation of osteoblasts, bone remodeling and cartilage growth; regulation of food intake; treatment of insulin resistance, including NIDDM, in mammals (e.g., humans); treatment of insulin resistance in the heart; improvement of sleep quality and correction of the relative hyposomatotropism of senescence due to high increase in REM sleep and a decrease in REM latency; treatment of hypothermia; treatment of congestive heart failure; treatment of lipodystrophy (e.g., in patients taking HIV or AIDS therapies such as protease inhibitors); treatment of muscular atrophy (e.g., due to physical inactivity, bed rest or reduced weight-bearing conditions); treatment of musculoskeletal impairment (e.g., in the elderly); improvement of the overall pulmonary function; treatment of sleep disorders; and the treatment of the catabolic state of prolonged critical illness; treatment of hirsutism, acne, seborrhea, androgenic alopecia, anemia, hyperpilosity, benign prostate hypertrophy, adenomas and neoplasies of the prostate (e.g., advanced metastatic prostate cancer) and malignant tumor cells containing the androgen receptor, such as is the case for breast, brain, skin, ovarian, bladder, lymphatic, liver and kidney cancers; cancers of the skin, pancreas, endometrium, lung and colon; osteosarcoma; hypercalcemia of malignancy; metastatic bone disease; treatment of spermatogenesis, endometriosis and polycystic ovary syndrome; counteracting preeclampsia, eclampsia of pregnancy and preterm labor; treatment of premenstrual syndrome; treatment of vaginal dryness; age related decreased testosterone levels in men, male menopause, hypogonadism, male hormone replacement, male and female sexual dysfunction (e.g., erectile dysfunction, decreased sex drive, sexual well-being, decreased libido), male and female contraception, hair loss, Reaven's Syndrome and the enhancement of bone and muscle performance/strength. The term treatment is also intended to include prophylactic treatment.

In certain embodiments, the compounds provided herein are used to treat acne, male-pattern baldness, wasting diseases, hirsutism, hypogonadism, osteoporoses, infertility, impotence, obesity, and cancer. In certain embodiments, one or more compounds provided herein are used to stimulate hematopoiesis. In certain embodiments, one or more compounds provided herein are used for contraception.

In certain embodiments, one or more compounds provided herein are used to treat cancer. Certain exemplary cancers include, but are not limited to, breast cancer, colorectal cancer, gastric carcinoma, glioma, head and neck squamous cell carcinoma, papillary renal carcinoma, leukemia, lymphoma, Li-Fraumeni syndrome, malignant pleural mesothelioma, melanoma, multiple myeloma, non-small cell lung cancer, synovial sarcoma, thyroid carcinoma, transitional cell carcinoma of urinary bladder, and prostate cancer, including, but not limited to prostatic hyperplasia.

In certain embodiments, one or more compounds provided herein are used to improve athletic performance. In certain such embodiments, one or more compounds provided herein are used, for example to shorten the time normally needed to recover from physical exertion or to increase muscle strength. Athletes to whom one or more compounds provided herein can be administered include, but are not limited to, horses, dogs, and humans. In certain embodiments, one or more compounds provided herein are administered to an athlete engaged in a professional or recreational competition, including, but not limited to weight-lifting, body-building, track and field events, and any of various team sports. In certain embodiments, provided are methods for treating a patient by administering one or more selective androgen receptor agonists and/or partial agonists. Exemplary conditions that can be treated with such selective androgen receptor agonists and/or partial agonist include, but are not limited to, hypogonadism, wasting diseases, cancer cachexia, frailty, infertility, and osteoporosis. In certain embodiments, a selective androgen receptor agonist or partial agonist is used for male hormone replacement therapy. In certain embodiments, one or more selective androgen receptor agonists and/or partial agonists are used to stimulate hematopoiesis. In certain embodiments, a selective androgen receptor agonist or partial agonist is used as an anabolic agent. In certain embodiments, a selective androgen receptor agonist and/or partial agonist is used to improve athletic performance.

In certain embodiments, provided herein are methods for treating a patient by administering one or more selective androgen receptor antagonists and/or partial agonists. Exemplary conditions that may be treated with such one or more selective androgen receptor antagonists and/or partial agonists include, but are not limited to, hirsutism, acne, male-pattern baldness, prostatic hyperplasia, and cancer, including, but not limited to, various hormone-dependent cancers, including, without limitation, prostate and breast cancer.

G. Combination Therapies

In certain embodiments, one or more compounds or compositions provided herein can be co-administered with one or more other pharmaceutical agents. In certain embodiments, such one or more other pharmaceutical agents are designed to treat the same disease or condition as the one or more compounds or pharmaceutical compositions provided herein. In certain embodiments, such one or more other pharmaceutical agents are designed to treat a different disease or condition as the one or more compounds or compositions provided herein. In certain embodiments, such one or more other pharmaceutical agents are designed to treat an undesired effect of one or more compounds or compositions provided herein. In certain embodiments, one or more compounds or compositions provided herein is co-administered with another pharmaceutical agent to treat an undesired effect of that other pharmaceutical agent.

In certain embodiments, compounds or compositions provided herein and one or more other pharmaceutical agents are administered at the same time. In certain embodiments, compounds or compositions provided herein and one or more other pharmaceutical agents are administered at the different times. In certain embodiments, compounds or compositions provided herein and one or more other pharmaceutical agents are prepared together in a single formulation. In certain embodiments, compounds or compositions provided herein and one or more other pharmaceutical agents are prepared separately.

Examples of pharmaceutical agents that may be co-administered with compounds or compositions provided herein include, but are not limited to, analgesics (e.g., acetaminophen); anti-inflammatory agents, including, but not limited to non-steroidal anti-inflammatory drugs (e.g., ibuprofen, COX-1 inhibitors, and COX-2, inhibitors); salicylates; antibiotics; antivirals; antifungal agents; antidiabetic agents (e.g., biguanides, glucosidase inhibitors, insulins, sulfonylureas, and thiazolidenediones); adrenergic modifiers; diuretics; hormones (e.g., anabolic steroids, androgen, estrogen, calcitonin, progestin, somatostan, and thyroid hormones); immunomodulators; muscle relaxants; antihistamines; osteoporosis agents (e.g., biphosphonates, calcitonin, and estrogens); prostaglandins, antineoplastic agents; psychotherapeutic agents; sedatives; poison oak or poison sumac products; antibodies; and vaccines.

In other embodiments, pharmaceutical agents that may be co-administered with compounds or compositions provided herein include, but are not limited to, other modulators of nuclear hormone receptors or other suitable therapeutic agents useful in the treatment of the aforementioned disorders including: anti-diabetic agents; anti-osteoporosis agents; anti-obesity agents; anti-inflammatory agents; anti-anxiety agents; anti-depressants; anti-hypertensive agents; anti-platelet agents; anti-thrombotic and thrombolytic agents; cardiac glycosides; cholesterol/lipid lowering agents; mineralocorticoid receptor antagonists; phosphodiesterase inhibitors; protein tyrosine kinase inhibitors; thyroid mimetics (including thyroid receptor agonists); anabolic agents; HIV or AIDS therapies; therapies used in the treatment of Alzheimer's and other cognitive disorders; therapies used in the treatment of sleeping disorders; anti-proliferative agents; and anti-tumor agents.

EXAMPLES

The following examples, including experiments and results achieved, are provided for illustrative purposes only and are not to be construed as limiting the claimed subject matter.

Example 1

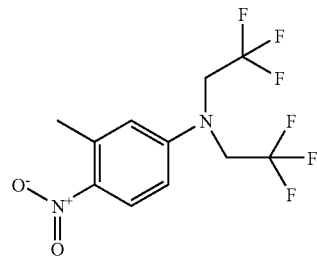 [SMILES: Cc1cc(N(CC(F)(F)F)CC(F)(F)F)ccc1[N+](=O)[O-]]

N,N-bis(2,2,2-trifluoroethyl)-3-methyl-4-nitroaniline (Compound 101, Structure 2 of Scheme I, where $R^1=NO_2$, $R^2=CH_3$, $R^3=R^4=R^5=R^6=R^7=R^{10}=R^{11}=H$, $R^8=R^9=CF_3$)

3-Methyl-4-nitroaniline 3.9 g (25 mmol) was dissolved in 100 mL of trifluoroacetic acid with stirring under $N_2$ at 60° C. Next, sodium borohydride pellets (14 g, 15 eq.) were added portionwise. Ten minutes after the addition of the pellets, the reaction was heated to 90° C. After 12 h at 90° C., the reaction was cooled, added slowly to water, and then filtered. The resulting solid filtrate was washed first with water and then with hexanes and was then dried. This procedure resulted in 6.6 g (82% yield) of a light yellow powder. Data for compound 101: $^1$H-NMR (CDCl$_3$, 500 MHz) 8.10 (d, 1H, J=9.3 Hz), 6.78 (dd, 1H, J=9.3 and 2.9 Hz), 6.72 (d, 1H, J=2.9 Hz), 4.13 (q, 4H, J=8.4 Hz), 2.66 (s, 3H).

Example 2

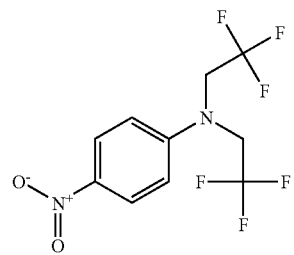 [SMILES: O=[N+]([O-])c1ccc(N(CC(F)(F)F)CC(F)(F)F)cc1]

N,N-bis(2,2,2-trifluoroethyl)-4-nitroaniline (Compound 102, Structure 2 of Scheme I, where $R^1=NO_2$, $R^2=R^3=R^4=R^5=R^6=R^7=R^{10}=R^{11}=H$, $R^8=R^9=CF_3$)

This compound was prepared using the method described in Example 1, except that 4-nitroaniline was used in place of 3-methyl-4-nitroaniline. Compound 102 was isolated as a solid: $^1$H NMR (CDCl$_3$, 400 MHz) 8.19 (d, 2H, J=9.5 Hz), 86.93 (d, 2H, J=9.5 Hz), 4.16 (q, 2H, J=8.3 Hz).

Example 3A

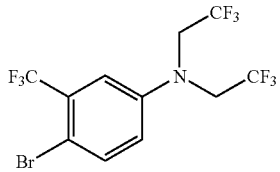

4-Bromo-N,N-bis(2,2,2-trifluoroethyl)-3-(trifluoromethyl)aniline (Compound 103A, Structure 2 of Scheme I, where $R^1$=bromo, $R^2$=trifluoromethyl; $R^3$=$R^4$=$R^5$=$R^6$=$R^7$=$R^{10}$=$R^{11}$=H, $R^8$=$R^9$=CF$_3$)

This compound was prepared using the method described in Example 1, except that 4-bromo-3-(trifluoromethyl)aniline was used in place of 3-methyl-4-nitroaniline. Compound 103A was isolated as a solid: $^1$H NMR (CDCl$_3$, 400 MHz) 7.58 (d, 1H, J=8.8 Hz), 7.19 (d, 1H, J=3.2 Hz), 6.91 (dd, 1H, J=8.8 and 3.2 Hz), 4.06 (q, 4H, J=8.5 Hz).

Example 3

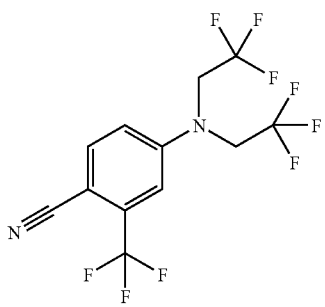 [SMILES: N#Cc1ccc(N(CC(F)(F)F)CC(F)(F)F)cc1C(F)(F)F]

4-(Bis(2,2,2-trifluoroethyl)amino)-2-(trifluoromethyl)benzonitrile (Compound 103, Structure 2 of Scheme I, where $R^1$=cyano, $R^2$=trifluoromethyl; $R^3$=$R^4$=$R^5$=$R^6$=$R^7$=$R^{10}$=$R^{11}$=H, $R^8$=$R^9$=CF$_3$)

To prepare this compound, Zn(CN)$_2$ (26 mg, 0.22 mmol), Pd(PPh$_3$)$_4$, and Compound 103A (77 mg, 0.19 mmol) were combined in a dry Schlenk flask. The mixture was then added to 2 mL of a 1% DMF/water solution, which had been degassed by bubbling N$_2$ for 20 minutes. That mixture was then heated to 130° C. for 20 h, and then partitioned with EtOAc and saturated aqueous NH$_4$Cl. The organic layer washed sequentially with water and then with brine, dried over MgSO$_4$, filtered, and concentrated. Flash chromatography (silica gel, 4:1 hexanes:EtOAc) afforded Compound 103. Compound 103 was isolated as a solid: $^1$H NMR (CDCl$_3$, 400 MHz) 7.73 (d, 1H, J=8.8 Hz), 7.19 (d, 1H, J=2.8 Hz), 7.08 (dd, 1H, J=8.8 and 2.8 Hz), 4.16 (q, 4H, J=8.2 Hz).

Example 4

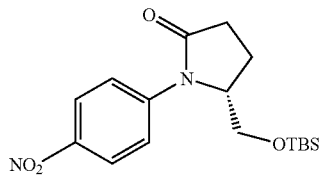 [SMILES: CC(C)(C)[Si](C)(C)OC[C@H]1CCC(=O)N1c1ccc([N+](=O)[O-])cc1]

(5R)—N-(4-nitrophenyl)-5-(dimethyl-tert-butylsilyloxymethyl)-2-pyrrolidone (Compound 104, Structure 5 of Scheme II, where $R^1$=nitro, $R^{10}$=dimethyl-tert-butylsilyloxymethyl, $R^2$=$R^3$=$R^4$=$R^5$=$R^9$=$R^{12}$=$R^{13}$=H, $R^{6a}$ and $R^{7a}$ form a carbonyl, n=0, Z=CH$_2$)

General Procedure 1 (Palladium mediated coupling of aryl bromide and amine or amide): A solution of an aryl bromide (such as 4-bromo-nitrobenzene in toluene (0.05-0.2 M), Cs$_2$CO$_3$ (2-3 equiv), Pd$_2$(dba)$_3$ (1-3 mol %), and (R)-BINAP (2.0 mg, 0.003 mmol, 1.5-4.5 mol %) are combined in a schlenk tube. The amine or amide (3-5 equiv.) is then added to the reaction flask. The resulting reaction mixture is heated to 100° C. for 4-48 hours, cooled to room temperature, diluted with Et$_2$O, filtered, and concentrated in vacuo. Chromatography (silica gel, CH$_2$Cl$_2$:hexanes or EtOAc:hexanes) of the crude mixture afforded compounds of Structure 5.

Compound 104 was prepared according the General Procedure 1 using 4-bromonitrobenzene as the aryl bromide. Compound 104 was isolated as a yellow oil. $^1$H NMR (CDCl$_3$, 400 MHz) 8.1 (s, 1H), 8.0 (m, 2H), 4.5 (m, 1H), 3.76 (dd, 1H, J=3.9 and 10.7 Hz), 3.70 (dd, 1H, J=3.4 and 10.7 Hz), 2.8 (m, 1H), 2.6 (m, 1H), 2.4 (m, 1H), 2.2 (m, 1H), 0.8 (s, 9H), 0.1 (s, 3H), 0.0 (s, 3H).

Example 5

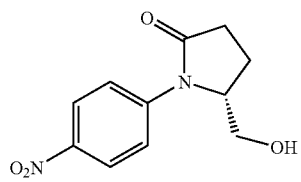 [SMILES: O=C1CC[C@H](CO)N1c1ccc([N+](=O)[O-])cc1]

(5R)—N-(4-nitrophenyl)-5-(hydroxymethyl)-2-pyrrolidone (Compound 105, Structure 5 of Scheme II, where $R^1$=nitro, $R^{10}$=hydroxymethyl, $R^2$=$R^3$=$R^4$=$R^5$=$R^9$=$R^{12}$=$R^{13}$=H, $R^{6a}$ and $R^{7a}$ form a carbonyl, n=0, Z=CH$_2$)

Compound 105 was prepared by hydrolyzing the silyl group of Compound 104. Compound 105 was isolated as an oil: $^1$H NMR (CDCl$_3$, 400 MHz) 8.25 (d, 2H, J=9.3 Hz), 7.77 (d, 2H, J=9.3 Hz), 4.48 (ddt, 1H, J=8.6, 4.6 and 3.0 Hz), 3.82 (dt, 1H, J=11.4 and 4.6 Hz), 3.74 (ddd, 1H, J=11.4, 5.5 and 3.0 Hz), 2.81 (ddd, 1H, J=17.5, 10.0 and 8.6 Hz), 2.58 (ddd, 1H, J=17.5, 10.1 and 4.3 Hz), 2.36 (ddt, 1H, J=13.0, 10.1 and 8.6 Hz), 2.22 (dddd, 1H, J=13.0, 10.0, 4.3 and 3.0 Hz), 1.61 (dd, 1H, J=5.5 and 4.6 Hz).

Example 6

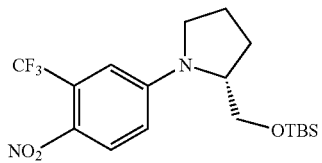 [SMILES: CC(C)(C)[Si](C)(C)OC[C@H]1CCCN1c1ccc([N+](=O)[O-])c(C(F)(F)F)c1]

(2R)—N-(4-nitro-3-trifluoromethylphenyl)-2-(dimethyl-tert-butylsilyloxymethyl)pyrrolidine (Compound 106, Structure 5 of Scheme II, where $R^1$=nitro, $R^2$=trifluoromethyl, $R^{10}$=dimethyl-tert-butylsilyloxymethyl, $R^3$=$R^4$=$R^5$=$R^{6a}$=$R^{7a}$=$R^9$=$R^{12}$=$R^{13}$=H, n=0, Z=$CH_2$)

To prepare this compound, first (5R)—N-(4-nitro-3-trifluoromethylphenyl)-2-(dimethyl-tert-butylsilyloxymethyl)-2-pyrrolidone (Compound 107, Structure 5 of Scheme II, where $R^1$=nitro, $R^2$=trifluoromethyl, $R^{10}$=dimethyl-tert-butylsilyloxymethyl, $R^3$=$R^4$=$R^5$=$R^9$=$R^{12}$=$R^{13}$=H, $R^{6a}$ and $R^{7a}$ form a carbonyl, n=0, Z=$CH_2$) was prepared using the method described in Example 4, except that 3-trifluoromethyl-4-nitrobromobenzene was used in place of 4-nitrobromobenzene. Compound 107 (1.94 g, 4.6 mmol) was then dissolved in 3 mL of dry THF with stirring and then cooled in an ice water bath. An alane/N,N-dimethylethylamine complex (36 mL, 18 mmol) was added and the mixture was allowed to warm to room temperature. After 1 hour, 50 mL of methanol and 4 mL of glacial acetic acid were added, followed by the addition of sodium cyanoborohydride (2.89 g, 46 mmol). After 10 minutes, the reaction mixture was concentrated under reduced pressure. Water was added and the solution was extracted with EtOAc. The extracted organic layer washed with saturated $NaHCO_3$ and brine (2 times), dried ($MgSO_4$) and concentrated under reduced pressure. Chromatography (silica, 50% EtOAc:Hex) afforded 624 mg (41% yield) of a yellow oil. Data for Compound 106: $^1$H NMR ($CDCl_3$, 400 MHz) 8.10 (d, 1H, J=9.27), 6.99 (d, 1H, J=2.44 Hz), 6.72 (dd, 1H, J=2.93 and 9.27 Hz), 4.05 (m, 1H), 3.70 (dd, 1H, J=4.88 and 10.25 Hz), 3.63 (dd, 1H, J=6.34 and 10.25 Hz), 3.55 (m, 1H (, 3.35 (m, 1H), 2.0-2.2 (m, 4H), 0.9 (s, 9H), 0.05 (s, 3H), 0.04 (s, 3H). LCMS 404 ($M^+$), 259 ($M^+$-$CH_2OTBS$, 100%).

Example 7

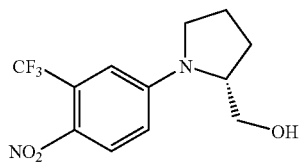 [SMILES: O=[N+]([O-])c1ccc(N2CCC[C@@H]2CO)cc1C(F)(F)F]

(2R)—N-(4-nitro-3-trifluoromethylphenyl)-2-(hydroxymethyl)pyrrolidine (Compound 108, Structure 5 of Scheme II, where $R^1$=nitro, $R^2$=trifluoromethyl, $R^{10}$=hydroxymethyl, $R^3$=$R^4$=$R^5$=$R^{6a}$=$R^{7a}$=$R^9$=$R^{12}$=$R^{13}$=H, n=0, Z=$CH_2$)

Compound 106 from Example 6 (620 mg, 1.53 mmol) was dissolved in 4 mL of ethanol with stirring and 1 mL of concentrated HCl was added at room temperature. After the reaction was judged complete by TLC (40% EtOAc/hexanes) the pH was adjusted to approximately pH 8 using 1N NaOH. The mixture was extracted with EtOAc and the organic layer washed with brine, dried ($MgSO_4$) and concentrated under reduced pressure. The resulting oil was triturated with hexanes, decanted and dried to afford a yellow oil (354 mg, 79% yield-). Data for Compound 108: $^1$H NMR ($CDCl_3$, 400 MHz) 8.08 (d, 1H, J=9.27 Hz), 7.0 (d, 1H, J=2.44 Hz), 6.77 (dd, 1H, J=2.44 and 9.27 Hz), 4.09 (m, 1H), 3.77 (m, 1H), 3.71 (m, 1H), 3.62 (m, 1H), 3.36 (m, 1H), 2.1-2.2 (m, 4H), and 1.63 (m, 1H).

Example 8

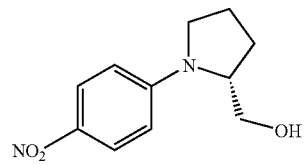 [SMILES: O=[N+]([O-])c1ccc(N2CCC[C@@H]2CO)cc1]

(2R)—N-(4-nitrophenyl)-2-(hydroxymethyl)pyrrolidine (Compound 109, Structure 5 of Scheme II, where $R^1$=nitro, $R^{10}$=hydroxymethyl, $R^2$=$R^3$=$R^4$=$R^5$=$R^{6a}$=$R^{7a}$=$R^9$=$R^{12}$=$R^{13}$=H, n=0, Z=$CH_2$)

This compound was prepared by reduction of the carbonyl group of Compound 105 using the same reaction described in Example 6. Data for Compound 109: $^1$H NMR ($CDCl_3$, 400 MHz) 8.16 (m, 2H), 6.65 (m, 2H), 4.06 (m, 1H), 3.78 (m, 1H), 3.68 (m, 1H), 3.59 (m, 1H), 3.35 (m, 1H), 2.1-2.2 (m, 4H), 1.6 (m, 1H).

Example 9

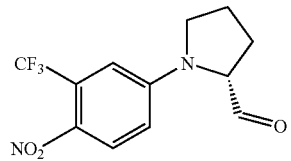 [SMILES: O=C[C@H]1CCCN1c1ccc([N+](=O)[O-])c(C(F)(F)F)c1]

(2R)—N-(3-Trifluoromethyl-4-nitrophenyl)-2-formylpyrrolidine (Compound 110, Structure 5 of Scheme II, where $R^1$=nitro, $R^2$=trifluoromethyl, $R^{10}$=formyl, $R^3$=$R^4$=$R^5$=$R^{6a}$=$R^{7a}$=$R^9$=$R^{12}$=$R^{13}$=H, n=0, Z=$CH_2$)

This compound was prepared by oxidation of Compound 108 from Example 7. Data for Compound 110: $^1$H NMR ($CDCl_3$, 400 MHz) 9.63 (d, 1H, J=2.44 Hz), 8.08 (d, 1H, J=9.27 Hz), 6.89 (d, 1H, J=2.44 Hz), 6.65 (dd, 1H, J=2.44 and 9.27 Hz), 4.38 (m, 1H), 3.75 (m, 1H), 3.56 (m, 1H), 2.37 (m, 2H), 2.23 (m, 1H), 2.1 (m, 1H).

Example 10

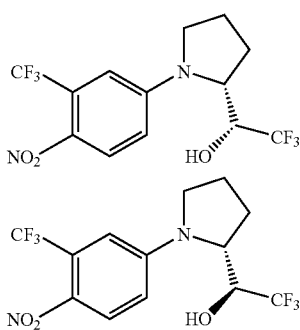

(2R)—N-(3-Trifluoromethyl-4-nitrophenyl)-2-(1-(S)-hydroxy-2,2,2-trifluoroethyl)pyrrolidine (Compound 111, Structure 5 of Scheme II, where $R^1$=nitro, $R^2$=trifluoromethyl, $R^{10}$=1-(S)-hydroxy-2,2,2-trifluoroethyl, $R^3$=$R^4$=$R^5$=$R^{6a}$=$R^{7a}$=$R^9$=$R^{12}$=$R^{13}$=H, n=0, Z=$CH_2$) and (2R)—N-(3-Trifluoromethyl-4-nitrophenyl)-2-(1-(R)-hydroxy-2,2,2-trifluoroethyl)pyrrolidine (Compound 112, Structure 5 of Scheme II, where $R^1$=nitro, $R^2$=trifluoromethyl, $R^{10}$=1-(R)-hydroxy-2,2,2-trifluoroethyl, $R^3$=$R^4$=$R^5$=$R^{6a}$=$R^{7a}$=$R^9$=$R^{12}$=$R^{13}$=H, n=0, Z=$CH_2$)

To prepare these compounds, compound 110 from Example 9 (290 mg, 1.01 mmol) was dissolved in 8 mL of dry THF and cooled in an dry ice/isopropanol/acetone bath with stirring. Cesium fluoride (760 mg, 5 mmol) and TMSCF$_3$ (163 μL, 1.1 mmol) were added and the reaction was allowed to warm to room temperature. After 12 hours, water was added and the mixture was extracted into EtOAc, dried (MgSO$_4$) and concentrated under reduced pressure. Chromatography (silica gel, 35-40% gradient EtOAc:hexanes) afforded the separated diastereomers. Data for Compound 111: $^1$H NMR (CDCl$_3$, 400 MHz) 8.10 (d, 1H, J=9.27 Hz), 6.95 (d, 1H, J=2.92 Hz), 6.69 (dd, 1H, J=2.92 and 9.27 Hz), 4.39 (m, 1H), 4.28 (m, 1H), 3.69 (m, 1H), 3.43 (m, 1H), 2.54 (m, 1H), 2.4 (m, 2H), 2.12 (m, 2H). Data for Compound 112: $^1$H NMR (CDCl$_3$, 400 MHz) isomer 2: 8.06 (d, 1H, J=9.27 Hz), 7.15 (d, 1H, =2.92 Hz), 6.93 (dd, 1H, J=2.92 and 9.27 Hz), 4.32 (m, 1H), 3.98 (m, 1H), 3.60 (m, 1H), 3.37 (m, 1H), 2.50 (d, 1H, J=3.9 Hz), 2.1-2.3 (m, 4H).

Example 11

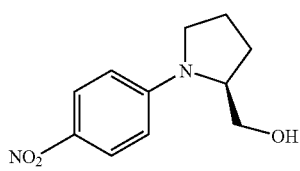 [SMILES: O=[N+]([O-])c1ccc(N2CCC[C@H]2CO)cc1]

(2S)—N-(4-nitrophenyl)-2-(hydroxymethyl)pyrrolidine (Compound 113, Structure 5 of Scheme II, where $R^1$=nitro, $R^{10}$=hydroxymethyl, $R^2$=$R^3$=$R^4$=$R^5$=$R^{6a}$=$R^{7a}$=$R^9$=$R^{12}$=$R^{13}$=H, n=0, Z=$CH_2$)

This compound was prepared using the method described in Example 8, except that the S-isomer of Compound 105 was used as the starting material. Data for Compound 113: $^1$H NMR (CDCl$_3$, 500 MHz) 8.08 (d, 2H, J=9.5 Hz), 6.60 (d, 2H, J=9.5 Hz), 4.02 (m, 1H), 3.73 (ddd, 1H, J=11.0, 5.7 and 4.2 Hz), 3.64 (ddd, 1H, J=11.0, 7.0 and 5.7 Hz), 3.55 (m, 1H), 3.30 (dt, 1H, J=10.3 and 7.8 Hz), 2.11 (m, 4H), 1.73 (t, 1H, J=5.7 Hz).

Example 12

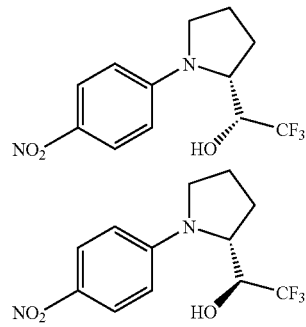

(2R)—N-(4-nitrophenyl)-2-(1-(S)-hydroxy-2,2,2-trifluoroethyl)pyrrolidine (Compound 114, Structure 5 of Scheme II, where $R^1$=nitro, $R^{10}$=1-(S)-hydroxy-2,2,2-trifluoroethyl, $R^2$=$R^3$=$R^4$=$R^5$=$R^{6a}$=$R^{7a}$=$R^9$=$R^{12}$=$R^{13}$=H, n=0, Z=$CH_2$) and (2R)—N-(4-nitrophenyl)-2-(R)-(1-(R)-hydroxy-2,2,2-trifluoroethyl)pyrrolidine (Compound 115, Structure 5 of Scheme II, where $R^1$=nitro, $R^{10}$=1-(R)-hydroxy-2,2,2-trifluoroethyl, $R^2$=$R^3$=$R^4$=$R^5$=$R^{6a}$=$R^{7a}$=$R^9$=$R^{12}$=$R^{13}$=H, n=0, Z=$CH_2$)

To prepare these compounds, first Compound 109 was oxidized using the method described in Example 9. The resulting aldehyde was then used in place of Compound 110 in the method described in Example 10. Data for Compound 114: $^1$H NMR (CDCl$_3$, 400 MHz) 8.14 (m, 2H), 6.57 (m, 2H), 4.45 (m, 1H), 4.26 (m, 1H), 3.68 (m, 1H), 3.41 (m, 1H), 2.53 (d, 1H, J=5.37 Hz), 2.45 (m, 1H), 2.38 (m, 1H), 2.0-2.2 (m, 2H). Data for Compound 115: $^1$H NMR (CDCl$_3$, 400 MHz) 8.16 (m, 2H), 6.85 (m, 2H), 4.35 (m, 1H), 3.95 (m, 1H), 3.68 (m, 1H), 3.36 (m, 1H), 2.56 (br s, 1H), 2.24 (m, 1H), 2.1-2.2 (m, 3H).

Example 13

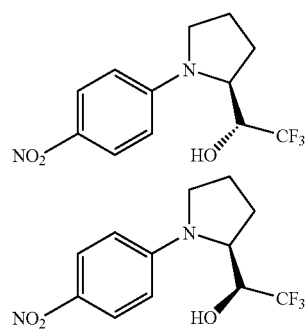

(2S)—N-(4-nitrophenyl)-2-(1-(s)-hydroxy-2,2,2-trifluoroethyl)pyrrolidine (Compound 116, Structure 5 of Scheme II, where $R^1$=nitro, $R^{10}$=1-(S)-hydroxy-2,2,2-trifluoroethyl, $R^2$=$R^3$=$R^4$=$R^5$=$R^{6a}$=$R^{7a}$=$R^9$=$R^{12}$=$R^{13}$=H, n=0, Z=$CH_2$)

and (2S)—N-(4-nitrophenyl)-2-(1-(R)-hydroxy-2,2,2-trifluoroethyl)pyrrolidine (Compound 117, Structure 5 of Scheme II, where $R^1$=nitro, $R^{10}$=1-(R)-hydroxy-2,2,2-trifluoroethyl, $R^2$=$R^3$=$R^4$=$R^5$=$R^{6a}$=$R^{7a}$=$R^9$=$R^{12}$=$R^{13}$=H, n=0, Z=CH$_2$)

To prepare these compounds, Compound 113 was oxidized using the method described Example 9 and the resulting compound was then used in place of Compound 110 in the method described in Example 10. Data for Compound 116: $^1$H NMR (CDCl$_3$, 400 MHz) 8.09 (m, 2H), 6.75 (m, 2H), 4.46 (m, 1H), 4.26 (br d, 1H, J=7.32 Hz), 3.66 (m, 1H), 3.45 (m, 1H), 2.70 (d, 1H, J=5.37 Hz), 2.55 (m, 1H), 2.38 (m, 1H), 2.0-2.15 (m, 2H). Data for Compound 117: $^1$H NMR (CDCl$_3$, 400 MHz) 8.16 (m, 2H), 6.85 (m, 2H), 4.35 (m, 1H), 3.95 (m, 1H), 3.68 (m, 1H), 3.36 (m, 1H), 2.55 (d, 1H, J=3.90 Hz), 2.24 (m, 1H), 2.1-2.2 (m, 3H).

Example 14

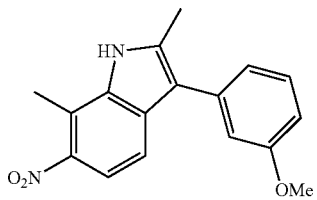 [SMILES: COc1cccc(-c2c(C)[nH]c3c(C)c([N+](=O)[O-])ccc23)c1]

3-(3-Methoxyphenyl)-6-nitro-2,7-dimethyl-1H-indole (Compound 118, Structure 8 of Scheme III, where $R^1$=nitro, $R^2$=$R^6$=Me, $R^4$=$R^5$=H, $R^7$=3-methoxyphenyl)

0.5 g (3.3 mmol) of 2-methyl-3-nitroaniline was dissolved in 15 mL of concentrated hydrochloric acid with stirring at 0° C. Sodium nitrite (1.6 g, 1.2 eq) in 5 mL water was then added dropwise. Thirty minutes later, tin chloride dihydrate (1.6 g, 2.1 eq) in 7 mL concentrated HCl was added. The reaction was stirred for 1 hour and then 7 mL of ethanol was added followed by 3-methoxyphenylacetone (1.3 mL, 2.5 eq). The reaction mixture was heated in a 100° C. oil bath. After 12 hours, the reaction was cooled, added to 50 mL of water, extracted into ethyl acetate (3×50 mL), dried and then concentrated. Chromatography (silica, 15-25% ethyl acetate/hexanes) afforded the title compound 0.132 g (15% yield) as a light yellow powder. $^1$H NMR (500 MHz, CDCl$_3$) δ 8.28 (s, 1H); 7.87 (d, J=8.8 Hz, 1H); 7.53 (d, J=8.8 Hz, 1H); 7.41 (dd, J=8.3, 7.6 Hz, 1H); 7.05 (ddd, J=7.6, 1.6, 1.0 Hz, 1H); 7.00 (dd, J=2.6, 1.6 Hz, 1H); 6.91 (ddd, J=8.3, 2.6, 1.0 Hz, 1H); 3.87 (s, 3H); 2.80 (s, 3H); 2.59 (s, 3H).

Example 15

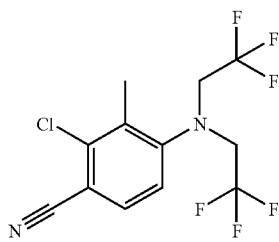 [SMILES: Cc1c(N(CC(F)(F)F)CC(F)(F)F)ccc(C#N)c1Cl]

4-[Bis-(2,2,2-trifluoroethyl)amino]-2-chloro-3-methylbenzonitrile (Compound 119, Structure 2 of Scheme I, where $R^1$=cyano, $R^2$=chloro, $R^3$=Me, $R^6$=$R^9$=trifluoromethyl, $R^4$=$R^5$=$R^7$=$R^8$=$R^{10}$=$R^{11}$=H)

This compound was prepared following the procedure described in example 3. $^1$H NMR (500 MHz, CDCl$_3$) 7.54 (d, J=8.3 Hz, 1H); 7.22 (d, J=8.3 Hz, 1H); 3.81 (q, J=8.6 Hz, 4H); 2.40 (s, 3H).

Example 16

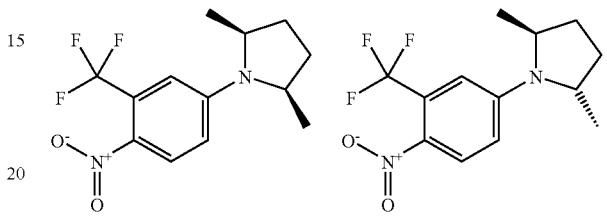

Cis-2,5-Dimethyl-1-(4-nitro-3-trifluoromethylphenyl)-pyrrolidine (Compound 120, Structure 11 of Scheme IV, where $R^1$=nitro, $R^2$=trifluoromethyl, $R^6$=$R^{10}$=Me, $R^3$=$R^4$=$R^5$=$R^7$=$R^8$=$R^9$=$R^{11}$=H, n=1) and trans-2,5-dimethyl-1-(4-nitro-3-trifluoromethylphenyl)-pyrrolidine (Compound 121, Structure 11 of Scheme IV, where $R^1$=nitro, $R^2$=trifluoromethyl, $R^7$=$R^{10}$=Me, $R^3$=$R^4$=$R^5$=$R^6$=$R^8$=$R^9$=$R^{11}$=H, n=1)

To a solution of 4-fluoro-2-(trifluoromethyl)nitrobenzene in 5 mL DMF was added 2,5-dimethylpyrrolidine (mixture of cis and trans isomers) followed by K$_2$CO$_3$. The mixture was stirred at room temperature for 30 minutes, and water was slowly added. The yellow precipitate was filtered and rinsed with water. The mixture of cis and trans dimethylpyrrolidines was partially separated by reverse phase HPLC. Data for compound 120: $^1$H NMR (500 MHz, CDCl$_3$) 8.07 (d, J=9.3 Hz, 1H) 6.88 (d, J=2.7 Hz, 1H) 6.63 (dd, J=9.3, 2.7 Hz, 1H) 3.99-3.91 (m, 2H) 2.22-2.14 (m, 2H) 1.88-1.80 (m, 2H) 1.33 (d, J=6.3 Hz, 6H) Data for compound 121: $^1$H NMR (500 MHz, CDCl$_3$) 8.07 (d, J=9.3 Hz, 1H) 6.85 (d, J=2.9 Hz, 1H) 6.61 (dd, J=9.3, 2.9 Hz, 1H) 4.14-4.09 (m, 2H) 2.35-2.26 (m, 2H) 1.76 (d, J=5.4 Hz, 1H) 1.33 (d, J=6.4 Hz, 1H) 1.17 (d, J=6.4 Hz, 6H).

Example 17

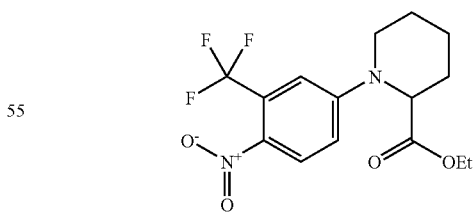

1-(4-Nitro-3-trifluoromethylphenyl)-piperidine-2-carboxylic acid ethyl ester (Compound 122, Structure 11 of Scheme IV, where $R^1$=nitro, $R^2$=trifluoromethyl, $R^6$=ethylcarboxylate, $R^3$=$R^4$=$R^5$=$R^7$=$R^8$=$R^9$=$R^{11}$=H, n=2)

This compound was prepared using the method described in Example 16. Data for Compound 122: $^1$H NMR (CDCl$_3$, 500 MHz) 8.02 (d, J=9.1 Hz, 1H) 7.15 (d, J=2.9 Hz, 1H) 6.91

(dd, J=9.1, 2.9 Hz, 1H) 4.66 (d, J=3.9 Hz, 1H) 4.18 (q, J=7.3 Hz, 2H) 3.78-3.73 (m, 1H) 3.31 (dt, J=3.5, 12.3 Hz, 1H) 2.38-2.33 (m, 1H) 1.97-1.82 (m, 2H) 1.81-1.71 (m, 2H) 1.66-1.58 (m, 3H) 1.50-1.40 (m, 1H) 1.24 (t, J=7.3 Hz, 1H).

Example 18

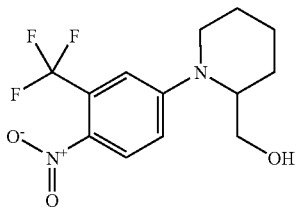 [SMILES: O=[N+]([O-])c1ccc(N2CCCCC2CO)cc1C(F)(F)F]

1-(4-Nitro-3-trifluoromethylphenyl)-4-(hydroxymethyl)-piperidine (Compound 123, Structure 11 of Scheme IV, where $R^1$=nitro, $R^2$=trifluoromethyl, $R^6$=hydroxymethyl, $R^3$=$R^4$=$R^5$=$R^7$=$R^8$=$R^9$=$R^{11}$=H, n=2)

This compound was prepared by reduction of compound 122 with lithium aluminum hydride. Data for Compound 123: $^1$H NMR (CDCl$_3$, 500 MHz) 8.03 (d, J=9.3 Hz, 1H) 7.20 (d, J=2.9 Hz, 1H) 6.98 (dd, J=9.3, 2.9 Hz, 1H) 4.27-4.20 (m, 1H) 3.96-3.90 (m, 1H) 3.82-3.73 (m, 1H) 3.23-3.13 (m, 1H) 1.92-1.51 (m, 7H).

Example 19

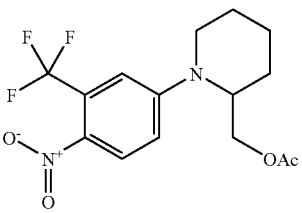 [SMILES: CC(=O)OCC1CCCCN1c1ccc([N+](=O)[O-])c(C(F)(F)F)c1]

(1-(3-trifluoromethyl-4-nitrophenyl)piperidin-2-yl)methyl acetate (Compound 124, Structure 11 of Scheme IV, where $R^1$=nitro, $R^2$=trifluoromethyl, $R^6$=acetoxymethyl, $R^3$=$R^4$=$R^5$=$R^7$=$R^8$=$R^9$=$R^{11}$=H, n=2)

This compound was prepared by acetylation of compound 123 with acetic anhydride. Data for Compound 124: $^1$H NMR (CDCl$_3$, 500 MHz) 8.03 (d, J=9.3 Hz, 1H) 7.19 (d, J=2.9 Hz, 1H) 6.94 (dd, J=9.3, 2.9 Hz, 1H) 4.54 (dd, J=11.2, 8.8 Hz, 1H) 4.46-4.39 (m, 1H) 4.09 (dd, J=11.2, 5.8 Hz, 1H) 3.73-3.67 (m, 1H) 3.19 (dt, J=3.4, 12.7 Hz, 1H) 1.88-1.71 (m, 4H) 1.85 (s, 3H) 1.67-1.60 (m, 2H).

Example 20

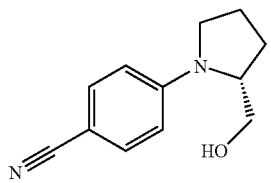 [SMILES: N#Cc1ccc(N2CCC[C@@H]2CO)cc1]

4-(2-Hydroxymethyl-pyrrolidin-1-yl)-benzonitrile (Compound 125, Structure 5 of Scheme II, where $R^1$=cyano, $R^6$=hydroxymethyl, $R^2$=$R^3$=$R^4$=$R^5$=$R^7$=$R^8$=$R^9$=$R^{11}$=H, n=0, Z=CH$_2$)

Prepared as in compound 108 of example 7 from (2R)—N-(4-cyanophenyl)-2-(dimethyl-tert-butylsilyloxymethyl) pyrrolidine. $^1$H NMR (CDCl$_3$, 500 MHz) 7.46 (d, 2H, J=9.0 Hz), 6.65 (d, 2H, J=9.0 Hz), 3.94 (dt, 1H, J=4.4, 6.8 Hz), 3.70 (ddd, 1H, J=5.7, 6.8, 10.9 Hz), 3.61 (ddd, J=10.9, 5.7, 4.4 Hz, 1H), 3.50 (m, 1H), 3.22 (m, 1H), 2.15-2.01 (m, 4H), 1.55 (t, J=5.7 Hz, 1H).

Example 21

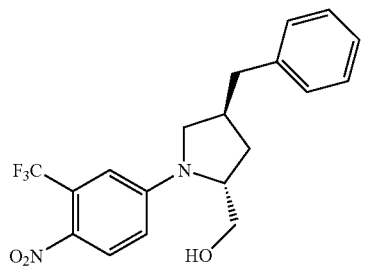 [SMILES: O=[N+]([O-])c1ccc(N2C[C@@H](Cc3ccccc3)C[C@@H]2CO)cc1C(F)(F)F]

4-Benzyl-2-hydroxymethyl-1-(4-nitro-3-trifluoromethylphenyl)-pyrrolidine (Compound 126, Structure 5 of Scheme II, where $R^1$=nitro, $R^2$=trifluoromethyl, $R^{10}$=hydroxymethyl, $R^{12}$=benzyl, $R^3$=$R^4$=$R^5$=$R^6$=$R^7$=$R^8$=$R^9$=$R^{11}$=H, n=0, Z=CH$_2$)

Prepared as in compound 108 from example 7. $^1$H NMR (CDCl$_3$, 500 MHz) 8.03 (d, J=9.3 Hz, 1H), 7.34 (td, J=7.6, 1.5 Hz, 2H), 7.26 (tt, J=7.6, 1.5 Hz, 1H), 7.21 (dd, J=7.6, 1.5 Hz, 2H), 6.92 (d, J=2.7 Hz, 1H), 6.69 (dd, J=9.3, 2.7 Hz, 1H), 4.07 (m, 1H), 3.72 (dt, J=11.0, 5.4 Hz, 1H), 3.66 (ddd, J=11.0, 6.6, 5.4 Hz, 1H), 3.61 (dd, J=9.7, 7.2 Hz, 1H), 3.02 (t, J=9.7 Hz, 1H), 2.84 (m, 1H), 2.79 (m, 2H), 2.18 (dd, J=12.7, 5.7 Hz, 1H), 1.87 (ddd, J=12.7, 11.0, 8.1 Hz, 1H), 1.55 (t, J=5.4 Hz, 1H).

Example 22

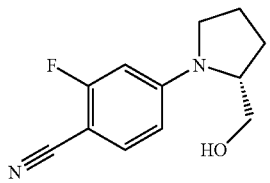 [SMILES: N#Cc1ccc(N2CCC[C@@H]2CO)cc1F]

2-Fluoro-4-(2-hydroxymethyl-pyrrolidin-1-yl)-benzonitrile (Compound 127, Structure 5 of Scheme II, where $R^1$=cyano, $R^2$=fluoro, $R^{10}$=hydroxymethyl, $R^3$=$R^4$=$R^5$=$R^6$=$R^7$=$R^8$=$R^9$=$R^{11}$=H, n=0, Z=CH$_2$)

Prepared as in compound 108 from example 7. $^1$H NMR (CDCl$_3$, 500 MHz) 7.35 (dd, J=8.8, 7.8 Hz, 1H), 6.44 (dd, J=8.8, 2.4 Hz, 1H), 6.37 (dd, J=12.7, 2.4 Hz, 1H), 3.92 (m, 1H), 3.70 (m, 1H), 3.62 (m, 1H), 3.47 (m, 1H), 3.22 (m, 1H), 2.16-2.01 (m, 4H).

3.75-3.68 (m, 2H), 2.52 (ddd, J=14.2, 9.4, 4.8 Hz, 1H), 2.39 (ddd, J=14.2, 2.2, 1.0 Hz, 1H), 1.34 (t, J=7.2 Hz, 3H).

Example 23

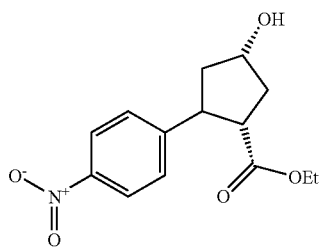

4-Hydroxy-1-(4-nitrophenyl)-pyrrolidine-2-carboxylic acid ethyl ester (Compound 128, Structure 5 of Scheme II, where $R^1$=nitro, $R^{12}$=hydroxyl, $R^{10}$=ethylcarboxylate, $R^2=R^3=R^4=R^5=R^6=R^7=R^8=R^9=R^{11}$=H, n=0, Z=CH$_2$)

4-Fluoronitrobenzene (0.28 mL, 2.65 mmol), 4-hydroxy-pyrrolidine-2-carboxylic acid ethyl ester (419 mg, 2.65 mmol), and sodium bicarbonate (222 mg, 2.65 mmol) were dissolved in 5 mL dry DMF and heated to 80° C. After 24 h at this temperature, the reaction was cooled and water and ethyl acetate were added. The organic phase washed with brine, dried (MgSO$_4$), and concentrated. Flash chromatography (65-75% ethyl acetate/hexanes) gave 260 mg (35% yield) of the desired product. $^1$H NMR (CDCl$_3$, 500 MHz) 8.15 (d, J=9.3 Hz, 2H), 6.54 (d, J=9.3 Hz, 2H), 4.60 (m, 1H), 4.41 (d, J=9.2 Hz, 1H), 4.31 (dq, J=10.8, 7.1 Hz, 1H), 4.29 (dq, J=10.8, 7.1 Hz, 1H), 3.73 (dt, J=11.0, 1.2 Hz, 1H), 3.70 (dd, J=11.0, 4.2 Hz, 1H), 2.51 (ddd, J=14.2, 9.2, 4.2 Hz, 1H), 2.35 (dd, J=14.2, 1.2 Hz, 1H), 1.34 (t, J=7.1 Hz, 3H).

Example 24

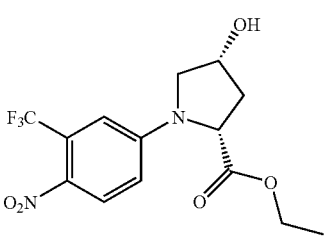 [SMILES: CCOC(=O)[C@H]1C[C@@H](O)CN1c1ccc([N+](=O)[O-])c(C(F)(F)F)c1]

4-Hydroxy-1-(4-nitro-3-trifluoromethylphenyl)-pyrrolidine-2-carboxylic acid ethyl ester (Compound 129, Structure 5 of Scheme II, where $R^1$=nitro, $R^2$=trifluoromethyl $R^{12}$=hydroxyl, $R^{10}$=ethylcarboxylate, $R^3=R^4=R^5=R^6=R^7=R^8=R^9=R^{11}$=H, n=0, Z=CH$_2$)

Prepared as in example 23. $^1$H NMR (CDCl$_3$, 500 MHz) 8.06 (d, J=9.1 Hz, 1H), 6.92 (d, J=2.6 Hz, 1H), 6.67 (dd, J=9.1, 2.6 Hz, 1H), 4.62 (m, 1H), 4.43 (dd, J=9.4, 1.0 Hz, 1H), 4.34 (dq, J=10.7, 7.2 Hz, 1H), 4.27 (dq, J=10.7, 7.2 Hz, 1H),

Example 25

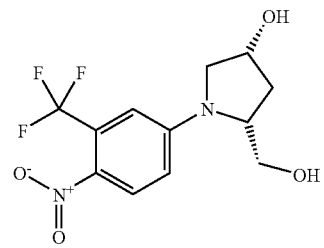

5-Hydroxymethyl-1-(4-nitro-3-trifluoromethylphenyl)-pyrrolidin-3-ol (Compound 130, Structure 5 of Scheme II, where $R^1$=nitro, $R^2$=trifluoromethyl, $R^{12}$=hydroxyl, $R^{10}$=hydroxymethyl, $R^3=R^4=R^5=R^6=R^7=R^8=R^9=R^{11}$=H, n=0, Z=CH$_2$)

Compound 129 (75 mg, 0.21 mmol) was dissolved in 2 mL dry THF and cooled to 0° C. under N$_2$ atmosphere. LAH was added (0.43 mL of a 1.0M solution in THF) and the reaction was stirred for 10 min. as judged complete by TLC. Careful quenching with Rochelle's salt was followed by an extractive workup. Flash chromatography (5% MeOH/CH$_2$Cl$_2$) gave 18 mg (25%) of the product as a yellow oil. $^1$H NMR (CDCl$_3$, 500 MHz) 8.02 (d, J=9.2 Hz, 1H), 6.89 (d, J=2.7 Hz, 1H), 6.66 (dd, J=9.2, 2.7 Hz, 1H), 4.57 (m, 2H), 4.22-4.17 (m, 2H), 3.75 (m, 1H), 3.62 (m, 2H), 2.86 (br s, 1H), 2.55 (ddd, J=14.3, 9.8, 5.0 Hz, 1H), 2.16 (d, J=14.3 Hz, 1H).

Example 26

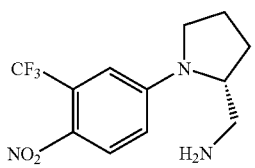

2-(Aminomethyl)-1-(4-Nitro-3-trifluoromethylphenyl)-pyrrolidine (Compound 131, Structure 5 of Scheme II, where $R^1$=nitro, $R^2$=trifluoromethyl, $R^{10}$=aminomethyl, $R^3=R^4=R^5=R^{6a}=R^{7a}=R^9=R^{12}=R^{13}$=H, n=0, Z=CH$_2$)

To a solution of aldehyde 110 from example 9 (359 mg, 1.24 mmol) in 8 mL dry MeOH was added ammonium acetate (480 mg, 6.22 mmol) followed by NaCNBH$_3$ (155 mg, 2.48 mmol) at ambient temperature. The reaction was stirred for 24 h at this temperature and then concentrated to ca. 4 mL in vacuo and diluted with saturated aqueous NaHCO$_3$. Water and ethyl acetate were added and the organic phase washed with brine, dried (MgSO$_4$), and concentrated. Flash chromatography (65-90% ethyl acetate/hexanes) gave 210 mg (59% yield) of the product as a yellow solid. $^1$H NMR (CDCl$_3$, 500 MHz) 8.03 (d, J=9.0 Hz, 1H), 6.96 (d, J=2.9 Hz, 1H), 6.67 (dd, J=9.0, 2.9 Hz, 1H, 3.97 (m, 1H), 3.50 (ddd, J=9.8, 6.4, 3.7

Hz, 1H), 3.29 (dt, J=9.8, 8.4 Hz, 1H), 2.78 (dd, J=12.2, 4.9 Hz, 1H), 2.69 (dd, J=12.2, 7.8 Hz, 1H), 2.15-2.03 (m, 4H).

Example 27

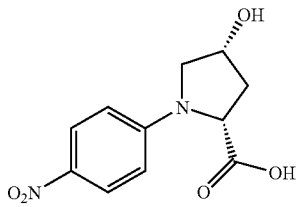 [SMILES: O=C(O)[C@H]1C[C@@H](O)CN1c1ccc([N+](=O)[O-])cc1]

4-Hydroxy-1-(4-nitrophenyl)-pyrrolidine-2-carboxylic acid (Compound 132, Structure 5 of Scheme II, where $R^1$=nitro, $R^{12}$=hydroxyl, $R^{10}$=carboxylic acid, $R^2$=$R^3$=$R^4$=$R^5$=$R^6$=$R^7$=$R^8$=$R^9$=$R^{11}$=H, n=0, Z=$CH_2$)

Compound 128 (70 mg, 0.25 mmol) was dissolved in 3 mL EtOH and KOH (28 mg, 0.5 mmol) was added. The reaction was heated to reflux and stirred for 2 h. The reaction was cooled to room temperature and concentrated in vacuo. 10% NaOH (5 mL) was added and extracted with $CH_2Cl_2$ (2 times). The aqueous phase was adjusted to ~pH 2 with 10% HCl, and then was extracted with ethyl acetate (2 times). The organic layers were combined, dried ($MgSO_4$), and concentrated. 10 mg of the crude material was purified using preparatory HPLC (30:70 water/MeOH) to give compound 132. $^1$H NMR (Acetone-$d_6$, 500 MHz) 8.09 (d, J=9.3 Hz, 2H), 6.69 (d, J=9.3 Hz, 2H), 4.65 (m, 1H), 4.55 (dd, J=9.3, 1.2 Hz, 1H), 3.72 (dd, J=11.0, 4.6 Hz, 1H), 3.60 (d, J=11.0 Hz, 1H), 2.58 (ddd, J=13.5, 9.3, 4.6 Hz, 1H), 2.41 (dd, J=13.5, 1.2 Hz, 1H).

Example 28

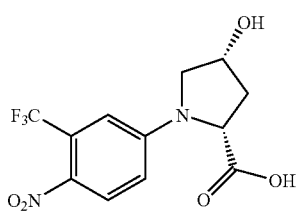 [SMILES: O=C(O)[C@H]1C[C@@H](O)CN1c1ccc([N+](=O)[O-])c(C(F)(F)F)c1]

4-Hydroxy-1-(4-nitro-3-trifluoromethylphenyl)-pyrrolidine-2-carboxylic acid (Compound 133, Structure 5 of Scheme II, where $R^1$=nitro, $R^2$=trifluoromethyl $R^{12}$=hydroxyl, $R^{10}$-carboxylic acid, $R^3$=$R^4$=$R^5$=$R^6$=$R^7$=$R^8$=$R^9$=$R^{11}$=H, n=0, Z=$CH_2$)

Prepared as in example 27. $^1$H NMR (Acetone-$d_6$, 500 MHz) 8.09 (d, J=9.2 Hz, 1H), 7.01 (d, J=2.7 Hz, 1H), 6.91 (dd, J=9.2, 2.7 Hz, 1H), 4.69 (dd, J=8.9, 1.8 Hz, 1H), 4.67 (m, 1H), 3.78 (dd, J=11.0, 4.5 Hz, 1H), 3.63 (dt, J=11.0, 1.3 Hz, 1H), 2.58 (ddd, J=13.4, 8.9, 4.5 Hz, 1H), 2.47 (dd, J=13.4, 1.8 Hz, 1H).

Example 29

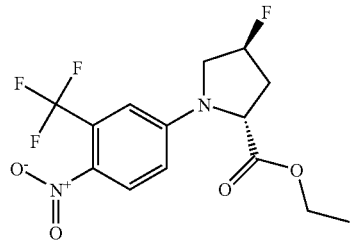 [SMILES: CCOC(=O)[C@H]1C[C@H](F)CN1c1ccc([N+](=O)[O-])c(C(F)(F)F)c1]

4-Fluoro-1-(4-nitro-3-trifluoromethylphenyl)-pyrrolidine-2-carboxylic acid ethyl ester (Compound 134, Structure 5 of Scheme II, where $R^1$=nitro, $R^2$=trifluoromethyl $R^{12}$=fluoro, $R^{10}$=ethylcarboxylate, $R^3$=$R^4$=$R^5$=$R^6$=$R^7$=$R^8$=$R^9$=$R^{11}$=H, n=0, Z=$CH_2$)

Compound 129 (66 mg, 0.19 mmol) was dissolved in 2 mL dry $CH_2Cl_2$ and cooled to $-78°$ C. DAST (0.05 mL, 0.57 mmol) was added via syringe and stirring was continued at this temperature for 1 hour. The cooling bath was removed, allowing the reaction to reach ambient temperature, and stirring was continued for an additional 1 hour. The reaction was quenched with $NaHCO_3$ and ethyl acetate was added. The organic phase was separated, dried ($MgSO_4$), and concentrated. Preparatory HPLC (20:80 water/acetonitrile) gave 10 mg (15% yield) of the desired product. $^1$H NMR (CDCl$_3$, 500 MHz) 8.05 (d, J=9.2 Hz, 1H), 6.87 (d, J=2.7 Hz, 1H), 6.65 (dd, J=9.2, 2.7 Hz, 1H), 5.45 (dm, J=52.5 Hz, 1H), 4.61 (t, J=7.8 Hz, 1H), 4.27 (dq, J=10.8, 7.1 Hz, 1H), 4.20 (dq, J=10.8, 7.1 Hz, 1H), 3.96-3.81 (m, 2H), 2.83 (dddt, J=20.2, 14.4, 7.8, 1.9 Hz, 1H), 2.40 (dddd, J=35.1, 14.4, 7.8, 4.4 Hz, 1H), 1.27 (t, J=7.1 Hz, 3H).

Example 30

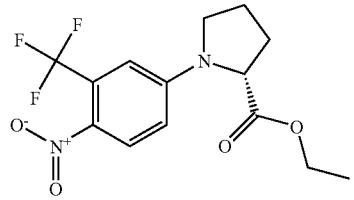 [SMILES: CCOC(=O)[C@H]1CCCN1c1ccc([N+](=O)[O-])c(C(F)(F)F)c1]

1-(4-Nitro-3-trifluoromethylphenyl)-pyrrolidine-2-carboxylic acid ethyl ester (Compound 133, Structure 5 of Scheme II, where $R^1$=nitro, $R^2$=trifluoromethyl $R^{10}$=ethylcarboxylate, $R^3$=$R^4$=$R^5$=$R^6$=$R^7$=$R^8$=$R^9$=$R^{11}$=$R^{12}$=H, n=0, Z=$CH_2$)

Prepared as in example 16. $^1$H NMR (CDCl$_3$, 500 MHz) 8.05 (d, 1H, J=9.2 Hz), 6.85 (d, 1H, J=2.6 Hz), 6.60 (dd, 1H, J=2.6, 9.2 Hz), 4.37 (dd, 1H, J=2.4, 8.5 Hz), 4.25 (dq, 1H, J=7.1, 10.8 Hz), 4.19 (dq, 1H, J=7.1, 10.8 Hz), 3.68 (m, 1H), 3.50 (m, 1H), 2.37 (m, 1H), 2.31-2.11 (m, 3H), 1.27 (t, 3H, J=7.1 Hz).

Example 31

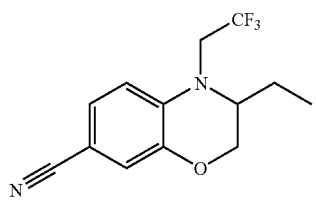 [SMILES: CCC1COc2cc(C#N)ccc2N1CC(F)(F)F]

3-Ethyl-4-(2,2,2-trifluoro-ethyl)-3,4-dihydro-2H-benzo[1,4]oxazine-7-carbonitrile (Compound 136, Structure 14 of Scheme V, where $R^1$=cyano, $R^8$=2,2,2-trifluoroethyl, $R^6$=ethyl, $R^2$=$R^3$=$R^5$=$R^7$=$R^{12}$=$R^{13}$=H)

Step A: 3-Fluoro-4-(1-hydroxymethyl-propylamino)-benzonitrile

A 100 mL round bottom flask was charged with 3,4-difluorobenzonitrile (2.013 g, 14.5 mmol), sodium bicarbonate (1.59 g, 18.9 mmol), and L-(−)-2-amino-1-butanol (1.33 mL, 14.5 mmol). The contents were then dissolved in 40 mL N,N-dimethylformamide (anhydrous). The flask was heated to 90° C. and stirred overnight under $N_2$. The reaction mixture was cooled to room temperature, poured onto water, and extracted with EtOAc (2 times). The organic layers were combined, washed with brine, dried ($MgSO_4$), and concentrated. The resulting residue was purified via silica gel chromatography (gradient from 5% EtOAc/Hexanes to 10% EtOAc/Hexanes followed by 50% EtOAc/Hexanes) to afford 1.00 g (33% yield) of the title compound. $^1H$ NMR (CDCl$_3$, 500 MHz) δ: 7.28 (m, 1H), 7.21 (dd, J=11.3, 1.8 Hz, 1H), 6.72 (t, J=8.5 Hz, 1H), 4.49 (s, 1H), 3.77 (m, 1H), 3.68 (dt, J=10.0, 5.3 Hz, 1H), 3.48 (m, 1H), 1.87 (m, 1H), 1.72 (dqn, J=14.5, 7.5 Hz, 1H), 1.60 (dqn, J=14.5, 7.5 Hz, 1H), 1.00 (t, J=7.5 Hz, 3H).

Step B: 4-(N-(2,2,2-trifluoroethyl)-N-(1-hydroxybut-2-yl)amino)-3-fluorobenzonitrile A 25 mL round bottom flask fitted with a Dean-Stark trap, reflux condenser, and $N_2$ line was charged with 245.3 mg (1.17 mmol) of 3-Fluoro-4-(1-hydroxymethyl-propylamino)-benzonitrile. p-Toluenesulfonic acid (27.4 mg, 0.144 mmol) was then added, along with trifluoroacetaldehyde ethyl hemiacetal (859.2 mg, 5.96 mmol) in 4 mL toluene. Toluene was then added to the Dean-Stark trap and the reaction was heated in an oil bath at 125° C. overnight. The reaction was cooled to room temperature, poured onto water, and the water extracted with EtOAc (2×). The organic layers were combined, washed with brine, dried ($MgSO_4$), and concentrated. The resulting residue was purified via silica gel chromatography (10% EtOAc/Hexanes) to afford 277.8 mg (82%) of 4-(4-Ethyl-2-trifluoromethyl-oxazolidin-3-yl)-3-fluoro-benzonitrile as a mixture of diastereomers. This was dissolved in 8 mL CHCl$_3$ (8 mL) and Et$_3$SiH (0.62 mL, 3.88 mmol) was then added via syringe and the resulting solution was cooled to −78° C. TiCl$_4$ (1M in dichloromethane, 1.95 mL) was then added dropwise via syringe. The reaction was slowly warmed to room temperature and stirred for 18 hours. The reaction mixture was poured onto water, and the water extracted with EtOAc (2×). The organic layers were combined, washed with brine, dried ($MgSO_4$), and concentrated. The resulting residue was purified via silica gel chromatography (gradient from 5% EtOAc/Hexanes to 15% EtOAc/Hexanes followed by 50% EtOAc/Hexanes) to afford 99.8 mg (36% yield) of 4-(N-(2,2,2-trifluoroethyl)-N-(1-hydroxybut-2-yl)amino)-3-fluorobenzonitrile. $^1H$ NMR (CDCl$_3$, 500 MHz) δ: 7.39-7.34 (m, 2H), 7.32 (m, 1H), 4.05 (m, 1H), 3.83 (m, 1H), 3.73 (m, 1H), 3.65 (m, 1H), 3.46 (m, 1H), 1.96 (m, 1H), 1.55 (m, 2H), 0.94 (t, J=7.4 Hz, 3H).

Step C: 3-Ethyl-4-(2,2,2-trifluoroethyl)-3,4-dihydro-2H-benzo[1,4]oxazine-7-carbonitrile A 25 mL round bottom flask was charged with sodium hydride (60% dispersion in mineral oil, 29 mg, 1.21 mmol) which was then suspended in 3 mL THF (anhydrous). To the reaction mixture was then added 4-(N-(2,2,2-trifluoroethyl)-N-(1-hydroxybut-2-yl)amino)-3-fluorobenzonitrile (99.8 mg, 0.344 mmol) via syringe in 5 mL THF. The flask was heated to 50° C. and stirred for 5 hours. The flask was then cooled to room temperature and stirred overnight. The reaction mixture was then poured onto water, and the water extracted with EtOAc (2×). The organic layers were combined, washed with brine, dried ($MgSO_4$), and concentrated. The resulting residue was purified via silica gel chromatography (gradient from 5% EtOAc/Hexanes to 10% EtOAc/hexanes) to afford 44.9 mg (48%) of Compound 136. $^1H$ NMR (CDCl$_3$, 500 MHz) δ: 7.15 (dd, J=8.5, 2.0 Hz, 1H), 7.08 (d, J=2.0 Hz, 1H), 6.73 (d, J=8.5 Hz, 1H), 4.30 (dd, J=11.0, 2.0 Hz, 1H), 4.05 (dq, J=16.4, 8.1 Hz, 1H), 4.00 (ddd, J=11.0, 2.0, 0.5 Hz, 1H), 3.75 (dq, J=16.4, 8.9 Hz, 1H), 3.33 (ddt, J=8.2, 6.2, 2.0 Hz, 1H), 1.68-1.62 (m, 2H), 0.99 (t, J=7.4 Hz, 3H).

Example 32

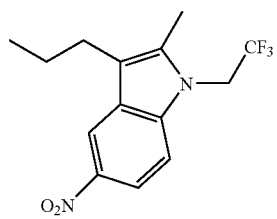 [SMILES: CCCc1c(C)n(CC(F)(F)F)c2ccc([N+](=O)[O-])cc12]

2-Methyl-5-nitro-3-propyl-1-(2,2,2-trifluoroethyl)-1H-indole (Compound 137, Structure 18 of Scheme VI, where $R^1$=nitro, $R^7$=n-propyl, $R^6$=methyl, $R^8$=2,2,2-trifluoroethyl, $R^2$=$R^4$=$R^5$=H)

In a 200 ml 2-neck round bottom flask, equipped with a magnetic stirrer and a cold water condenser, 4-nitrophenylhydrazine was dissolved in 75 mL concentrated hydrochloric acid and stirred at room temperature for 15 minutes. A solution of 2-hexanone (5 mL) in ethanol (25 mL) was added slowly and the reaction flask was heated in an oil bath at 105° C. for 18 h. The mixture was cooled to room temperature and water (100 mL) was added. The mixture was extracted with EtOAc. The organic layer washed with saturated sodium bicarbonate solution, water, and brine solutions and evaporated to dryness. The oily residue was absorbed on silica gel and purified by silica gel chromatography with 20% EtOAc in Hexane solution to give 2-methyl-5-nitro-3-propyl-1H-indole. This indole product was dissolved in trifluoroacetic acid (10 mL) and 1 pellet sodium borohydride (0.7 g) was added and the reaction was stirred at room temperature for 18 h. Water (10 mL) was carefully added and the reaction mixture was extracted twice with EtOAc (15 mL). The organic layer washed with brine and dried over MgSO$_4$, and purified by flash column chromatography on silica gel eluted with 20% EtOAc in hexanes to give 280 mg of 2-methyl-5-nitro-3-propyl-1-(2,2,2-trifluoroethyl)-2,3-dihydro-1H-indole.

In a 10 ml round bottom flask, equipped with a magnetic stirrer and under a dry nitrogen atmosphere, 20 mg of 2-methyl-5-nitro-3-propyl-1-(2,2,2-trifluoro-ethyl)-2,3-dihydro-1H-indole from last step was dissolved in EtOAc (3 mL), and 50 mg of DDQ was added to the solution and stirred at room temperature until TLC analysis (20% EtOAc in hexanes) showed no more starting material. The reaction mixture was diluted with ethyl acetate (10 mL) and washed with saturated sodium bicarbonate solution, water, and then brine and dried over MgSO$_4$. The organic layer was absorbed on silica gel and purified by flash column chromatography, eluting with 10% EtOAc in hexanes. 12 mg of 2-methyl-5-nitro-3-propyl-1-(2,2,2-trifluoroethyl)-1H-indole was obtained. $^1$H NMR (500 MHz, CDCl$_3$) δ 8.50 (d, J=2.0 Hz, 1H), 8.14 (dd, J=9.3, 2.0 Hz, 1H), 7.36 (d, J=9.3 Hz, 1H), 4.69 (q, J=8.5 Hz, 2H), 2.76 (t, J=7.6 Hz, 2H), 2.44 (s, 3H), 1.72-1.64 (m, 2H), 2.96 (t, J=7.3 Hz, 3H).

Example 33

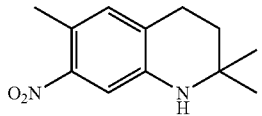

2,2,6-Trimethyl-7-nitro-1,2,3,4-tetrahydro-quinoline (Compound 138, Structure 20 of Scheme VII, where R$^1$=nitro, R$^2$=R$^6$=R$^7$=methyl, R$^3$=R$^4$=H)

A solution of 2,2,6-trimethyl-1,2,3,4-tetrahydroquinoline (0.66 g, 3.8 mmol) in 10 mL of concentrated sulfuric acid was cooled to 0° C. in an ice bath. To this solution was added dropwise 1.0 mL 90% fuming nitric acid. The resulting mixture was stirred at 0° C. for 30 min., poured onto 150 mL of ice-water, neutralized to pH=7 with K$_2$CO$_3$ and extracted with CH$_2$Cl$_2$ (3×200 mL). The combined organic layers were washed with water (2×300 mL), saturated aqueous NaHCO$_3$ (300 mL) and brine (300 mL). The solution was dried over MgSO$_4$, filtered and concentrated under reduced pressure. The residue was purified by flash column chromatography (Silica gel, 15 to 20% ethyl acetate/hexane gradient elution) to give 2,2,6-trimethyl-7-nitro-1,2,3,4-tetrahydro-quinoline. $^1$H NMR (500 MHz, CDCl$_3$): 8.03 (s, 1H), 7.05 (s, 1H), 2.85 (td, J=6.6, 1.1 Hz, 2H), 2.17 (s, 3H), 1.76 (t, J=6.6 Hz, 2H), 1.35 (s, 6H).

While description of the exemplary embodiments and processing conditions have been provided, the scope of the claimed subject matter is not to be limited thereto or thereby. Various modifications and alterations of the claimed subject matter will be apparent to those skilled in the art without departing from the scope and spirit of the claimed subject matter.

What is claimed is:
1. A compound of Formula II:

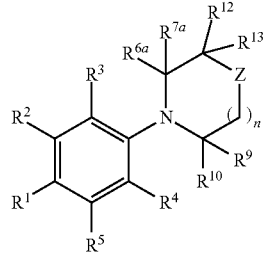

wherein:
R$^1$ is selected from among SR$^A$, NO$_2$, CN, CF$_3$, COR$^A$, CONR$^A$R$^B$, SOR$^A$, and SO$_2$R$^A$;
R$^2$ is selected from among F, Cl, Br, I, SR$^A$, NO$_2$, CF$_3$, COR$^A$, CO$_2$R$^A$, CONR$^A$R$^B$, SOR$^A$, SO$_2$R$^A$, SO$_2$NR$^A$R$^B$, NHCOR$^A$, and NHCONR$^A$R$^B$;
R$^3$ and R$^4$ each independently is selected from among hydrogen, F, Cl, OR$^A$, an optionally substituted C$_1$-C$_4$ alkyl, and CF$_3$;
R$^3$ is selected from among hydrogen, F, Cl and CF$_3$;
R$^{6a}$ and R$^{7a}$ each independently is selected from among hydrogen, an optionally substituted C$_1$-C$_6$ alkyl, CF$_3$, an optionally substituted C$_1$-C$_6$ heteroalkyl, an optionally substituted C$_2$-C$_6$ alkynyl, and an optionally substituted C$_2$-C$_6$ alkenyl;
R$^9$ is selected from an optionally substituted C$_1$-C$_8$ alkyl, an optionally substituted C$_2$-C$_8$ alkenyl, CF$_3$, an optionally substituted C$_2$-C$_8$ haloalkenyl, an optionally substituted C$_2$-C$_8$ heteroalkenyl, an optionally substituted C$_2$-C$_8$ alkynyl, an optionally substituted C$_2$-C$_8$ haloalkynyl, an optionally substituted C$_2$-C$_8$ heteroalkynyl, an optionally substituted heteroaryl, CH(R$^D$)OR$^A$, CH(R$^D$)NR$^A$R$^B$, COR$^A$, and (CH$_2$)$_m$R$^C$;
R$^{10}$ is selected from among hydrogen, an optionally substituted C$_1$-C$_6$ alkyl, CF$_3$, an optionally substituted C$_1$-C$_6$ heteroalkyl, an optionally substituted C$_2$-C$_6$ alkynyl, and an optionally substituted C$_2$-C$_6$ alkenyl;
R$^{12}$ and R$^{13}$ each independently is selected from among hydrogen, F, Cl, OR$^A$, NR$^A$R$^B$, SR$^A$, an optionally substituted C$_1$-C$_6$ alkyl, CF$_3$, an optionally substituted C$_1$-C$_6$ heteroalkyl, an optionally substituted C$_2$-C$_6$ alkynyl, an optionally substituted C$_2$-C$_6$ alkenyl, and (CH$_2$)$_m$R$^C$;
R$^A$ is selected from among hydrogen, an optionally substituted C$_1$-C$_4$ alkyl and CF$_3$;
R$^B$ is selected from among hydrogen, an optionally substituted C$_1$-C$_4$ alkyl, CF$_3$, and an optionally substituted C$_1$-C$_4$ heteroalkyl;
R$^C$ is selected from among an optionally substituted aryl and an optionally substituted heteroaryl that is optionally substituted with a substituent selected from among F, Cl, Br, I, CN, OR$^A$, NO$_2$, NR$^A$R$^B$, SR$^A$, SOR$^A$, SO$_2$R$^A$, an optionally substituted C$_1$-C$_4$ alkyl, CF$_3$, and an optionally substituted C$_1$-C$_4$ heteroalkyl;
R$^D$ is selected from among hydrogen, an optionally substituted C$_1$-C$_4$ alkyl, CF$_3$, and an optionally substituted C$_1$-C$_4$ heteroalkyl;
Z is CR$^A$R$^B$;
n is 0; and
m is 1 or 2;
or a pharmaceutically acceptable salt thereof.

2. The compound of claim 1, wherein:

$R^1$ is selected from among $NO_2$, CN and $CONR^A R^B$;

$R^2$ is selected from among F, Cl, Br, I, $OR^A$, $SR^A$, $NO_2$, $CF_3$, $COR^A$, $CO_2R^A$, $CONR^A R^B$, $SOR^A$, $SO_2R^A$, $SO_2NR^A R^B$, $NHCOR^A$, and $NHCONR^A R^B$;

$R^3$ and $R^4$ each independently is selected from among hydrogen, F, Cl, $OR^A$, an optionally substituted $C_1$-$C_4$ alkyl, and $CF_3$;

$R^5$ is selected from among hydrogen, F, Cl, an optionally substituted $C_1$-$C_4$ alkyl and $CF_3$;

$R^{6a}$ and $R^{7a}$ each independently is selected from among hydrogen, an optionally substituted $C_1$-$C_6$ alkyl, $CF_3$, an optionally substituted $C_1$-$C_6$ heteroalkyl, an optionally substituted $C_1$-$C_6$ heterohaloalkyl, an optionally substituted $C_2$-$C_6$ heterohaloalkenyl, an optionally substituted $C_2$-$C_6$ heterohaloalkynyl, an optionally substituted $C_2$-$C_6$ alkynyl, and an optionally substituted $C_2$-$C_6$ alkenyl;

$R^9$ is selected from among an optionally substituted $C_1$-$C_8$ alkyl, an optionally substituted $C_2$-$C_8$ alkenyl, $CF_3$, an optionally substituted $C_2$-$C_8$ haloalkenyl, an optionally substituted $C_2$-$C_8$ heteroalkenyl, an optionally substituted $C_2$-$C_8$ alkynyl, an optionally substituted $C_2$-$C_8$ haloalkynyl, an optionally substituted $C_2$-$C_8$ heteroalkynyl, an optionally substituted $C_2$-$C_6$ heterohaloalkenyl, an optionally substituted $C_2$-$C_6$ heterohaloalkynyl, an optionally substituted heteroaryl, $CH(R^D)OR^A$, $CH(R^D)NR^A R^B$, $COR^A$, and $(CH_2)_m R^C$;

$R^{10}$ each independently is selected from among hydrogen, an optionally substituted $C_1$-$C_6$ alkyl, $CF_3$, an optionally substituted $C_1$-$C_6$ heteroalkyl, an optionally substituted $C_1$-$C_6$ heterohaloalkyl, an optionally substituted $C_2$-$C_6$ heterohaloalkenyl, an optionally substituted $C_2$-$C_6$ heterohaloalkynyl, an optionally substituted $C_2$-$C_6$ alkynyl, and an optionally substituted $C_2$-$C_6$ alkenyl;

$R^{12}$ and $R^{13}$ each independently is selected from among hydrogen, F, Cl, $OR^A$, $NR^A R^B$, $SR^A$, an optionally substituted $C_1$-$C_6$ alkyl, $CF_3$, an optionally substituted $C_1$-$C_6$ heteroalkyl, an optionally substituted $C_1$-$C_6$ heterohaloalkyl, an optionally substituted $C_2$-$C_6$ heterohaloalkenyl, an optionally substituted $C_2$-$C_6$ heterohaloalkynyl, an optionally substituted $C_2$-$C_6$ alkynyl, an optionally substituted $C_2$-$C_6$ alkenyl, and $(CH_2)_m R^C$;

$R^A$ is selected from among hydrogen, an optionally substituted $C_1$-$C_4$ alkyl and $CF_3$;

$R^B$ is selected from among hydrogen, an optionally substituted $C_1$-$C_4$ alkyl, $CF_3$, and an optionally substituted $C_1$-$C_4$ heteroalkyl;

$R^C$ is selected from among an optionally substituted aryl and an optionally substituted heteroaryl that is optionally substituted with a substituent selected from among F, Cl, Br, I, CN, $OR^A$, $NO_2$, $NR^A R^B$, $SR^A$, $SOR^A$, $SO_2R^A$, an optionally substituted $C_1$-$C_4$ alkyl, $CF_3$, and an optionally substituted $C_1$-$C_4$ heteroalkyl;

$R^D$ is selected from among hydrogen, an optionally substituted $C_1$-$C_4$ alkyl, $CF_3$, and an optionally substituted $C_1$-$C_4$ heteroalkyl;

Z is $CR^A R^B$;

n is 0; and m is 1 or 2.

3. The compound of claim 1, wherein $R^1$ is $NO_2$ or CN.

4. The compound of claim 1, wherein $R^1$ is $NO_2$.

5. A compound of Formula II:

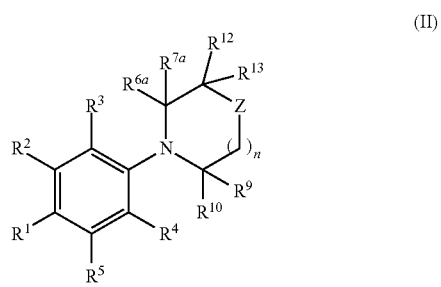

(II)

wherein:

$R^1$ is CN;

$R^2$ is selected from among F, Cl, Br, I, $SR^A$, $NO_2$, $CF_3$, $COR^A$, $CO_2R^A$, $CONR^A R^B$, $SOR^A$, $SO_2R^A$, $SO_2NR^A R^B$, $NHCOR^A$, and $NHCONR^A R^B$;

$R^3$ and $R^4$ each independently is selected from among hydrogen, F, Cl, $OR^A$, an optionally substituted $C_1$-$C_4$ alkyl, and $CF_3$;

$R^5$ is selected from among hydrogen, F, Cl and $CF_3$;

$R^{6a}$ and $R^{7a}$ each independently is selected from among hydrogen, an optionally substituted $C_1$-$C_6$ alkyl, $CF_3$, an optionally substituted $C_1$-$C_6$ heteroalkyl, an optionally substituted $C_2$-$C_6$ alkynyl, and an optionally substituted $C_2$-$C_6$ alkenyl;

$R^9$ is selected from an optionally substituted $C_1$-$C_8$ alkyl, an optionally substituted $C_2$-$C_8$ alkenyl, $CF_3$, an optionally substituted $C_2$-$C_8$ haloalkenyl, $C_1$-$C_8$ heteroalkyl, an optionally substituted $C_2$-$C_8$ heteroalkenyl, an optionally substituted $C_2$-$C_8$ alkynyl, an optionally substituted $C_2$-$C_8$ haloalkynyl, an optionally substituted $C_2$-$C_8$ heteroalkynyl, an optionally substituted heteroaryl, $CH(R^D)OR^A$, $CH(R^D)NR^A R^B$, $COR^A$, $CO_2R^A$, and $(CH_2)_m R^C$;

$R^{10}$ is selected from among hydrogen, an optionally substituted $C_1$-$C_6$ alkyl, $CF_3$, an optionally substituted $C_1$-$C_6$ heteroalkyl, an optionally substituted $C_2$-$C_6$ alkynyl, and an optionally substituted $C_2$-$C_6$ alkenyl;

$R^{12}$ and $R^{13}$ each independently is selected from among hydrogen, F, Cl, $OR^A$, $NR^A R^B$, $SR^A$, an optionally substituted $C_1$-$C_6$ alkyl, $CF_3$, an optionally substituted $C_1$-$C_6$ heteroalkyl, an optionally substituted $C_2$-$C_6$ alkynyl, an optionally substituted $C_2$-$C_6$ alkenyl, and $(CH_2)_m R^C$;

$R^A$ and $R^B$ each independently is selected from among hydrogen, an optionally substituted $C_1$-$C_4$ alkyl, $CF_3$, and an optionally substituted $C_1$-$C_4$ heteroalkyl;

$R^C$ is selected from among an optionally substituted aryl and an optionally substituted heteroaryl that is optionally substituted with a substituent selected from among F, Cl, Br, I, CN, $OR^A$, $NO_2$, $NR^A R^B$, $SR^A$, $SOR^A$, $SO_2R^A$, an optionally substituted $C_1$-$C_4$ alkyl, $CF_3$, and an optionally substituted $C_1$-$C_4$ heteroalkyl;

$R^D$ is selected from among hydrogen, an optionally substituted $C_1$-$C_4$ alkyl, $CF_3$, and an optionally substituted $C_1$-$C_4$ heteroalkyl;

Z is $CR^A R^B$;

n is 0; and m is 1 or 2;

or a pharmaceutically acceptable salt thereof.

6. The compound of claim 1, wherein $R^2$ is $CF_3$.

7. A compound of Formula II:

(II)

wherein:
$R^1$ is selected from among $SR^A$, $NO_2$, $CN$, $CF_3$, $COR^A$, $CONR^AR^B$, $SOR^A$, and $SO_2R^A$;
$R^2$ is trifluoromethyl;
$R^3$ and $R^4$ each independently is selected from among hydrogen, F, Cl, $OR^A$, an optionally substituted $C_1$-$C_4$ alkyl, and $CF_3$;
$R^5$ is selected from among hydrogen, F, Cl and $CF_3$;
$R^{6a}$ and $R^{7a}$ each independently is selected from among hydrogen, an optionally substituted $C_1$-$C_6$ alkyl, $CF_3$, an optionally substituted $C_1$-$C_6$ heteroalkyl, an optionally substituted $C_2$-$C_6$ alkynyl, and an optionally substituted $C_2$-$C_6$ alkenyl;
$R^9$ is selected from an optionally substituted $C_1$-$C_8$ alkyl, an optionally substituted $C_2$-$C_8$ alkenyl, $CF_3$, an optionally substituted $C_2$-$C_8$ haloalkenyl, $C_1$-$C_8$ heteroalkyl, an optionally substituted $C_2$-$C_8$ heteroalkenyl, an optionally substituted $C_2$-$C_8$ alkynyl, an optionally substituted $C_2$-$C_8$ haloalkynyl, an optionally substituted $C_2$-$C_8$ heteroalkynyl, an optionally substituted heteroaryl, $CH(R^D)OR^A$, $CH(R^D)NR^AR^B$, $COR^A$, $CO_2R^A$, and $(CH_2)_mR^C$;
$R^{10}$ is selected from among hydrogen, an optionally substituted $C_1$-$C_6$ alkyl, $CF_3$, an optionally substituted $C_1$-$C_6$ heteroalkyl, an optionally substituted $C_2$-$C_6$ alkynyl, and an optionally substituted $C_2$-$C_6$ alkenyl;
$R^{12}$ and $R^{13}$ each independently is selected from among hydrogen, F, Cl, $OR^A$, $NR^AR^B$, $SR^A$, an optionally substituted $C_1$-$C_6$ alkyl, $CF_3$, an optionally substituted $C_1$-$C_6$ heteroalkyl, an optionally substituted $C_2$-$C_6$ alkynyl, an optionally substituted $C_2$-$C_6$ alkenyl, and $(CH_2)_mR^C$;
$R^A$ and $R^B$ each independently is selected from among hydrogen, an optionally substituted $C_1$-$C_4$ alkyl, $CF_3$, and an optionally substituted $C_1$-$C_4$ heteroalkyl;
$R^C$ is selected from among an optionally substituted aryl and an optionally substituted heteroaryl that is optionally substituted with a substituent selected from among F, Cl, Br, I, CN, $OR^A$, $NO_2$, $NR^AR^B$, $SR^A$, $SOR^A$, $SO_2R^A$, an optionally substituted $C_1$-$C_4$ alkyl, $CF_3$, and an optionally substituted $C_1$-$C_4$ heteroalkyl;
$R^D$ is selected from among hydrogen, an optionally substituted $C_1$-$C_4$ alkyl, $CF_3$, and an optionally substituted $C_1$-$C_4$ heteroalkyl;
Z is $CR^AR^B$;
n is 0; and
m is 1 or 2;
or a pharmaceutically acceptable salt thereof.

8. The compound of claim 1, wherein $R^3$, $R^4$, and $R^5$ each independently is selected from among hydrogen, F, Cl, and an optionally substituted $C_1$-$C_4$ alkyl.

9. The compound of claim 1, wherein $R^3$ is hydrogen.

10. The compound of claim 1, wherein $R^4$ is hydrogen.

11. The compound of claim 1, wherein $R^5$ is hydrogen.

12. The compound of claim 1, wherein $R^{6a}$ and $R^{7a}$ each independently is selected from among hydrogen, an optionally substituted $C_1$-$C_6$ alkyl, and an optionally substituted $C_1$-$C_6$ heterohaloalkyl.

13. The compound of claim 1, wherein $R^{6a}$ is hydrogen.

14. The compound of claim 1, wherein $R^{7a}$ is hydrogen or an optionally substituted $C_1$-$C_6$ alkyl.

15. The compound of claim 1, wherein $R^{7a}$ is hydrogen or methyl.

16. The compound of claim 1, wherein $R^{7a}$ is hydrogen.

17. The compound of claim 1, wherein $R^{7a}$ is methyl.

18. The compound of claim 1, wherein $R^{12}$ is selected from among hydrogen, F, Cl, $OR^A$, an optionally substituted $C_1$-$C_6$ alkyl, an optionally substituted $C_1$-$C_6$ heterohaloalkyl and $(CH_2)_mR^C$.

19. The compound of claim 1, wherein $R^{10}$ is hydrogen.

20. The compound of claim 1, wherein $R^9$ is selected from among an optionally substituted $C_1$-$C_4$ alkyl, $C_1$-$C_6$ haloalkyl, $CH(R^D)OR^A$, and $CH(R^D)NR^AR^B$.

21. A compound of Formula II:

(II)

wherein:
$R^1$ is selected from among $SR^A$, $NO_2$, $CN$, $CF_3$, $COR^A$, $CONR^AR^B$, $SOR^A$, and $SO_2R^A$;
$R^2$ is selected from among F, Cl, Br, I, $SR^A$, $NO_2$, $CN$, $CF_3$, $COR^A$, $CO_2R^A$, $CONR^AR^B$, $SOR^A$, $SO_2R^A$, $SO_2NR^AR^B$, $NHCOR^A$, and $NHCONR^AR^B$;
$R^3$ and $R^4$ each independently is selected from among hydrogen, F, Cl, $OR^A$, an optionally substituted $C_1$-$C_4$ alkyl, and $CF_3$;
$R^5$ is selected from among hydrogen, F, Cl and $CF_3$;
$R^{6a}$ and $R^{7a}$ each independently is selected from among hydrogen, an optionally substituted $C_1$-$C_6$ alkyl, $CF_3$, an optionally substituted $C_1$-$C_6$ heteroalkyl, an optionally substituted $C_2$-$C_6$ alkynyl, and an optionally substituted $C_1$-$C_6$ alkenyl;
$R^9$ is formyl, hydroxy $C_1$-$C_6$alkyl, hydroxyhalo $C_1$-$C_6$alkyl, $C_1$-$C_6$alkylsilyloxy $C_1$-$C_6$alkyl, $C_1$-$C_6$alkoxycarbonyl, amino $C_1$-$C_6$alkyl, or $C_1$-$C_6$alkylcarbonyloxy$C_1$-$C_6$alkyl;
$R^{10}$ is selected from among hydrogen, an optionally substituted $C_1$-$C_6$ alkyl, $CF_3$ an optionally substituted $C_1$-$C_6$ heteroalkyl, an optionally substituted $C_1$-$C_6$ alkynyl, and an optionally substituted $C_2$-$C_6$ alkenyl;
$R^{12}$ and $R^{13}$ each independently is selected from among hydrogen, F, Cl, $OR^A$, $NR^AR^B$, $SR^A$, an optionally substituted $C_1$-$C_6$ alkyl, $CF_3$, an optionally substituted $C_1$-$C_6$ heteroalkyl, an optionally substituted $C_2$-$C_6$ alkynyl, an optionally substituted $C_2$-$C_6$ alkenyl, and $(CH_2)_mR^C$;
$R^A$ is selected from among hydrogen, an optionally substituted $C_1$-$C_4$ alkyl and $CF_3$;

$R^B$ is selected from among hydrogen, an optionally substituted $C_1$-$C_4$ alkyl, $CF_3$, and an optionally substituted $C_1$-$C_4$ heteroalkyl;

$R^C$ is selected from among an optionally substituted aryl and an optionally substituted heteroaryl that is optionally substituted with a substituent selected from among F, Cl, Br, I, CN, $OR^A$, $NO_2$, $NR^AR^B$, $SR^A$, $SOR^A$, $SO_2R^A$, an optionally substituted $C_1$-$C_4$ alkyl, $CF_3$, and an optionally substituted $C_1$-$C_4$ heteroalkyl;

Z is $CR^AR^B$;

n is 0; and m is 1 or 2;

or a pharmaceutically acceptable salt thereof.

22. The compound of claim 21, wherein $R^9$ is formyl, hydroxymethyl, 1-hydroxy-2,2,2-trifluoroethyl, tributylsilyloxymethyl, ethoxycarbonyl, aminomethyl, or acetyoxymethyl.

23. The compound of claim 1, wherein $R^{12}$ and $R^{13}$ each independently is selected from among hydrogen, F, Cl, $OR^A$, an optionally substituted $C_1$-$C_6$ alkyl, $CF_3$ and $(CH_2)_mR^C$.

24. The compound of claim 1, wherein $R^{13}$ is hydrogen, F, OH or benzyl.

25. The compound of claim 1 of formula IIB:

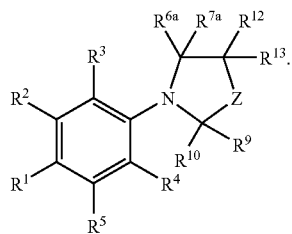

26. The compound of claim 1, wherein:

$R^1$ is $NO_2$ or CN;

$R^2$ is $CF_3$;

$R^3$, $R^4$, and $R^5$ each independently is selected from among hydrogen, F, Cl, and an optionally substituted $C_1$-$C_4$ alkyl;

$R^{6a}$ and $R^{7a}$ each independently is selected from among hydrogen and an optionally substituted $C_1$-$C_6$ alkyl;

$R^9$ is selected from among F, Cl, Br, I, an optionally substituted $C_1$-$C_4$ alkyl, $COR^A$, $CH(R^D)OR^A$, and $CH(R^D)NR^AR^B$;

$R^{10}$ is hydrogen; and $R^{12}$ and $R^{13}$ each independently is selected from among hydrogen, F, Cl, $OR^A$, an optionally substituted $C_1$-$C_6$ alkyl, an optionally substituted $C_1$-$C_6$ heterohaloalkyl and $(CH_2)_mR^C$.

27. The compound of claim 1, wherein:

$R^1$ is $NO_2$ or CN;

$R^2$ is trifluoromethyl;

$R^3$, $R^4$, and $R^5$ each is hydrogen;

$R^{7a}$ is hydrogen or methyl and $R^{6a}$ is hydrogen;

$R^9$ is selected from among formyl, hydroxymethyl and 1-hydroxy-2,2,2-trifluoroethyl;

$R^{10}$ is hydrogen;

$R^{12}$ is hydrogen; and $R^{13}$ is selected from among hydrogen, F, OH and benzyl.

28. A compound that is selected from among:

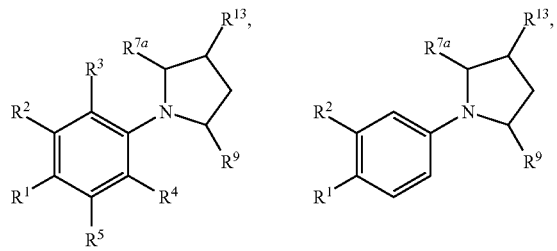

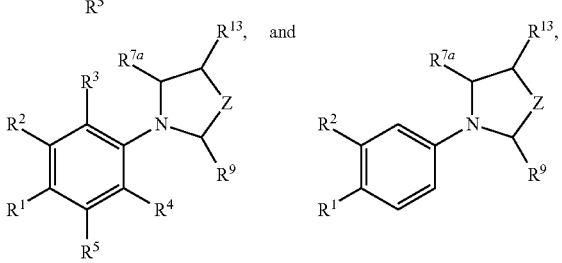

wherein:

$R^1$ is selected from among $SR^A$, $NO_2$, CN, $CF_3$, $CONR^AR^B$, $SOR^A$, and $SO_2R^A$;

$R^2$ is selected from F, Cl, Br, I, $SR^A$, $NO_2$, a substituted $C_1$-$C_4$ alkyl, $CF_3$, $COR^A$, $CO_2R^A$, $CONR^AR^B$, $SOR^A$, $SO_2R^A$, $SO_2NR^AR^B$, $NHCOR^A$, and $NHCONR^AR^B$;

$R^3$ and $R^4$ each independently is selected from among hydrogen, F, Cl, $OR^A$, an optionally substituted $C_1$-$C_4$ alkyl, and $CF_3$;

$R^5$ is selected from among hydrogen, F, Cl, an optionally substituted $C_1$-$C_4$ alkyl, and $CF_3$;

$R^{7a}$ is selected from among hydrogen, an optionally substituted $C_1$-$C_6$ alkyl, $CF_3$, an optionally substituted $C_1$-$C_6$ heteroalkyl, an optionally substituted $C_2$-$C_6$ alkynyl, and an optionally substituted $C_2$-$C_6$ alkenyl;

$R^9$ is selected from an optionally substituted $C_1$-$C_8$ alkyl, an optionally substituted $C_2$-$C_8$ alkenyl, $CF_3$, an optionally substituted $C_2$-$C_8$ haloalkenyl, an optionally substituted $C_2$-$C_8$ heteroalkenyl, an optionally substituted $C_2$-$C_8$ alkynyl, an optionally substituted $C_2$-$C_8$ haloalkynyl, an optionally substituted $C_2$-$C_8$ heteroalkynyl, an optionally substituted heteroaryl, $CH(R^D)OR^A$, $CH(R^D)NR^AR^B$, $COR^A$, and $(CH_2)_mR^C$;

$R^{13}$ is selected from among hydrogen, F, Cl, $OR^A$, $NR^AR^B$, $SR^A$, an optionally substituted $C_1$-$C_6$ alkyl, $CF_3$, an optionally substituted $C_1$-$C_6$ heteroalkyl, an optionally substituted $C_2$-$C_6$ alkynyl, an optionally substituted $C_2$-$C_6$ alkenyl, and $(CH_2)_mR^C$;

$R^A$ is selected from among hydrogen, an optionally substituted $C_1$-$C_4$ alkyl and $CF_3$;

$R^B$ is selected from among hydrogen, an optionally substituted $C_1$-$C_4$ alkyl, $CF_3$, and an optionally substituted $C_1$-$C_4$ heteroalkyl;

$R^C$ is selected from among an optionally substituted aryl and an optionally substituted heteroaryl that is optionally substituted with a substituent selected from among F, Cl, Br, I, CN, $OR^A$, $NO_2$, $NR^AR^B$, $SR^A$, $SOR^A$, $SO_2R^A$, an optionally substituted $C_1$-$C_4$ alkyl, $CF_3$, and an optionally substituted $C_1$-$C_4$ heteroalkyl;

$R^D$ is selected from among hydrogen, an optionally substituted $C_1$-$C_4$ alkyl, $CF_3$, and an optionally substituted $C_1$-$C_4$ heteroalkyl;

Z is $CR^AR^B$; and m is 1 or 2;

or a pharmaceutically acceptable salt thereof.

29. The compound of claim 28, wherein $R^{7a}$ is an optionally substituted $C_1$-$C_6$ heterohaloalkyl.

30. The compound of claim 28, wherein $R^{13}$ is an optionally substituted $C_1$-$C_6$ heterohaloalkyl.

31. The compound of claim 28, wherein the compound is:

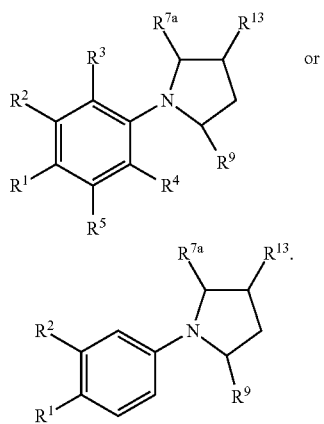

32. The compound of claim 28, wherein the compound is:

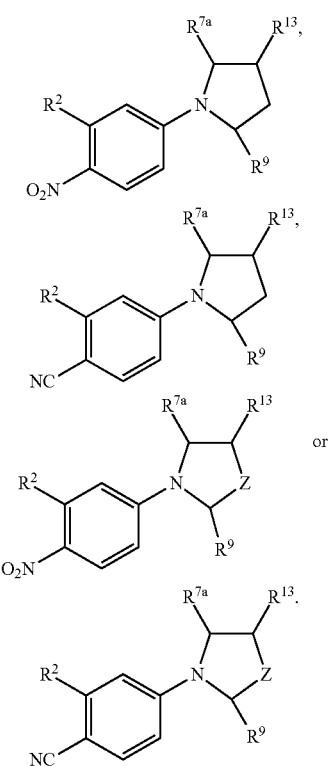

33. A compound of claim 1, wherein the compound is selected from among:
- (2R)—N-(4-nitro-3-trifluoromethylphenyl)-2-(hydroxymethyl)pyrrolidine;
- (2R)—N-(3-Trifluoromethyl-4-nitrophenyl)-2-formylpyrrolidine;
- (2R)—N-(3-Trifluoromethyl-4-nitrophenyl)-2-(1-(S)-hydroxy-2,2,2-trifluoroethyl)pyrrolidine;
- (2R)—N-(3-Trifluoromethyl-4-nitrophenyl)-2-(1-(R)-hydroxy-2,2,2-trifluoroethyl)-pyrrolidine;
- cis-2,5-Dimethyl-1-(4-nitro-3-trifluoromethylphenyl)-pyrrolidine;
- trans-2,5-dimethyl-1-(4-nitro-3-trifluoromethylphenyl)-pyrrolidine;
- 4-Benzyl-2-hydroxymethyl-1-(4-nitro-3-trifluoromethylphenyl)-pyrrolidine;
- 2-Fluoro-4-(2-hydroxymethyl-pyrrolidin-1-yl)-benzonitrile;
- 5-Hydroxymethyl-1-(4-nitro-3-trifluoromethylphenyl)-pyrrolidin-3-ol; and
- 2-(Aminomethyl)-1-(4-Nitro-3-trifluoromethylphenyl)-pyrrolidine;

and pharmaceutically acceptable salts thereof.

34. The compound of claim 1, wherein the compound is a selective androgen receptor modulator.

35. The selective androgen receptor modulator of claim 34, wherein the compound is an androgen receptor agonist.

36. The selective androgen receptor modulator of claim 34, wherein the compound is an androgen receptor antagonist.

37. The selective androgen receptor modulator of claim 34, wherein the compound is an androgen receptor partial agonist.

38. The selective androgen receptor modulator of claim 34, wherein the compound is a tissue-specific modulator.

39. The compound of claim 1, wherein the compound is a selective androgen binding compound.

40. A pharmaceutical composition, comprising a compound of claim 1 and a pharmaceutically acceptable carrier.

41. A compound of Formula II:

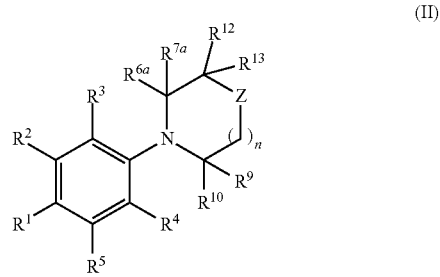

(II)

wherein:
$R^1$ is $COR^A$, $NO_2$ or CN;
$R^2$ is selected from among hydrogen, F, Cl, Br, I, $OR^A$, $SR^A$, $NO_2$, an optionally substituted $C_1$-$C_4$ alkyl, $CF_3$, $COR^A$, $CO_2R^A$, $CONR^AR^B$, $SOR^A$, $SO_2R^A$, $SO_2NR^AR^B$, $NHCOR^A$, and $NHCONR^AR^B$;
$R^3$, $R^4$, and $R^5$ each independently is selected from among hydrogen, Cl, $OR^A$, an optionally substituted $C_1$-$C_4$ alkyl, and $CF_3$;
$R^{6a}$ and $R^{7a}$ each independently is selected from among hydrogen, an optionally substituted $C_1$-$C_6$ alkyl, $CF_3$, an optionally substituted $C_1$-$C_6$ heteroalkyl, an optionally substituted $C_2$-$C_6$ alkynyl, and an optionally substituted $C_2$-$C_6$ alkenyl; or $R^{6a}$ and $R^{7a}$ together form a carbonyl;
$R^9$ is selected from among $CH(R^D)OR^A$ and $CH(R^D)N$-$R^AR^B$;
$R^{10}$ is selected from among hydrogen, an optionally substituted $C_1$-$C_6$ alkyl, $CF_3$, an optionally substituted $C_1$-$C_6$ heteroalkyl, an optionally substituted $C_2$-$C_6$ alkynyl, and an optionally substituted $C_2$-$C_6$ alkenyl;
$R^{12}$ and $R^{13}$ each independently is selected from among hydrogen, F, Cl, $OR^A$, $NR^AR^B$, $SR^A$, an optionally substituted $C_1$-$C_6$ alkyl, $CF_3$, an optionally substituted $C_1$-$C_6$ heteroalkyl, an optionally substituted $C_2$-$C_6$ alkynyl, an optionally substituted $C_2$-$C_6$ alkenyl, and $(CH_2)_m R^C$;

$R^A$ is selected from among hydrogen, an optionally substituted $C_1$-$C_4$ alkyl and $CF_3$;

$R^B$ is selected from among hydrogen, an optionally substituted $C_1$-$C_4$ alkyl, $CF_3$, and an optionally substituted $C_1$-$C_4$ heteroalkyl;

$R^C$ is selected from among an optionally substituted aryl and an optionally substituted heteroaryl that is optionally substituted with a substituent selected from among F, Cl, Br, I, CN, $OR^A$, $NO_2$, $NR^A R^B$, $SR^A$, $SOR^A$, $SO_2 R^A$, an optionally substituted $C_1$-$C_4$ alkyl, $CF_3$, and an optionally substituted $C_1$-$C_4$ heteroalkyl;

$R^D$ is selected from among an optionally substituted $C_1$-$C_4$ alkyl, $CF_3$, and an optionally substituted $C_1$-$C_4$ heteroalkyl;

Z is $CR^A R^B$;

n is 0; and m is 1 or 2;

or a pharmaceutically acceptable salt thereof.

42. A compound of claim 41, wherein the compound is selected from among:
- (2R)—N-(4-nitrophenyl)-2-(1-(S)-hydroxy-2,2,2-trifluoroethyl)pyrrolidine;
- (2R)—N-(4-nitrophenyl)-2-(R)-(1-(R)-hydroxy-2,2,2-trifluoroethyl)pyrrolidine;
- (2R)—N-(4-nitrophenyl)-2-(1-(S)-hydroxy-2,2,2-trifluoroethyl)pyrrolidine; and
- (2R)—N-(4-nitrophenyl)-2-(1-(R)-hydroxy-2,2,2-trifluoroethyl)pyrrolidine;

and pharmaceutically acceptable salts thereof.

43. A pharmaceutical composition, comprising a compound of claim 41 and a pharmaceutically acceptable carrier.

44. A pharmaceutical composition, comprising a compound of claim 28 and a pharmaceutically acceptable carrier.

* * * * *

UNITED STATES PATENT AND TRADEMARK OFFICE
CERTIFICATE OF CORRECTION

PATENT NO.         : 8,519,158 B2
APPLICATION NO.    : 10/590119
DATED              : August 27, 2013
INVENTOR(S)        : Lin Zhi et al.

It is certified that error appears in the above-identified patent and that said Letters Patent is hereby corrected as shown below:

On the title page

In column 2 (page 3, item 56) at line 38, Under Other Publications, change "p-di-(2 chloropropyl)aminolphenylalkanoic" to --p-[di-(2-chloropropyl)amino]phenylalkanoic--.

In the specification

In column 5 at lines 39-43, Change "In certain embodiments, provided herein are methods for identifying a compound that is capable of modulating an activity of an androgen receptor, by contacting a cell expressing an androgen receptor with a compound provided herein; and monitoring an effect of the compound upon the cell." to --In certain embodiments, provided herein are methods for modulating an activity of an androgen receptor by contacting an androgen receptor with at least one compound provided herein. In certain such embodiments, the androgen receptor is in a cell.--.

In column 5 at line 44, Before "provided" delete "the".

In column 21 at line 45, Change "$CR^A R^A$," to --$CR^A R^B$,--.

In column 24, lines 61-62, Change "acetyoxymethyl." to --acetyloxymethyl.--.

In column 24, line 64, Change "acetyoxymethyl." to --acetyloxymethyl.--.

In column 27, line 6 (approx.), Change "acetyoxymethyl." to --acetyloxymethyl.--.

In column 29, lines 53-54, Change "acetyoxymethyl." to --acetyloxymethyl.--.

In column 32 at line 23, Change "$R^{16}$" to --$R^{26}$--.

In column 38 at line 14, Change "tort" to --tert--.

In column 63 at line 43, Change "(e.g," to --(e.g.,--.

In the claims

In column 84 at line 26, In Claim 1, change "$R^3$" to --$R^5$--.

In column 88 at line 7, In Claim 12, change "$C_1$-$C_6$heterohaloalkyl." to --$C_1$-$C_6$ heterohaloalkyl.--.

Signed and Sealed this
Twenty-third Day of February, 2016

Michelle K. Lee
*Director of the United States Patent and Trademark Office*

CERTIFICATE OF CORRECTION (continued)
U.S. Pat. No. 8,519,158 B2

In the claims

In column 88 at line 52, In Claim 21, change "$C_1$-$C_6$ alkenyl;" to --$C_2$-$C_6$ alkenyl;--.

In column 88 at line 57, In Claim 21, change "$CF_3$" to --$CF_3$,--.

In column 88 at line 58, In Claim 21, change "$C_1$-$C_6$" to --$C_2$-$C_6$--.

In column 89 at lines 17-18, In Claim 22, change "acetyoxymethyl." to --acetyloxymethyl.--.

In column 94 at line 9, In Claim 42, change "(2R)" to --(2S)--.

In column 94 at line 11, In Claim 42, change "(2R)" to --(2S)--.